US012365927B2

(12) United States Patent
Savile et al.

(10) Patent No.: US 12,365,927 B2
(45) Date of Patent: *Jul. 22, 2025

(54) ENGINEERED KETOREDUCTASE POLYPEPTIDES

(71) Applicant: Codexis, Inc., Redwood City, CA (US)

(72) Inventors: Christopher Savile, Santa Clara, CA (US); John M. Gruber, El Dorado Hills, CA (US); Emily Mundorff, Garden City, NY (US); Gjalt W. Huisman, Redwood City, CA (US); Steven J. Collier, Concord, MA (US)

(73) Assignee: Codexis, Inc., Redwood City, CA (US)

(*) Notice: Subject to any disclaimer, the term of this patent is extended or adjusted under 35 U.S.C. 154(b) by 135 days.

This patent is subject to a terminal disclaimer.

(21) Appl. No.: 18/049,758

(22) Filed: Oct. 26, 2022

(65) Prior Publication Data

US 2023/0104779 A1 Apr. 6, 2023

Related U.S. Application Data

(60) Continuation of application No. 16/932,084, filed on Jul. 17, 2020, now Pat. No. 11,512,332, which is a continuation of application No. 15/982,291, filed on May 17, 2018, now Pat. No. 10,752,926, which is a division of application No. 15/489,946, filed on Apr. 18, 2017, now Pat. No. 10,006,069, which is a division of application No. 14/954,564, filed on Nov. 30, 2015, now Pat. No. 9,657,320, which is a continuation of application No. 14/503,578, filed on Oct. 1, 2014, now Pat. No. 9,228,213, which is a continuation of application No. 13/610,166, filed on Sep. 11, 2012, now Pat. No. 8,877,475, which is a division of application No. 12/549,293, filed on Aug. 27, 2009, now Pat. No. 8,288,141.

(60) Provisional application No. 61/092,331, filed on Aug. 27, 2008.

(51) Int. Cl.
C12P 17/00 (2006.01)
C12N 9/04 (2006.01)
C12P 13/00 (2006.01)

(52) U.S. Cl.
CPC .......... C12P 17/00 (2013.01); C12N 9/0006 (2013.01); C12P 13/001 (2013.01); C12Y 101/01164 (2013.01); C12Y 101/01184 (2013.01)

(58) Field of Classification Search
CPC ...... C12P 17/00; C12P 13/001; C12N 9/0006; C12Y 101/01164; C12Y 101/01184
See application file for complete search history.

(56) References Cited

U.S. PATENT DOCUMENTS

| | | |
|---|---|---|
| 4,956,388 A | 9/1990 | Robertson et al. |
| 5,023,269 A | 6/1991 | Robertson et al. |
| 5,200,335 A | 4/1993 | Hummel et al. |
| 5,362,886 A | 11/1994 | Berglund |
| 5,491,243 A | 2/1996 | Berglund |
| 5,559,030 A | 9/1996 | Matsuyama et al. |
| 6,037,158 A | 3/2000 | Hummel et al. |
| 6,225,099 B1 | 5/2001 | Hummel et al. |
| 6,399,339 B1 | 6/2002 | Wolberg et al. |
| 6,531,308 B2 | 3/2003 | Hershberger et al. |
| 6,541,668 B1 | 4/2003 | Kjell et al. |
| 6,645,746 B1 | 11/2003 | Kizaki et al. |
| 6,800,477 B2 | 10/2004 | Patel et al. |
| 6,846,957 B2 | 1/2005 | Zelenin |
| 7,045,341 B2 | 5/2006 | Kamal et al. |
| 7,259,264 B2 | 8/2007 | Sturmer |
| 7,301,031 B2 | 11/2007 | Rozzell, Jr. et al. |
| 7,393,667 B2 | 7/2008 | Patel et al. |
| 7,435,563 B2 | 10/2008 | Sturmer |
| 7,488,833 B2 | 2/2009 | Kralik et al. |
| 7,498,448 B2 | 3/2009 | Sturmer et al. |
| 7,538,232 B2 | 5/2009 | Butchko et al. |
| 7,553,970 B2 | 6/2009 | Berendes et al. |
| 8,288,141 B2 | 10/2012 | Savile et al. |
| 8,877,475 B2 | 11/2014 | Savile et al. |
| 9,228,213 B2 | 1/2016 | Savile et al. |
| 9,657,320 B2 | 5/2017 | Savile et al. |

(Continued)

FOREIGN PATENT DOCUMENTS

| | | |
|---|---|---|
| EP | 0273658 B1 | 10/1990 |
| EP | 0457559 A2 | 11/1991 |

(Continued)

OTHER PUBLICATIONS

Cooley, J.H., et al., "Amine Dealkylations with Acyl Chlorides", Synthesis, 1:1-7, 1989.
Deeter, J., et al., "Asymmetric Synthesis and Absolute Stereochemistry of LY248686", Tetrahedron Letters, 31 (49):7101-7104, 1990.
He, S. Z., et al., "Synthesis of Antidepressant Duloxetine Via Asymmetric Transfer Hydrogenation", Chinese Chemical Letters, 19: 23-25, 2008.
Kamal, A., et al., Chemoenzymatic Synthesis of Duloxetine and its Enantiomer: Lipase-Catalyzed Resolution of 3-hydroxy-3-(2-thienyl) propanenitrile, Tetrahedron Letters, 44:4783-4787, 2003.

(Continued)

*Primary Examiner* — Iqbal H Chowdhury
(74) *Attorney, Agent, or Firm* — FisherBroyles, LLP; Adam K. Whiting

(57) ABSTRACT

The present disclosure provides engineered ketoreductase enzymes having improved properties as compared to a naturally occurring wild-type ketoreductase enzyme. Also provided are polynucleotides encoding the engineered ketoreductase enzymes, host cells capable of expressing the engineered ketoreductase enzymes, and methods of using the engineered ketoreductase enzymes to synthesize a variety of chiral compounds. The engineered ketoreductase polypeptides are optimized for catalyzing the conversion of N-methyl-3-keto-3-(2-thienyl)-1-propanamine to (S)—N-methyl-3-hydroxy-3-(2-thienyl)-1-propanamine.

7 Claims, 1 Drawing Sheet

Specification includes a Sequence Listing.

(56) References Cited

U.S. PATENT DOCUMENTS

| | | |
|---|---|---|
| 10,006,069 B2 | 6/2018 | Savile et al. |
| 10,752,926 B2 | 8/2020 | Savile et al. |
| 11,512,332 B2 * | 11/2022 | Savile ............ C12Y 101/01184 |
| 2003/0181319 A1 | 9/2003 | Tucker et al. |
| 2004/0023250 A1 | 2/2004 | Nanduri et al. |
| 2005/0197503 A1 | 9/2005 | Schiffers et al. |
| 2006/0167278 A1 | 7/2006 | Inoue et al. |
| 2006/0211099 A1 | 9/2006 | Althofer et al. |
| 2006/0264641 A1 | 11/2006 | Berendes et al. |
| 2007/0238883 A1 | 10/2007 | Ini et al. |
| 2008/0005078 A1 | 1/2008 | Dampier et al. |
| 2008/0050787 A1 | 2/2008 | Nagai et al. |
| 2008/0206824 A1 | 8/2008 | Sturmer et al. |
| 2008/0220484 A1 | 9/2008 | Breuer et al. |
| 2008/0318288 A1 | 12/2008 | Sturmer et al. |

FOREIGN PATENT DOCUMENTS

| | | |
|---|---|---|
| EP | 0650965 B1 | 2/2001 |
| EP | 1506965 A1 | 2/2005 |
| EP | 1566383 A1 | 8/2005 |
| EP | 1171417 B1 | 11/2005 |
| EP | 1587801 B1 | 1/2007 |
| EP | 1539673 B1 | 10/2007 |
| IN | 1573/DEL/2004 | 7/2006 |
| WO | 2003/062219 A1 | 7/2003 |
| WO | 2004/005239 A1 | 1/2004 |
| WO | 2004/005307 A1 | 1/2004 |
| WO | 2004/011452 A1 | 2/2004 |
| WO | 2004/055194 A1 | 7/2004 |
| WO | 2005/021527 A2 | 3/2005 |
| WO | 2005/080370 A1 | 9/2005 |
| WO | 2004/031168 A2 | 4/2007 |
| WO | 2007/095200 A2 | 8/2007 |
| WO | 2007/143065 A2 | 12/2007 |

OTHER PUBLICATIONS

Liu, D., et al., "Practical Synthesis of Enantiopure Gamma-Amino Alcohols by Rhodium-Catalyzed Asymmetric Hydrogenation of Beta-Secondary-Amino Ketones", Angewandte Chemie, 44:1687-1689, 2005.

Liu, H., et al., "Chemo-Enzymatic Synthesis of the Antidepressant Duloxetine and its Enantiomer", Chirality, 12:26-29, 2000.

Niefind, K., et al., "The Crystal Structure of R-Specific Alcohol Dehydrogenase from Lactobacillus brevis Suggests the Structural Basis of its Metal Dependency", J. Mol. Biol., 327:317-328, 2003.

Sakai, K., et al., "Resolution of 3-(methylamino)-1-(2-thienyl)propan-1-ol, a New Key Intermediate for Duloxetine, with (S)-mandelic Acid", Tetrahedron: Asymmetry, 14:1631-1636, 2003.

Schneider, F., et al., "NADPH dependent R-specific alcohol dehydrogenase [Lactobacillus kefiri]", NCBI Database, AAP94029 (submitted 2003).

Niefind, K., et al., "Chain A, Crystal Structure of R-Alcohol Dehydrogenase (Radh) (Apoenyzme) From Lactobacillus brevis", NCBI database, 1NXQ_A (submitted 2003).

Goldberg, K., et al., "Biocatalytic ketone reduction-a powerful tool for the production of chiral alcohols-part II: whole-cell reductions," Applied Microbiology and Biotechnology, 76(2):249-255, Aug. 2007.

Fujima, Y., et al., "Synthesis of (S)-3-(N-Methylamino)-1-(2-thienyl)propan-1-ol: Revisiting Eli Lilly's Resolution-Racemization-Recycle Synthesis of Duloxetine for Its Robust Processes," Organic Process Research & Development, 10:905-913, 2006.

\* cited by examiner

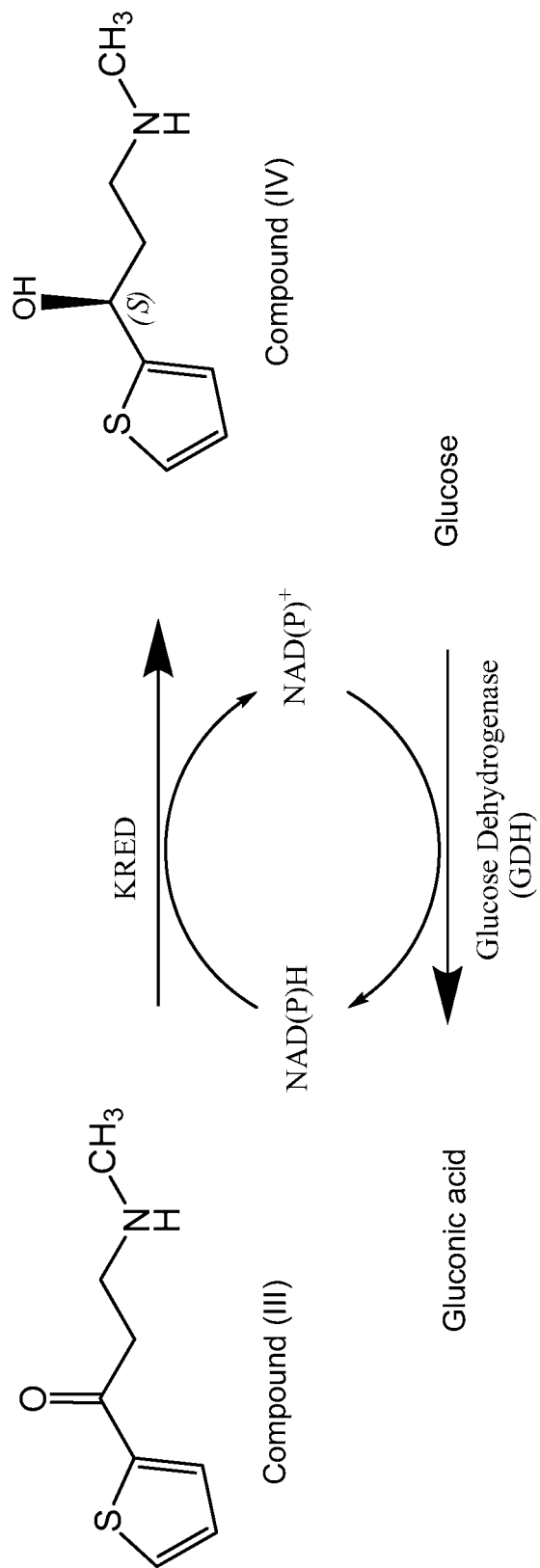

SEQUENCE LISTING

```
Sequence total quantity: 63
SEQ ID NO: 1              moltype = DNA    length = 759
FEATURE                   Location/Qualifiers
misc_feature              1..759
                          note = Codon Optimized L. Kefir Sequence
source                    1..759
                          mol_type = other DNA
                          organism = synthetic construct
SEQUENCE: 1
atgaccgatc gtctgaaggg caaagtagcc atcgtaaccg gcgggactct gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg catccgatga agcaggctgg acgaaactgt tcgacaccac cgaggaggca  240
ttcggcccgg ttacgaccgt cgtgaacaat gcagggattg cagtttccaa agcgttgaa   300
gacactacca cggaggaatg gcgtaaactg ctgtccgtta atctggatgg tgttttttc   360
ggcacccgtc tgggcattca gcgcatgaaa aataaaggct tgggcgctag catcatcaat  420
atgagcagta ttgaggggtt cgtaggcgat ccgacgctgg gggcatacaa cgcttccaag  480
ggggcggtac gtatcatgtc gaaaagcgca gcgctggatt gcgcactgaa ggactacgat  540
gtgcgtgtca acacagtaca tccgggctat atcaagaccc cgctggtcga tgatctggaa  600
ggtgctgagg aaatgatgtc acagcgtacg aaaaccccta tgggccacat tggcgaaccg  660
aatgacatcg catggatctg tgtgtacctg gcatctgacg aatcgaaatt tgcgacgggt  720
gcagaatttg tggtcgacgg cgggtatacc gcacagtga                        759

SEQ ID NO: 2              moltype = AA    length = 252
FEATURE                   Location/Qualifiers
REGION                    1..252
                          note = Translation of Codon Optimized L. kefir Sequence
source                    1..252
                          mol_type = protein
                          organism = synthetic construct
SEQUENCE: 2
MTDRLKGKVA IVTGGTLGIG LAIADKFVEE GAKVVITGRH ADVGEKAAKS IGGTDVIRFV   60
QHDASDEAGW TKLFDTTEEA FGPVTTVVNN AGIAVSKSVE DTTTEEWRKL LSVNLDGVFF  120
GTRLGIQRMK NKGLGASIIN MSSIEGFVGD PTLGAYNASK GAVRIMSKSA ALDCALKDYD  180
VRVNTVHPGY IKTPLVDDLE GAEEMMSQRT KTPMGHIGEP NDIAWICVYL ASDESKFATG  240
AEFVVDGGYT AQ                                                     252

SEQ ID NO: 3              moltype = DNA    length = 762
FEATURE                   Location/Qualifiers
misc_feature              1..762
                          note = Codon Optimized L. Brevis Sequence
source                    1..762
                          mol_type = other DNA
                          organism = synthetic construct
SEQUENCE: 3
atgtctaacc gtctggatgg caaagtagcc atcattaccg gcgggactct gggtatcggt   60
ttggcaatcg ccacgaaatt tgtagaggag ggtgcgaaag taatgattac tggtcgtcac  120
tccgatgtag gtgaaaaggc cgccaaatca gtaggcgctc cggatcagat tcagtttttt  180
cagcacgatt catccgatga agatggctgg acgaaactgt tcgacgccac cgagaaagca  240
ttcggcccgg ttagcacctt agtgaacaat gcagggattg cagttaacaa agcgttgaa   300
gaaactacca cggccgaatg gcgtaaactg ctggccgtta atctggatgg tgttttttc   360
ggcacccgtc tgggcattca gcgcatgaaa aataaaggct tgggcgctag catcatcaat  420
atgagcagta ttgaggggtt cgtaggcgat ccgagcctgg gggcatacaa cgcttccaag  480
ggggcggtac gtatcatgtc gaaaagcgca gcgctggatt gcgcactgaa ggactacgat  540
gtgcgtgtca acacagtaca tccgggctat atcaagaccc cgctggtcga tgatctgccg  600
ggtgctgagg aagcgatgtc acagcgtacg aaaaccccta tgggccacat tggcgaaccg  660
aatgacatcg catatatctg tgtgtacctg gcatctaatg aatcgaaatt tgcgacgggt  720
tccgaatttg tggtcgacgg cgggtatacc gcacagtaat ga                    762

SEQ ID NO: 4              moltype = AA    length = 252
FEATURE                   Location/Qualifiers
REGION                    1..252
                          note = Translation of Codon Optimized L. Brevis Sequence
source                    1..252
                          mol_type = protein
                          organism = synthetic construct
SEQUENCE: 4
MSNRLDGKVA IITGGTLGIG LAIATKFVEE GAKVMITGRH SDVGEKAAKS VGTPDQIQFF   60
QHDSSDEDGW TKLFDATEKA FGPVSTLVNN AGIAVNKSVE ETTTAEWRKL LAVNLDGVFF  120
GTRLGIQRMK NKGLGASIIN MSSIEGFVGD PSLGAYNASK GAVRIMSKSA ALDCALKDYD  180
VRVNTVHPGY IKTPLVDDLP GAEEAMSQRT KTPMGHIGEP NDIAYICVYL ASNESKFATG  240
SEFVVDGGYT AQ                                                     252

SEQ ID NO: 5              moltype = DNA    length = 759
FEATURE                   Location/Qualifiers
misc_feature              1..759
                          note = Variant of L. kefir
source                    1..759
```

```
                        mol_type = other DNA
                        organism = synthetic construct
SEQUENCE: 5
atgaccgatc gtctgaaggg caaagtagcc atcgtaaccg gcgggacact gggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg cgtccgatga agcaggctgg acgaaactgt tcgacaccac cgaggaggca   240
ttcggcccgg ttacgaccgt cgtgaacaat gcagggattg ggttgttaa aagcgttgaa    300
gacactacca cggaggaatg gcgtaaactg ctgtccgtta atctggatgg tgttttttc    360
ggcacccgtc tgggcattca gcgcatgaaa aataaaggct tgggcgctag catcatcaat   420
atgagcagta ttttcgggat ggtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgatgctcga tgatctggaa   600
ggtgctgagg aaatgtggtc acagcgtacg aaaaccccta tgggccacat tggcgaaccg   660
aatgacatcg catgggtctg tgtgtacctg gcatctggtg aatcgaaatt tgcgacgggt   720
gcagaatttg tggtcgacgg cgggtggacc gcacagtga                          759

SEQ ID NO: 6              moltype = AA  length = 252
FEATURE                   Location/Qualifiers
REGION                    1..252
                          note = Variant of L. kefir
source                    1..252
                          mol_type = protein
                          organism = synthetic construct
SEQUENCE: 6
MTDRLKGKVA IVTGGTLGIG LAIADKFVEE GAKVVITGRR ADVGEKAAKS IGGTDVIRFV    60
QHDASDEAGW TKLFDTTEEA FGPVTTVVNN AGIGVVKSVE DTTTEEWRKL LSVNLDGVFF   120
GTRLGIQRMK NKGLGASIIN MSSIFGMVGD PTLGAYNASK GAVRIMSKSA ALDCALKDYD   180
VRVNTVHPGP IKTPMLDDLE GAEEMWSQRT KTPMGHIGEP NDIAWVCVYL ASGESKFATG   240
AEFVVDGGWT AQ                                                        252

SEQ ID NO: 7              moltype = DNA  length = 759
FEATURE                   Location/Qualifiers
misc_feature              1..759
                          note = Variant of L. kefir
source                    1..759
                          mol_type = other DNA
                          organism = synthetic construct
SEQUENCE: 7
atgaccgatc gtctgaaggg caaagtagcc atcgtaaccg gcgggacact gggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg cgtccgatga agcaggctgg acgaaactgt tcgacaccac cgaggaggca   240
ttcggcccgg ttacgaccgt cgtgaacaat gcagggattg atgttgttaa aagcgttgaa   300
gacactacca cggaggaatg gcgtaaactg ctgtccgtta atctggatgg tgttttttc    360
ggcacccgtc tgggcattca gcgcatgaaa aataaaggct tgggcgctag catcatcaat   420
atgagcagta ttttcgggat ggtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgatgctcga tgatctggaa   600
ggtgctgagg aaatgtggtc acagcgtacg aaaaccccta tgggccacat tggcgaaccg   660
aatgacatcg catgggtctg tgtgtacctg gcatctggtg aatcgaaatt tgcgacgggt   720
gcagaatttg tggtcgacgg cgggtggacc gcacagtga                          759

SEQ ID NO: 8              moltype = AA  length = 252
FEATURE                   Location/Qualifiers
REGION                    1..252
                          note = Variant of L. kefir
source                    1..252
                          mol_type = protein
                          organism = synthetic construct
SEQUENCE: 8
MTDRLKGKVA IVTGGTLGIG LAIADKFVEE GAKVVITGRR ADVGEKAAKS IGGTDVIRFV    60
QHDASDEAGW TKLFDTTEEA FGPVTTVVNN AGIDVVKSVE DTTTEEWRKL LSVNLDGVFF   120
GTRLGIQRMK NKGLGASIIN MSSIFGMVGD PTLGAYNASK GAVRIMSKSA ALDCALKDYD   180
VRVNTVHPGP IKTPMLDDLE GAEEMWSQRT KTPMGHIGEP NDIAWVCVYL ASGESKFATG   240
AEFVVDGGWT AQ                                                        252

SEQ ID NO: 9              moltype = DNA  length = 759
FEATURE                   Location/Qualifiers
misc_feature              1..759
                          note = Variant of L. kefir
source                    1..759
                          mol_type = other DNA
                          organism = synthetic construct
SEQUENCE: 9
atgaccgatc gtctgaaggg caaagtagcc atcgtaaccg gcgggacact gggtatcggt    60
ttggcaatcg ccgataagtt tgtagaggag ggtgcgaaag tagttattac tggtcgtcgt   120
gcggatgtag gtgaaaaggc cgccaaatca atcggcggca ctgatgttat tcgctttgtc   180
cagcacgatg cgtccgatga agcaggctgg acgaaactgt tcgacaccac cgaggaggca   240
```

```
ttcggcccgg ttacgaccgt cgtgaacaat gcagggattg atgttgttaa aagcgttgaa    300
gacactacca cggaggaatg gcgtgaactg ctgtccgtta atctggatgg tgttttttc     360
ggcaccgtc  tgggcattca gcgcatgaaa aataaaggct tgggcgctag catcatcaat    420
atgagcagta ttttcgggat ggtaggcgat ccgacgctgg gggcatacaa cgcttccaag    480
ggggcggtac gtatcatgtc gaaaagcgca gcgctggatt gcgcactgaa ggactacgat    540
gtgcgtgtca acacagtaca tccgggcccc atcaagaccc cgatgctcga tgatctggaa    600
ggtgctgagg aaatgtggtc acagcgtacg aaaaccccta tgggccacat tggcgaaccg    660
aatgacatcg catgggtctg tgtgtacctg gcatctggtg aatcgaaatt tgcgacgggt    720
gcagaatttg tggtcgacgg cgggtggacc gcacagtga                          759

SEQ ID NO: 10            moltype = AA  length = 252
FEATURE                  Location/Qualifiers
REGION                   1..252
                         note = Variant of L. kefir
source                   1..252
                         mol_type = protein
                         organism = synthetic construct
SEQUENCE: 10
MTDRLKGKVA IVTGGTLGIG LAIADKFVEE GAKVVITGRR ADVGEKAAKS IGGTDVIRFV    60
QHDASDEAGW TKLFDTTEEA FGPVTTVVNN AGIDVVKSVE DTTTEEWREL LSVNLDGVFF    120
GTRLGIQRMK NKGLGASIIN MSSIFGMVGD PTLGAYNASK GAVRIMSKSA ALDCALKDYD    180
VRVNTVHPGP IKTPMLDDLE GAEEMWSQRT KTPMGHIGEP NDIAWVCVYL ASGESKFATG    240
AEFVVDGGWT AQ                                                       252

SEQ ID NO: 11            moltype = DNA  length = 759
FEATURE                  Location/Qualifiers
misc_feature             1..759
                         note = Variant of L. kefir
source                   1..759
                         mol_type = other DNA
                         organism = synthetic construct
SEQUENCE: 11
atgaccgatc gtctgaaggg caaagtagcc atcgtaaccg gcgggacact gggtatcggt    60
ttggcaatcg ccgataaatt tgtagaggag ggtgcgaaag tagttattac tggccgtcgt    120
gcggatgtag gtgaacgtgc cgccaaatca atcggcggca ctgatgttat tcgctttgtc    180
cagcacgatg cgtccgatga agcaggctgg acgaaactgt tcgacaccac cgaggaggca    240
ttcggcccgg ttacgaccgt cgtgaacaat gcagggattg acgttgttaa aagcgttgaa    300
gacactacca cggaggaatg gcgtaaactg ctgtccgtta atctggatgg tgttttttc    360
ggcaccgtc  tgggcattca gcgcatgaaa aataaaggct tgggcgctag catcatcaat    420
atgagcagta ttttcgggat ggtaggcgat ccgacggttg gggcatacaa cgcttccaag    480
ggggcggtac gtatcatgtc gaaaagcgca gcgctggatt gcgcactgaa ggactacgat    540
gtgcgtgtca acacagtaca tccgggcccc atcaagaccc cgatgctcga tgatgtggaa    600
ggtgctgagg aaatgtggtc acagcgtacg aaaaccccta tgggccacat tggcgaaccg    660
aatgacatcg catgggtctg tgtgtacctg gcatctggtg aatcgaaatt tgcgacgggt    720
gcagaatttg tgattgacgg cgggtggacc gcacagtga                          759

SEQ ID NO: 12            moltype = AA  length = 252
FEATURE                  Location/Qualifiers
REGION                   1..252
                         note = Variant of L. kefir
source                   1..252
                         mol_type = protein
                         organism = synthetic construct
SEQUENCE: 12
MTDRLKGKVA IVTGGTLGIG LAIADKFVEE GAKVVITGRR ADVGERAAKS IGGTDVIRFV    60
QHDASDEAGW TKLFDTTEEA FGPVTTVVNN AGIDVVKSVE DTTTEEWRKL LSVNLDGVFF    120
GTRLGIQRMK NKGLGASIIN MSSIFGMVGD PTVGAYNASK GAVRIMSKSA ALDCALKDYD    180
VRVNTVHPGP IKTPMLDDVE GAEEMWSQRT KTPMGHIGEP NDIAWVCVYL ASGESKFATG    240
AEFVIDGGWT AQ                                                       252

SEQ ID NO: 13            moltype = DNA  length = 759
FEATURE                  Location/Qualifiers
misc_feature             1..759
                         note = Variant of L. kefir
source                   1..759
                         mol_type = other DNA
                         organism = synthetic construct
SEQUENCE: 13
atgaccgatc gtctgaaggg caaagtagcc atcgtaaccg gcgggacact gggtatcggt    60
ttggcaatcg ccgataaatt tgtagaggag ggtgcgaaag tagttattac tggccgtcgt    120
gcggatgtag gtgaacgtgc cgccaaatca atcggcggca ctgatgttat tcgctttgtc    180
cagcacgatg cgtccgatga agcaggctgg acgaaactgt tcgacaccac cgaggaggca    240
ttcggcccgg ttacgaccgt cgtgaacaat gcagggattg acgttagcaa aagcgttgaa    300
gacactacca cggaggaatg gcgtaaactg ctgtccgtta atctggatgg tgttttttc    360
ggcaccgtc  tgggcattca gcgcatgaaa aataaaggct tgggcgctag catcatcaat    420
atgagcagta ttttcgggat ggtaggcgat ccgacggttg gggcatacaa cgcttccaag    480
ggggcggtac gtatcatgtc gaaaagcgca gcgctggatt gcgcactgaa ggactacgat    540
gtgcgtgtca acacagtaca tccgggcccc atcaagaccc cgatgctcga tgatgtggaa    600
ggtgctgagg aaatgtggtc acagcgtacg aaaaccccta tgggccacat tggcgaaccg    660
```

```
aatgacatcg catgggtctg tgtgtacctg gcatctggtg aatcgaaatt tgcgacgggt    720
gcagaatttg tgattgacgg cgggtggacc gcacagtga                           759

SEQ ID NO: 14           moltype = AA   length = 252
FEATURE                 Location/Qualifiers
REGION                  1..252
                        note = Variant of L. kefir
source                  1..252
                        mol_type = protein
                        organism = synthetic construct
SEQUENCE: 14
MTDRLKGKVA IVTGGTLGIG LAIADKFVEE GAKVVITGRR ADVGERAAKS IGGTDVIRFV     60
QHDASDEAGW TKLFDTTEEA FGPVTTVVNN AGIDVSKSVE DTTTEEWRKL LSVNLDGVFF    120
GTRLGIQRMK NKGLGASIIN MSSIFGMVGD PTVGAYNASK GAVRIMSKSA ALDCALKDYD    180
VRVNTVHPGP IKTPMLDDVE GAEEMWSQRT KTPMGHIGEP NDIAWVCVYL ASGESKFATG    240
AEFVIDGGWT AQ                                                       252

SEQ ID NO: 15           moltype = DNA   length = 759
FEATURE                 Location/Qualifiers
misc_feature            1..759
                        note = Variant of L. kefir
source                  1..759
                        mol_type = other DNA
                        organism = synthetic construct
SEQUENCE: 15
atgaccgatc gtctgaaggg caaagtagcc atcgtaaccg gcgggacact gggtatcggt     60
ttggcaatcg ccgataaatt tgtagaggag ggtgcgaaag tagttattac tggccgtcgt    120
gcggatgtag gtgaacgtgc cgccaaatca atcggcggca ctgatgttat tcgctttgtc    180
cagcacgatg cgtccgatga agcaggctgg acgaaactgt tcgacaccac cgaggaggca    240
ttcggcccgg ttacgaccgt cgtgaacaat gcagggattg acgttccgaa aagccgttgaa   300
gacactacca cggaggaatg gcgtaaactg ctgtccgtta atctggatgg tgttttttc     360
ggcacccgtc tgggcattca gcgcatgaaa aataaaggct tgggcgctag catcatcaat   420
atgagcagta ttttcgggat ggtaggcgat ccgacggttg gggcatacaa cgcttccaag    480
ggggcggtac gtatcatgtc gaaaagcgca gcgctggatt gcgcactgaa ggactacgat    540
gtgcgtgtca acacagtaca tccggggccc atcaagaccc cgatgctcga tgatgtggaa    600
ggtgctgagg aaatgtggtc acagcgtacg aaaaccccta tgggccacat tggcgaaccg    660
aatgacatcg catgggtctg tgtgtacctg gcatctggtg aatcgaaatt tgcgacgggt    720
gcagaatttg tgattgacgg cgggtggacc gcacagtga                           759

SEQ ID NO: 16           moltype = AA   length = 252
FEATURE                 Location/Qualifiers
REGION                  1..252
                        note = Variant of L. kefir
source                  1..252
                        mol_type = protein
                        organism = synthetic construct
SEQUENCE: 16
MTDRLKGKVA IVTGGTLGIG LAIADKFVEE GAKVVITGRR ADVGERAAKS IGGTDVIRFV     60
QHDASDEAGW TKLFDTTEEA FGPVTTVVNN AGIDVPKSVE DTTTEEWRKL LSVNLDGVFF    120
GTRLGIQRMK NKGLGASIIN MSSIFGMVGD PTVGAYNASK GAVRIMSKSA ALDCALKDYD    180
VRVNTVHPGP IKTPMLDDVE GAEEMWSQRT KTPMGHIGEP NDIAWVCVYL ASGESKFATG    240
AEFVIDGGWT AQ                                                       252

SEQ ID NO: 17           moltype = DNA   length = 759
FEATURE                 Location/Qualifiers
misc_feature            1..759
                        note = Variant of L. kefir
source                  1..759
                        mol_type = other DNA
                        organism = synthetic construct
SEQUENCE: 17
atgaccgatc gtctgaaggg caaagtagcc atcgtaaccg gcgggacact gggtatcggt     60
ttggcaatcg ccgataaatt tgtagaggag ggtgcgaaag tagttattac tggccgtcgt    120
gcggatgtag gtgaacgtgc cgccaaatca atcggcggca ctgatgttat tcgctttgtc    180
cagcacgatg cgtccgatga agcaggctgg acgaaactgt tcgacaccac cgaggaggca    240
ttcggcccgg ttacgaccgt cgtgaacaat gcagggattg acgttgttaa aagcgttgaa    300
gacactacca cggaggaatg gcgtaaactg ctgtccgtta atctggatgg tgttttttc     360
ggcacccgtc tgggcattca gcgcatgaaa aataaaggct tgggcgctag catcatcaat   420
atgagcagta ttttcgggat ggtaggcgat ccgacggttg gggcatacaa cgcttccaag    480
ggggcggtac gtatcatgtc gaaaagcgca gcgctggatt gcgcactgaa ggactacgat    540
gtgcgtgtca acacagtaca tccggggccc atcaagaccc cgatgctcga taatgtggaa    600
ggtgctgagg aaatgtggtc acagcgtacg aaaaccccta tgggccacat tggcgaaccg    660
aatgacatcg catgggtctg tgtgtacctg gcatctggtg aatcgaaatt tgcgacgggt    720
gcagaatttg tgattgacgg cggatggacc gcacagtga                           759

SEQ ID NO: 18           moltype = AA   length = 252
FEATURE                 Location/Qualifiers
REGION                  1..252
                        note = Variant of L. kefir
```

```
source                  1..252
                        mol_type = protein
                        organism = synthetic construct
SEQUENCE: 18
MTDRLKGKVA IVTGGTLGIG LAIADKFVEE GAKVVITGRR ADVGERAAKS IGGTDVIRFV    60
QHDASDEAGW TKLFDTTEEA FGPVTTVVNN AGIDVVKSVE DTTTEEWRKL LSVNLDGVFF   120
GTRLGIQRMK NKGLGASIIN MSSIFGMVGD PTVGAYNASK GAVRIMSKSA ALDCALKDYD   180
VRVNTVHPGP IKTPMLDNVE GAEEMWSQRT KTPMGHIGEP NDIAWVCVYL ASGESKFATG   240
AEFVIDGGWT AQ                                                      252

SEQ ID NO: 19           moltype = DNA  length = 759
FEATURE                 Location/Qualifiers
misc_feature            1..759
                        note = Variant of L. kefir
source                  1..759
                        mol_type = other DNA
                        organism = synthetic construct
SEQUENCE: 19
atgaccgatc gtctgaaggg caaagtagcc atcgtaaccg gcgggacact gggtatcggt    60
ttggcaatcg ccgataaatt tgtagaggag ggtgcgaaag tagttattac tggccgtcgt   120
gcggatgtag gtgaacgtgc cgccaaatca atcggcggca ctgatgttat tcgctttgtc   180
cagcacgatg cgtccgatga agcaggctgg acgaaactgt tcgacaccac cgaggaggca   240
ttcggcccgg ttacgaccgt cgtgaacaat gcagggattg acgttggtaa aagcgttgaa   300
gacactacca cggaggaatg gcgtaaactg ctgtccgtta atctggatgg tgttttttc    360
ggcacccgtc tgggcattca gcgcatgaaa aataaaggct gggcgctag catcatcaat   420
atgagcagta ttttcgggat ggtaggcgat ccgacggttg ggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgatgctcga tgatgtggaa   600
ggtgctgagg aaatgtggtc acagcgtacg aaaaccccta tgggccacat tggcgaaccg   660
aatgacatcg catgggtctg tgtgtacctg gcatctggtg aatcgaaatt tgcgacgggt   720
gcagaatttg tgattgacgg cgggtggacc gcacagtga                          759

SEQ ID NO: 20           moltype = AA  length = 252
FEATURE                 Location/Qualifiers
REGION                  1..252
                        note = Variant of L. kefir
source                  1..252
                        mol_type = protein
                        organism = synthetic construct
SEQUENCE: 20
MTDRLKGKVA IVTGGTLGIG LAIADKFVEE GAKVVITGRR ADVGERAAKS IGGTDVIRFV    60
QHDASDEAGW TKLFDTTEEA FGPVTTVVNN AGIDVGKSVE DTTTEEWRKL LSVNLDGVFF   120
GTRLGIQRMK NKGLGASIIN MSSIFGMVGD PTVGAYNASK GAVRIMSKSA ALDCALKDYD   180
VRVNTVHPGP IKTPMLDDVE GAEEMWSQRT KTPMGHIGEP NDIAWVCVYL ASGESKFATG   240
AEFVIDGGWT AQ                                                      252

SEQ ID NO: 21           moltype = DNA  length = 759
FEATURE                 Location/Qualifiers
misc_feature            1..759
                        note = Variant of L. kefir
source                  1..759
                        mol_type = other DNA
                        organism = synthetic construct
SEQUENCE: 21
atgaccgatc gtctgaaggg caaagtagcc atcgtaaccg gcgggacact gggtatcggt    60
ttggcaatcg ccgataaatt tgtagaggag ggtgcgaaag tagttattac tggccgtcgt   120
gcggatgtag gtgaacgtgc cgccaaatca atcggcggca ctgatgttat tcgctttgtc   180
cagcacgatg cgtccgatga agcaggctgg acgaaactgt tcgacaccac cgaggaggca   240
ttcggcccgg ttacgaccgt cgtgaacaat gcagggattg acgttgttaa aagcgttgaa   300
gacactacca cggaggaatg gcgtaaactg ctgtccgtta atctggatgg tgttttttc    360
ggcacccgtc tgggcattca gcgcatgaaa aataaaggct gggcgctag catcatcaat   420
atgagcagta ttttcgggat ggtaggcgat ccgacggttg ggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgatgctcga tgatgaggaa   600
ggtgctgagg aaatgtggtc acagcgtacg aaaaccccta tgggccacat tggcgaaccg   660
aatgacatcg catgggtctg tgtgtacctg gcatctggtg aatcgaaatt tgcgacgggt   720
gcagaatttg tgattgacgg cgggtggacc gcacagtga                          759

SEQ ID NO: 22           moltype = AA  length = 252
FEATURE                 Location/Qualifiers
REGION                  1..252
                        note = Variant of L. kefir
source                  1..252
                        mol_type = protein
                        organism = synthetic construct
SEQUENCE: 22
MTDRLKGKVA IVTGGTLGIG LAIADKFVEE GAKVVITGRR ADVGERAAKS IGGTDVIRFV    60
QHDASDEAGW TKLFDTTEEA FGPVTTVVNN AGIDVVKSVE DTTTEEWRKL LSVNLDGVFF   120
GTRLGIQRMK NKGLGASIIN MSSIFGMVGD PTVGAYNASK GAVRIMSKSA ALDCALKDYD   180
```

```
VRVNTVHPGP IKTPMLDDEE GAEEMWSQRT KTPMGHIGEP NDIAWVCVYL ASGESKFATG   240
AEFVIDGGWT AQ                                                     252

SEQ ID NO: 23              moltype = DNA  length = 759
FEATURE                    Location/Qualifiers
misc_feature               1..759
                           note = Variant of L. kefir
source                     1..759
                           mol_type = other DNA
                           organism = synthetic construct
SEQUENCE: 23
atgaccgatc gtctgaaggg caaagtagcc atcgtaaccg gcgggacact gggtatcggt    60
ttggcaatcg ccgataaatt tgtagaggag ggtgcgaaag tagttattac tggccgtcgt   120
gcggatgtag gtgaacgtgc cgccaaatca atcggcggca ctgatgttat tcgctttgtc   180
cagcacgatg cgtccgatga agcaggctgg acgaaactgt tcgacaccac cgaggaggca   240
ttcggcccgg ttacgaccgt cgtgaacaat gcagggattg acgttgttaa aagcgttgaa   300
gacactacca cggaggaatg gcgtaaactg ctgtccgtta atctggatgg tgttttttc    360
ggcacccgtc tgggcattca gcgcatgaaa aataaaggct gggcgctag catcatcaat   420
atgagcagta ttttcgggat ggtaggcgat ccgacggttg gggcatacag cgcttccaag   480
ggggcggtac gtatcatgtc gaaaagcgca gcgctggatt gcgcactgaa ggactacgat   540
gtgcgtgtca acacagtaca tccgggcccc atcaagaccc cgatgctcga tgatgtgaa    600
ggtgctgagg aaatgtggtc acagcgtacg aaaaccccat tgggccacat tggcgaaccg   660
aatgacatcg catgggtctg tgtgtacctg gcatctggtg aatcgaaatt tgcgacgggt   720
gcagaatttg tgattgacgg cgggtggacc gcacagtga                         759

SEQ ID NO: 24              moltype = AA  length = 252
FEATURE                    Location/Qualifiers
REGION                     1..252
                           note = Variant of L. kefir
source                     1..252
                           mol_type = protein
                           organism = synthetic construct
SEQUENCE: 24
MTDRLKGKVA IVTGGTLGIG LAIADKFVEE GAKVVITGRR ADVGERAAKS IGGTDVIRFV    60
QHDASDEAGW TKLFDTTEEA FGPVTTVVNN AGIDVVKSVE DTTTEEWRKL LSVNLDGVFF   120
GTRLGIQRMK NKGLGASIIN MSSIFGMVGD PTVGAYSASK GAVRIMSKSA ALDCALKDYD   180
VRVNTVHPGP IKTPMLDDVE GAEEMWSQRT KTPMGHIGEP NDIAWVCVYL ASGESKFATG   240
AEFVIDGGWT AQ                                                     252

SEQ ID NO: 25              moltype = DNA  length = 759
FEATURE                    Location/Qualifiers
misc_feature               1..759
                           note = Variant of L. kefir
source                     1..759
                           mol_type = other DNA
                           organism = synthetic construct
SEQUENCE: 25
atgaccgatc gtctgaaggg caaagtagcc atcgtaaccg gcgggacact gggtatcggt    60
ttggcaatcg ccgataaatt tgtagaggag ggtgcgaaag tagttattac tggccgtcgt   120
gcggatgtag gtgaacgtgc cgccaaatca atcggcggca ctgatgttat tcgctttatt   180
cagcacgatg cgtccgatga agcaggctgg acgaaactgt tcgacaccac cgaggaggca   240
ttcggcccgg ttacgaccgt cgtgaacaat gcagggattg acgttgttaa aagcgttgaa   300
gacactacca cggaggaatg gcataaactg ctgtccgtta atctggatgg tgttttttc    360
ggcacccgtc tgggcattca gcgcatgaaa aataaaggct gggcgctag catcatcaat   420
atgagcagta ttttcgggat ggtaggcgat ccgacggttg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgatgctcga tgatgtggaa   600
ggtgctgagg aaatgtggtc acagcgtacg aaaaccccta tgggccacat tggcgaaccg   660
aatgacatcg catgggtctg tgtgtacctg gcatctggtg aatcgaaatt tgcgacgggt   720
gcagaatttg tgattgacgg cgggtggacc gcacagtga                         759

SEQ ID NO: 26              moltype = AA  length = 252
FEATURE                    Location/Qualifiers
REGION                     1..252
                           note = Variant of L. kefir
source                     1..252
                           mol_type = protein
                           organism = synthetic construct
SEQUENCE: 26
MTDRLKGKVA IVTGGTLGIG LAIADKFVEE GAKVVITGRR ADVGERAAKS IGGTDVIRFI    60
QHDASDEAGW TKLFDTTEEA FGPVTTVVNN AGIDVVKSVE DTTTEEWHKL LSVNLDGVFF   120
GTRLGIQRMK NKGLGASIIN MSSIFGMVGD PTVGAYNASK GAVRIMSKSA ALDCALKDYD   180
VRVNTVHPGP IKTPMLDDVE GAEEMWSQRT KTPMGHIGEP NDIAWVCVYL ASGESKFATG   240
AEFVIDGGWT AQ                                                     252

SEQ ID NO: 27              moltype = DNA  length = 759
FEATURE                    Location/Qualifiers
misc_feature               1..759
                           note = Variant of L. kefir
```

```
source                  1..759
                        mol_type = other DNA
                        organism = synthetic construct
SEQUENCE: 27
atgaccgatc gtctgaaggg caaagtagcc atcgtaaccg gcgggacact gggtatcggt   60
ttggcaatcg ccgataaatt tgtagaggag ggtgcgaaag tagttattac tggccgtcgt  120
gcggatgtag gtgaacgtgc cgccaaatca atcggcggca ctgatgttat tcgctttgtc  180
cagcacgatg tgtccgatga agcaggctgg acgaaactgt tcgacaccac cgaggaggca  240
ttcggcccgg ttacgaccgt cgtgaacaat gcagggattg acgttgttaa aagcgttgaa  300
gacactacca cggaggaatg gcgtaaactg ctgtccgtta atctggatgg tgttttttc  360
ggcacccgtc tgggcattca gcgcatgaaa aataaaggct gggcgctag catcatcaat  420
atgagcagta ttttcgggat ggtaggcgat ccgacggttg gggcatacaa cgcttccaag  480
ggggcggtac gtatcatgtc gaaaagcgca gcgctggatt gcgcactgaa ggactacgat  540
gtgcgtgtca acacagtaca tccgggcccc atcaagaccc cgatgctcga tgatgtggaa  600
ggtgctgagg aaatgtggtc acagcgtacg aaaaccccta tgggccacat tggcgaaccg  660
aatgacatcg catgggtctg tgtgtacctg gcatctggtg aatcgaaatt tgcgacgggt  720
gcagaatttg tgattgacgg cgggtggacc gcacagtga                         759

SEQ ID NO: 28           moltype = AA  length = 252
FEATURE                 Location/Qualifiers
REGION                  1..252
                        note = Variant of L. kefir
source                  1..252
                        mol_type = protein
                        organism = synthetic construct
SEQUENCE: 28
MTDRLKGKVA IVTGGTLGIG LAIADKFVEE GAKVVITGRR ADVGERAAKS IGGTDVIRFV   60
QHDVSDEAGW TKLFDTTEEA FGPVTTVVNN AGIDVVKSVE DTTTEEWRKL LSVNLDGVFF  120
GTRLGIQRMK NKGLGASIIN MSSIFGMVGD PTVGAYNASK GAVRIMSKSA ALDCALKDYD  180
VRVNTVHPGP IKTPMLDDVE GAEEMWSQRT KTPMGHIGEP NDIAWVCVYL ASGESKFATG  240
AEFVIDGGWT AQ                                                     252

SEQ ID NO: 29           moltype = DNA  length = 759
FEATURE                 Location/Qualifiers
misc_feature            1..759
                        note = Variant of L. kefir
source                  1..759
                        mol_type = other DNA
                        organism = synthetic construct
SEQUENCE: 29
atgaccgatc gtctgaaggg caaagtagcc atcgtaaccg gcgggacact gggtatcggt   60
ttggcaatcg ccgataaatt tgtagaggag ggtgcgaaag tagttattac tggccgtcgt  120
gcggatgtag gtgaacgtgc cgccaaatca atcggcggca ctgatgttat tcgctttgtc  180
cagcacgatg cgtccgatga agcaggctgg acgaaactgt tcgacaccac cgaggaggca  240
ttcggcccgg ttacgaccgt cgtgaacaat gcagggattg acgttagcaa aagcgttgaa  300
gacactacca cggaggaatg gcgtaaactg ctgtccgtta atctggatgg tgttttttc   360
ggcacccgtc tgggcattca gcgcatgaaa aataaaggct gggcgctag catcatcaat  420
atgagcagta ttttcgggat ggtaggcgat ccgacggttg gggcatacaa cgcttccaag  480
ggggcggtac gtatcatgtc gaaaagcgca gcgctggatt gcgcactgaa ggactacgat  540
gtgcgtgtca acacagtaca tccgggcccc atcaagaccc cgatgctcga tgatcgtgaa  600
ggtgctgagg aaatgtggtc acagcgtacg aaaaccccta tgggccacat tggcgaaccg  660
aatgacatcg catgggtctg tgtgtacctg gcatctggtg aatcgaaatt tgcgacgggt  720
gcagaatttg tgattgacgg cgggtggacc gcacagtga                         759

SEQ ID NO: 30           moltype = AA  length = 252
FEATURE                 Location/Qualifiers
REGION                  1..252
                        note = Variant of L. kefir
source                  1..252
                        mol_type = protein
                        organism = synthetic construct
SEQUENCE: 30
MTDRLKGKVA IVTGGTLGIG LAIADKFVEE GAKVVITGRR ADVGERAAKS IGGTDVIRFV   60
QHDASDEAGW TKLFDTTEEA FGPVTTVVNN AGIDVSKSVE DTTTEEWRKL LSVNLDGVFF  120
GTRLGIQRMK NKGLGASIIN MSSIFGMVGD PTVGAYNASK GAVRIMSKSA ALDCALKDYD  180
VRVNTVHPGP IKTPMLDDRE GAEEMWSQRT KTPMGHIGEP NDIAWVCVYL ASGESKFATG  240
AEFVIDGGWT AQ                                                     252

SEQ ID NO: 31           moltype = DNA  length = 759
FEATURE                 Location/Qualifiers
misc_feature            1..759
                        note = Variant of L. kefir
source                  1..759
                        mol_type = other DNA
                        organism = synthetic construct
SEQUENCE: 31
atgaccgatc gtctgaaggg caaagtagcc atcgtaaccg gcgggacact gggtatcggt   60
ttggcaatcg ccgataaatt tgtagaggag ggtgcgaaag tagttattac tggccgtcgt  120
gcggatgtag gtgaacgtgc cgccaaatca atcggcggca ctgatgttat tcgctttgtc  180
```

```
cagcacgatg cgtccgatga agcaggctgg acgaaactgt tcgacaccac cgaggaggca   240
ttcggcccgg ttacgaccgt cgtgaacaat gcagggattg acgttgttaa aagcgttgaa   300
gacactacca cggaggaatg gcgtaaactg ctgtccgtta atctggatgg tgttttttc    360
ggcacccgtc tgggcattca gcgcatgaaa aataaaggct tgggcgctag catcatcaat   420
atgagcagta ttttcgggat ggtaggcgat ccgaattgtg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgatgctcga tgatgaggaa   600
ggtgctgagg aaatgtggtc acagcgtacg aaaaccccta tgggccacat tggcgaaccg   660
aatgacatcg catgggtctg tgtgtacctg gcatctggtg aatcgaaatt tgcgacgggt   720
gcagaatttg tgattgacgg cgggtggacc gcacagtga                          759

SEQ ID NO: 32            moltype = AA   length = 252
FEATURE                  Location/Qualifiers
REGION                   1..252
                         note = Variant of L. kefir
source                   1..252
                         mol_type = protein
                         organism = synthetic construct
SEQUENCE: 32
MTDRLKGKVA IVTGGTLGIG LAIADKFVEE GAKVVITGRR ADVGERAAKS IGGTDVIRFV    60
QHDASDEAGW TKLFDTTEEA FGPVTTVVNN AGIDVVKSVE DTTTEEWRKL LSVNLDGVFF   120
GTRLGIQRMK NKGLGASIIN MSSIFGMVGD PNVGAYNASK GAVRIMSKSA ALDCALKDYD   180
VRVNTVHPGP IKTPMLDDEE GAEEMWSQRT KTPMGHIGEP NDIAWVCVYL ASGESKFATG   240
AEFVIDGGWT AQ                                                      252

SEQ ID NO: 33            moltype = DNA   length = 852
FEATURE                  Location/Qualifiers
misc_feature             1..852
                         note = ADH from Candida magnoliae
source                   1..852
                         mol_type = other DNA
                         organism = synthetic construct
SEQUENCE: 33
atggcaaaga attttagcaa tgtagagtat cccgcacccc cccccgcaca tacaaagaat    60
gagagcttac aagtattaga tttatttaag ttaaatggaa aagtagcaag cataacagga   120
agcagcagcg gaataggata tgcattagca gaggcttttg cacaagtcgg agcagatgta   180
gcaatatggt ataatagcca tgatgcaaca ggaaaagcag aggcattagc aaagaagtat   240
ggagtaaagg taaaggcata taagcaaat gtaagcagca gcgatgcagt caagcaaaca   300
atagagcaac aaataaagga ttttggacat ttagatatag tagtagcaaa tgcaggaata   360
ccctggacaa agggagcata tatagatcaa gatgatgaca gcattttga ccaagtagta    420
gatgtagact taaagggagt aggatacgta gcaaagcatg caggaaggca ttttaggaa    480
aggtttgaga aagagggaaa aaagggagca ttagtattta cagcaagcat gagcggacat   540
atagtaaatg tcccccaatt ccaagcaaca tataatgcag caaaggcagg agtaaggcat   600
tttgcaaaga gcttagcagt cgagtttgca ccctttgcaa gggtaaatag cgtaagcccc   660
ggatatataa atacagagat aagcgatttc gtcccccaag agacacaaa taagtggtgg    720
agcttagtcc cctaggaag ggaggagag acagcagagt tagtaggagc atatttattc     780
ttagcaagcg atgcaggaag ctatgcaaca ggaacagata taatagtaga tggaggatat   840
acattaccct aa                                                      852

SEQ ID NO: 34            moltype = AA   length = 283
FEATURE                  Location/Qualifiers
REGION                   1..283
                         note = ADH from Candida magnoliae
source                   1..283
                         mol_type = protein
                         organism = synthetic construct
SEQUENCE: 34
MAKNFSNVEY PAPPPAHTKN ESLQVLDLFK LNGKVASITG SSSGIGYALA EAFAQVGADV    60
AIWYNSHDAT GKAEALAKKY GVKVKAYKAN VSSSDAVKQT IEQQIKDFGH LDIVVANAGI   120
PWTKGAYIDQ DDDKHFDQVV DVDLKGVGYV AKHAGRHFRE RFEKEGKKGA LVFTASMSGH   180
IVNVPQFQAT YNAAKAGVRH FAKSLAVEFA PFARVNSVSP GYINTEISDF VPQETQNKWW   240
SLVPLGRGGE TAELVGAYLF LASDAGSYAT GTDIIVDGGY TLP                    283

SEQ ID NO: 35            moltype = DNA   length = 1047
FEATURE                  Location/Qualifiers
misc_feature             1..1047
                         note = ADH from Rhodococcus erythropolis
source                   1..1047
                         mol_type = other DNA
                         organism = synthetic construct
SEQUENCE: 35
atgaaagcca ttcagtacac tcgtatcggt gcggaaccag aactgactga atcccgaag     60
ccggaaccgg gccgggcga agtactgctg gaagtcacgg cagctggcgt gtgccattcc    120
gatgatttca ttatgtctct gccggaagaa cagtacacct acggcctgcc gctgacccty   180
ggtcatgaag gtgctggtaa agttgccgca gttggcgaag tgttgaaggt tggatatt     240
ggcaccaatg tggttgtgta cggcccatgg ggttgtggca actgttggca ttgcagtcag   300
ggcctggaga actattgctc ccgtgcgcag gaactggtta ttaacccgcc tggtctgggt   360
gctccggggg ctttggcaga atttatgatt gtcgactcac acgtcatttt ggtcccgatt   420
ggcgatttag accctgttaa aactgttccg ttgactgatg cgggcctgac cccataccat   480
```

```
gcaatcaaac gctccctgcc gaaactgcgc ggcggctctt atgcagtagt gatcggtacg    540
ggtggcctgg gccacgtggc tatccaactg ctgcgtcatt tatctgctgc aacggtgatc    600
gccttggacg tttctgccga taaactggaa ctggctacca agtcggcgc acatgaagta     660
gtcctgtctg ataaagatgc agcggagaat gtgcgtaaaa ttactggtag ccaaggtgca    720
gcttggtgt tggattttgt gggctatcag cctaccattg acaccgccat ggcagtggcg     780
ggcgtgggct ctgacgtcac cattgttggt atcggtgatg gccaggcaca tgcgaaagtt    840
ggtttcttcc agagtcctta tgaggcatcg gttacggtac cttattgggg cgctcgtaat    900
gaactgatcg aattgatcga tctggcgcat gctggtattt tcgacattgc cgttgagacc    960
ttctctttgg ataatggtgc agaggccatat cgtcgcctgg ctgcgggcac actgtcaggc   1020
cgtgcggtag tcgtcccggg cctgtaa                                        1047

SEQ ID NO: 36          moltype = AA  length = 348
FEATURE                Location/Qualifiers
REGION                 1..348
                       note = ADH from Rhodococcus erythropolis
source                 1..348
                       mol_type = protein
                       organism = synthetic construct
SEQUENCE: 36
MKAIQYTRIG AEPELTEIPK PEPGPGEVLL EVTAAGVCHS DDFIMSLPEE QYTYGLPLTL     60
GHEGAGKVAA VGEGVEGLDI GTNVVVYGPW GCGNCWHCSQ GLENYCSRAQ ELGINPPGLG    120
APGALAEFMI VDSPRHLVPI GDLDPVKTVP LTDAGLTPYH AIKRSLPKLR GGSYAVVIGT    180
GGLGHVAIQL LRHLSAATVI ALDVSADKLE LATKVGAHEV VLSDKDAAEN VRKITGSQGA    240
ALVLDFVGYQ PTIDTAMAVA GVGSDVTIVG IGDGQAHAKV GFFQSPYEAS VTVPYWGARN    300
ELIELIDLAH AGIFDIAVET FSLDNGAEAY RRLAAGTLSG RAVVVPGL                 348

SEQ ID NO: 37          moltype = DNA  length = 1047
FEATURE                Location/Qualifiers
misc_feature           1..1047
                       note = YGL ADH from Saccharomyces cervisiae
source                 1..1047
                       mol_type = other DNA
                       organism = synthetic construct
SEQUENCE: 37
atgaccacgg aaaaaaccgt agtgttcgtg tcaggcgcga ccggttttat tgctctgcac     60
gtggtagatg acctgctgaa aactggttac aaagtaattg gttccggtcg ttctcaggaa    120
aaaaatgacg gtttgctgaa gaagttcaag tccaacccga atctgagcat ggaaattgtg    180
gaagatattg cggcaccaaa cgccttcgat aaagtattcc agaaacatgg taagaaaatt    240
aaagtggtcc tgcatatcgc gtccccggtc catttcaaca ctaccgattt cgaaaaagac    300
ttactgatcc cggcggtaaa cggtaccaaa tctattttgg aagcaattaa gaactatgcc    360
gcagacaccg tggaaaaagt ggttattact tcatctgttg ccgcgttggc ctctccgggt    420
gatatgaaag ataccagctt cgtggttaac gaagaatcct ggaataaaga cacctgggaa    480
tcgtgtcagg cgaatgctgt gtccgcttat tgcggttcta aaaaattcgc agagaaaacg    540
gcgtgggact tcttgaaga aaccagagc agcattaaat ttactctgtc cacgattaac     600
ccaggcttcg ttttggtcc gcagctgttc gccgactcct tgcgcaatgg tattaactct    660
agcagtgcga ttattgcgaa cctggtgtcg tataaattag gggataactt ctacaattat    720
agcggcccgt ttatcgacgt ccgtgacgtt tccaaagctc atctgctggc atttgagaaa    780
cctgaatgcg ccgtcagcg cctgtttctg tgcgaggata tgttctgttc ccaggaagcc    840
ctggacattc tgaacgaaga atttccacag ctgaagggca agatcgcaac gggcgaacct    900
ggcagcggct cgaccttcct gactaaaaat tgttgcaaat gcgacaatcg taaaactaaa    960
aacttgctgg gcttccagtt caacaaaatt cgcgactgca ttgtcgatac tgcgtcccag   1020
ttgctggaag tgcaaagcaa aagctaa                                       1047

SEQ ID NO: 38          moltype = AA  length = 348
FEATURE                Location/Qualifiers
REGION                 1..348
                       note = YGL ADH from Saccharomyces cervisiae
source                 1..348
                       mol_type = protein
                       organism = synthetic construct
SEQUENCE: 38
MTTEKTVVFV SGATGFIALH VVDDLLKTGY KVIGSGRSQE KNDGLLKKFK SNPNLSMEIV     60
EDIAAPNAFD KVFQKHGKEI KVVLHIASPV HFNTTDFEKD LLIPAVNGTK SILEAIKNYA    120
ADTVEKVVIT SSVAALASPG DMKDTSFVVN EESWNKDTWE SCQANAVSAY CGSKKFAEKT    180
AWDFLEENQS SIKFTLSTIN PGFVFGPQLF ADSLRNGINS SSAIIANLVS YKLGDNFYNY    240
SGPFIDVRDV SKAHLLAFEK PECAGQRLFL CEDMFCSQEA LDILNEEFPQ LKGKIATGEP    300
GSGSTFLTKN CCKCDNRKTK NLLGFQFNKF RDCIVDTASQ LLEVQSKS                 348

SEQ ID NO: 39          moltype = DNA  length = 939
FEATURE                Location/Qualifiers
misc_feature           1..939
                       note = YDL ADH from Saccharomyces cervisiae
source                 1..939
                       mol_type = other DNA
                       organism = synthetic construct
SEQUENCE: 39
atgtcttttc accaacagtt tttcacgctg aacaacggca ataaaatccc ggcgattgcc     60
atcatcggca ctggtacacg ttggtataaa aatgaagaaa ctgacgcgac cttctccaat    120
agtctggttg aacaaatcgt gtatgcgttg aaactgccgg ggattatcca catcgacgcc    180
```

```
gcggagattt atcgcaccta cccggaagtg ggtaaagcac tgtccctgac cgaaaagcct    240
cgtaacgcga tttttctgac ggataaatat tctccgcaga ttaaaatgag tgactcccct    300
gcggacggtc tggatttagc attgaagaaa atgggtacag attatgttga tttatatctg    360
ttacattccc cgtttgtttc gaaggaagtg aatggcttaa gcttagaaga ggcttggaaa    420
gatatggagc agttatacaa aagtggtaaa gctaaaaaca tcggggtttc caatttcgca    480
gtggaagacc tgcaacgtat cctgaaagtc gctgaagtta aacctcaggt caaccagatt    540
gagttctctc cgttcctgca aaaccaaaca ccaggcattt ataaattctg tcaggagcac    600
gatatcctgg tggaagcata ttctccgctg ggcccgctgc agaagaaaac cgcgcaggat    660
gacagccaac cattttttga gtacgtcaaa gaattgagcg aaaaatacat caaatcgtcg    720
gcccagatca tcctgcgctg ggtcactaaa cgcggtgtgc tgccagttac cacctcttca    780
aagcctcagc gcattagcga tgctcagaac ctgttttcct tcgacctgac agcggaagag    840
gttgataaaa tcacggagct gggtctggaa catgaaccgc tgcgcctgta ctggaataaa    900
ttgtatggca aatataacta cgccgcccag aaagtgtaa                           939

SEQ ID NO: 40          moltype = AA   length = 312
FEATURE                Location/Qualifiers
REGION                 1..312
                       note = YDL ADH from Saccharomyces cervisiae
source                 1..312
                       mol_type = protein
                       organism = synthetic construct
SEQUENCE: 40
MSFHQQFFTL NNGNKIPAIA IIGTGTRWYK NEETDATFSN SLVEQIVYAL KLPGIIHIDA     60
AEIYRTYPEV GKALSLTEKP RNAIFLTDKY SPQIKMSDSP ADGLDLALKK MGTDYVDLYL    120
LHSPFVSKEV NGLSLEEAWK DMEQLYKSGK AKNIGVSNFA VEDLQRILKV AEVKPQVNQI    180
EFSPFLQNQT PGIYKFCQEH DILVEAYSPL GPLQKKTAQD DSQPFFEYVK ELSEKYIKSE    240
AQIILRWVTK RGVLPVTTSS KPQRISDAQN LFSFDLTAEE VDKITELGLE HEPLRLYWNK    300
LYGKYNYAAQ KV                                                        312

SEQ ID NO: 41          moltype = DNA   length = 939
FEATURE                Location/Qualifiers
misc_feature           1..939
                       note = YPR ADH from Saccharomyces cervisiae
source                 1..939
                       mol_type = other DNA
                       organism = synthetic construct
SEQUENCE: 41
atgccggcaa cgttaaaaaa cagcagtgct accttaaaat taaacacagg tgcgagcatt     60
cctgtcctgg ggttcggcac ctggcgctct gtcgataaca acggctatca tagtgtaatt    120
gcggcgctga aagcgggta ccgtcatatc gatgctgcgg ccatctatct gaatgaagaa    180
gaagtcggcc gtgcgatcaa ggactccggt gttcctcgtg aagaaatttt tattaccacc    240
aaactgtggg gcaccgaaca acgcgatcca gaagcagccc tgaacaaatc tctgaaacgt    300
ctgggtctgg actatgtgga cctgtatctg atgcactggc cggtccctct gaaaacagac    360
cgtgtaactg acggtaacgt cctgtgcatc ccgaccctgg aagatggcac cgtggacatc    420
gataccaaag agtggaattt tattaaaacc tgggaactga tgcaggaatt gccgaaaact    480
ggtaagacca agccgtcgg tgtgtccaat tttccatca acaatatcaa agaactgctg    540
gaatcgccaa ataacaaggt cgttccagca accaatcaga tcgaattca tccgttgctg    600
ccgcaggatg aattaatcgc cttttgtaaa gaaaaaggca ttgtggtcga agcatatagc    660
ccattcggct ccgctaacgc cccgctgctg aaagaacagg cgattatcga tatggccaaa    720
aagcacggcg tcgaaccggc gcaactgatt atcagctggt cgattcagcg cggttatgtg    780
gtattggcca gtccgtaaa tccggagcgt atcgtgtcga actttaagat tttttaccctg    840
ccagaggatg atttcaaaac catctctaac ctgagcaaag tgcacggtac caaacgtgtc    900
gttgacatga aatggggctc atttccgatt tttcaataa                           939

SEQ ID NO: 42          moltype = AA   length = 312
FEATURE                Location/Qualifiers
REGION                 1..312
                       note = YPR ADH from Saccharomyces cervisiae
source                 1..312
                       mol_type = protein
                       organism = synthetic construct
SEQUENCE: 42
MPATLKNSSA TLKLNTGASI PVLGFGTWRS VDNNGYHSVI AALKAGYRHI DAAAIYLNEE     60
EVGRAIKDSG VPREEIFITT KLWGTEQRDP EAALNKSLKR LGLDYVDLYL MHWPVPLKTD    120
RVTDGNVLCI PTLEDGTVDI DTKEWNFIKT WELMQELPKT GKTKAVGVSN FSINNIKELL    180
ESPNNKVVPA TNQIEIHPLL PQDELIAFCK EKGIVVEAYS PFGSANAPLL KEQAIIDMAK    240
KHGVEPAQLI ISWSIQRGYV VLAKSVNPER IVSNFKIFTL PEDDFKTISN LSKVHGTKRV    300
VDMKWGSFPI FQ                                                        312

SEQ ID NO: 43          moltype = DNA   length = 1029
FEATURE                Location/Qualifiers
misc_feature           1..1029
                       note = GRE ADH from Saccharomyces cervisiae
source                 1..1029
                       mol_type = other DNA
                       organism = synthetic construct
SEQUENCE: 43
atgtctgtgt tcgtgtcagg cgcgaatggg tttattgctc agcacatcgt agatctgctg     60
ctgaaagaag attacaaagt aattggttcc gcacgttctc aggaaaaagc tgaaaatttg    120
```

```
accgaagcct tcggtaacaa cccgaaattt agcatggaag tggtgcctga tattagcaaa    180
ctggatgcct tcgatcatgt attccagaaa catggtaaag atattaaaat cgtcctgcat    240
accgcgtccc cgttttgttt cgatattacc gattccgaac gtgacttact gatcccggcg    300
gtaaacggtg tcaaaggtat tttgcacagt attaagaaat atgccgcaga cagcgtggaa    360
cgcgtggttc tgacttcatc ttacgccgcg gtatttgata tggcgaagga aaacgataag    420
agcctgacct tcaacgaaga atcctggaat ccggcgacct gggaatcgtg tcagagtgat    480
ccggtgaacg cttattgcgg ttctaaaaaa ttcgcagaga aagcagcgtg ggaattcttg    540
gaagaaaacc gtgatagcgt gaaatttgag ctgacagcgg tcaacccagt ttacgttttt    600
ggtccgcaga tgttcgataa agatgttaaa aaacacttga acaccagctg cgaactgttg    660
aactctctga tgcatctgag ccctgaagat aaaattccgg aactgttttg cggttacatc    720
gacgtccgtg acgttgcgaa agctcatctg gttgcatttc agaaacgtga aacaatcggt    780
cagcgcctga tcgtgtcgga ggcacgtttc acgatgcagg acgttctgga cattctgaac    840
gaagactttc cagtactgaa gggcaatatc ccggtcggca gcctggcag cggcgccacc    900
cataatactc tgggcgccac cctgacaat aaaaaaagca aaaaaattgct gggcttcaaa    960
ttccgtaatc tgaaagagac tattgacgat actgcgtccc agatcctgaa attcgaaggt   1020
cgcatttaa                                                           1029

SEQ ID NO: 44          moltype = AA   length = 342
FEATURE                Location/Qualifiers
REGION                 1..342
                       note = GRE ADH from Saccharomyces cervisiae
source                 1..342
                       mol_type = protein
                       organism = synthetic construct
SEQUENCE: 44
MSVFVSGANG FIAQHIVDLL LKEDYKVIGS ARSQEKAENL TEAFGNNPKF SMEVVPDISK     60
LDAFDHVFQK HGKDIKIVLH TASPFCFDIT DSERDLLIPA VNGVKGILHS IKKYAADSVE    120
RVVLTSSYAA VFDMAKENDK SLTFNEESWN PATWESCQSD PVNAYCGSKK FAEKAAWEFL    180
EENRDSVKFE LTAVNPVYVF GPQMFDKDVK KHLNTSCELV NSLMHLSPED KIPELFGGYI    240
DVRDVAKAHL VAFQKRETIG QRLIVSEARF TMQDVLDILN EDFPVLKGNI PVGKPGSGAT    300
HNTLGATLDN KKSKKLLGFK FRNLKETIDD TASQILKFEG RI                       342

SEQ ID NO: 45          moltype = DNA   length = 1041
FEATURE                Location/Qualifiers
misc_feature           1..1041
                       note = ADH from Streptomycel coelicolor
source                 1..1041
                       mol_type = other DNA
                       organism = synthetic construct
SEQUENCE: 45
atgaaggcac tgcagtaccg caccatcggc gcccgcccg aggtcgtcac cgtcccggac     60
ccggagccgg gccccggcca ggtgctgttg aaggtgaccg cggccggagt ctgccactcc   120
gacatcgcag tgatgagctg gcccgccgag ggcttcccgt acgagctgcc gctcaccctc   180
ggccacgagg gcgtcggcac cgtggccgcg ctcggccgcg gggtgacggg gctcgccgag   240
ggcgacgcgg tcgccgtgta cgggccctgg ggctgcggca cctgcgccaa gtgcgcggag   300
ggcaaggaga actactgcct gcgcgccgac gagctgggca tccgtccgcc ggggctcggg   360
cgtccggggt ccatggccga gtacctgctg atcgacgacc cccgcacct ggtccgctg     420
gacgggctcg acccggtcgc ggcggtgccg ctcaccgacg ccggactgac gccgtaccac   480
gcgatcaagc ggtcgctgcc caagctggtc ccggctcca ccgcggtggt catcggcacc   540
ggtggtctcg gccacgtcgc catccagctg ctgcgcgccc tgacgtccgc ccgggtggtc   600
gccctggacg tcagcgagga gaagctgcgc ctcgcccgtg cggtgggcgc gcacgaggcg   660
gtgctgtcgg acgcgaaggc cgcggacgcg gtgcgcgaga tcaccggcgg tctcggtgcc   720
gaggccgtgt tcgacttcgt cggcgtggcg cccaccgtgc agaccgccgg agccgtcgcg   780
gccgtcgagg gcgatgtcac cctggtcggc atcggcggcg atcgctgcc cgtcggcttc   840
ggcatgctgc cgttcgaggt gtcggtcaac gcccccact ggggcagccg cagcgagctg   900
accgaggtgc tgaacctggc ccgctccggt gccgtgtcgg tgcacaccga gacgtactcc   960
ctggacgacg ccccgctcgc ctacgagcgg ctgcacgagg gcagggtcaa cggccgcgcg  1020
gtgatcctgc cccacggctg a                                            1041

SEQ ID NO: 46          moltype = AA   length = 346
FEATURE                Location/Qualifiers
REGION                 1..346
                       note = ADH from Streptomycel coelicolor
source                 1..346
                       mol_type = protein
                       organism = synthetic construct
SEQUENCE: 46
MKALQYRTIG APPEVVTVPD PEPGPGQVLL KVTAAGVCHS DIAVMSWPAE GFPYELPLTL     60
GHEGVGTVAA LGAGVTGLAE GDAVAVYGPW GCGTCAKCAE GKENYCLRAD ELGIRPPGLG    120
RPGSMAEYLL IDDPRHLVPL DGLDPVAAVP LTDAGLTPYH AIKRSLPKLV PGSTAVVIGT    180
GGLGHVAIQL LRALTSARVV ALDVSEEKLR LARAVGAHEA VLSDAKAADA VREITGGLGA    240
EAVFDFVGVA PTVQTAGAVA AVEGDVTLVG IGGGSLPVGF GMLPFEVSVN APYWGSRSEL    300
TEVLNLARSG AVSVHTETYS LDDAPLAYER LHEGRVNGRA VILPHG                   346

SEQ ID NO: 47          moltype = DNA   length = 1032
FEATURE                Location/Qualifiers
misc_feature           1..1032
                       note = ADH from Sporobolomyces salmonicolor
source                 1..1032
```

```
                        mol_type = other DNA
                        organism = synthetic construct
SEQUENCE: 47
atggcaaaga tcgacaacgc agttctgccg gagggttctc tggtgctggt caccggcgcg    60
aacggctttg tcgctagcca tgtggtcgaa caactgctgg aacacggcta taaggtgcgc   120
ggcactgctc gctctgcctc caaactgggc aacctgcaga acgttggga cgccaaatac    180
cctggtcgtt tcgagactgc cgttgttgaa gacatgctga agcagggtgc atatgatgaa   240
gttattaaag gcgcggcagg tgtcgcccac atcgcgtccg tggtcagctt ttctaacaaa   300
tatgatgagg tggtaactcc tgcgatcggt ggcacgctgg atgccctgcg tgccgcagct   360
gctacgcctt ccgtgaaacg ttttgtgctg accagcagca ctgtttctgc actgattcca   420
aaacctaacg tcgaaggtat ttatctggat gagaagagct ggaacctgga aagcattgat   480
aaggctaaaa ccctgcctga atctgatccg cagaaaagcc tgtgggtcta cgccgcaagc   540
aaaacggaag cggaactggc tgcctggaaa ttcatggacg aaaacaaacc gcactttact   600
ctgaatgccg ttctgccaaa ctacactatc ggtaccattt tgacccaga aaccaatcc    660
ggttccactt ccggctggat gatgtctctg ttcaatggcg aagtatctcc ggcactggcg   720
ctgatgccgc cgcagtacta tgtctctgca gttgatatcg gtctgctgca cctgggttgt   780
ctggttctgc cgcaaatcga acgccgtcgt gtttacggca ccgcaggcac ctttgattgg   840
aacaccgttc tggcgacctt ccgtaaactg tatccgtcca agacgttccc ggctgacttt   900
ccggatcagg gccaggatct gtccaaattt gataccgccc cgagcctgga gattctgaaa   960
tccctgggcc gccctggctg gcgtagcatc gaggaatcta tcaaagatct ggtgggttcc  1020
gagaccgcct aa                                                      1032

SEQ ID NO: 48           moltype = AA   length = 343
FEATURE                 Location/Qualifiers
REGION                  1..343
                        note = ADH from Sporobolomyces salmonicolor
source                  1..343
                        mol_type = protein
                        organism = synthetic construct
SEQUENCE: 48
MAKIDNAVLP EGSLVLVTGA NGFVASHVVE QLLEHGYKVR GTARSASKLA NLQKRWDAKY    60
PGRFETAVVE DMLKQGAYDE VIKGAAGVAH IASVVSFSNK YDEVVTPAIG GTLNALRAAA   120
ATPSVKRFVL TSSTVSALIP KPNVEGIYLD EKSWNLESID KAKTLPESDP QKSLWVYAAS   180
KTEAELAAWK FMDENKPHFT LNAVLPNYTI GTIFDPETQS GSTSGWMMSL FNGEVSPALA   240
LMPPQYYVSA VDIGLLHLGC LVLPQIERRR VYGTAGTFDW NTVLATFRKL YPSKTFPADF   300
PDQGQDLSKF DTAPSLEILK SLGRPGWRSI EESIKDLVGS ETA                    343

SEQ ID NO: 49           moltype = DNA   length = 1050
FEATURE                 Location/Qualifiers
misc_feature            1..1050
                        note = ADH from Aspergillus flavus
source                  1..1050
                        mol_type = other DNA
                        organism = synthetic construct
SEQUENCE: 49
atgtctattc cggaaatgca atgggctcaa gtagcggagc agaaaggcgg tccgctgatt    60
tacaaacaga ttccggttcc gaaaccgggc ccggacgaaa tcctggtaaa agtgcgttac   120
tctggtgtgt gccacacgga tctgcacgcg ctgaaaggtg actggccact gcctgtgaaa   180
atgccactgg tgggtggcca tgagggcgcg gtgttgtcg tcgctcgtgg cgatctggtt    240
actgagttca aaattggtga ccatgctggc ctgaaatggc tgaacggtag ctgcctggca   300
tgcgagttct gtaaacaggc tgacgaaccg ctgtgcccta acgcgagcct gtctggttat   360
actgtagatg gtactttcca gcagtatgcc attggcaaag ccacccatgc gagcaagctg   420
ccgaaaaacg tgcctctgga tgccgtggca ccggttctgt gcgcgggcat taccgtatac   480
aagggcctga agaaagcgg tgttcgtcct ggccaaaccg ttgcgatcgt aggtgcgggt   540
ggtggtctgg gctccctggc gctgcagtac gcgaaagtca tgggtattcg cgtggtggcg   600
attgatggcg gtgaagagaa acaagccgatg tgtgaacagc tgggcgcaga agcctacgtt   660
gactttacca aaacgcaaga tctggtagca gatgttaagg ccgccacccc tgaaggtctg   720
ggcgcgcatg cggtaattct gctggcggtc gccgaaaaac catttcagca ggcggccgaa   780
tatgtcagcc gtggtacggt ggttgccatt ggtctgccgg cgggcgcact cctgcgcgcg   840
ccggtgttta acactgtggt tcgtatgatt aacattaagg gtagctacgt tggcaaccgc   900
caggacggcg ttgaggcagt ggacttcttc gcgcgcggcc tgatcaaagc gccgttcaaa   960
accgctcctc tgcaagatct gccgaaaatc ttcgaactga tggaacaagg taagattgca  1020
ggtcgctacg ttctggaaat cccggaatga                                   1050

SEQ ID NO: 50           moltype = AA   length = 349
FEATURE                 Location/Qualifiers
REGION                  1..349
                        note = ADH from Aspergillus flavus
source                  1..349
                        mol_type = protein
                        organism = synthetic construct
SEQUENCE: 50
MSIPEMQWAQ VAEQKGGPLI YKQIPVPKPG PDEILVKVRY SGVCHTDLHA LKGDWPLPVK    60
MPLVGGHEGA GVVVARGDLV TEFEIGDHAG LKWLNGSCLA CEFCKQADEP LCPNASLSGY   120
TVDGTFQQYA IGKATHASKL PKNVPLDAVA PVLCAGITVY KGLKESGVRP GQTVAIVGAG   180
GGLGSLALQY AKAMGIRVVA IDGGEEKQAM CEQLGAEAYV DFTKTQDLVA DVKAATPEGL   240
GAHAVILLAV AEKPFQQAAE YVSRGTVVAI GLPAGAFLRA PVFNTVVRMI NIKGSYVGNR   300
QDGVEAVDFF ARGLIKAPFK TAPLQDLPKI FELMEQGKIA GRYVLEIPE              349
```

| SEQ ID NO: 51 | moltype = DNA   length = 729 |
|---|---|
| FEATURE | Location/Qualifiers |
| misc_feature | 1..729 |
| | note = ADH from Oenococcus oeni |
| source | 1..729 |
| | mol_type = other DNA |
| | organism = synthetic construct |

SEQUENCE: 51
```
atgtttgatc gcctgaaggg taaggtggcg atcgtcaccg gcggtaatag cggtattggt   60
aaggcaatcg cggcagactt catcgccgag ggcgcgaaag tagtgattac cggtcgcaac  120
caagagaagg gtcgccagac tgcgctggaa atcgccggtg acattctgtt cattcagcag  180
gacgtgagcc aggaggcgga ctggcagaaa gttatctcca aaaccatcga aagttcggt   240
aagtttgata ttctggttaa caacgctggc gtcggcggtg tgggtaagcc actggcagaa  300
atgtccctgt ctgaattcaa ttggaccccaa tccattaatc tgtccggtaa cttcctgggt  360
attcacttcg cgctgaacaa aatgaccgaa cctggtagca ttattgacgt aagcagcgcg  420
gctggcctgc gtggttttcc gggcgcagcc gattatagcg cttccaaagg tggtacgcgt  480
ctgctgacgc gcgccgcggc gctggaagcg ctgcaaatgg gtaaaaagat ccgtgtaaac  540
tctattcacc caggttggat tgataccgat atcgtaccaa aagtatgcg tgagcaggtt   600
atcgcgatga cccctatgca tcacctgggc caaccgaaag atattgccaa gctggcgacg  660
tatctggcat ctgacgagtc cgagtatact acgggctccg aactggcagc cgacggcggt  720
ctgatggca                                                           729
```

| SEQ ID NO: 52 | moltype = AA   length = 243 |
|---|---|
| FEATURE | Location/Qualifiers |
| REGION | 1..243 |
| | note = ADH from Oenococcus oeni |
| source | 1..243 |
| | mol_type = protein |
| | organism = synthetic construct |

SEQUENCE: 52
```
MFDRLKGKVA IVTGGNSGIG KAIAADFIAE GAKVVITGRN QEKGRQTALE IAGDILFIQQ   60
DVSQEADWQK VISKTIEKFG KFDILVNNAG VGGVGKPLAE MSLSEFNWTQ SINLSGNFLG  120
IHFALNKMTE PGSIIDVSSA AGLRGFPGAA DYSASKGGTR LLTRAAALEA LQMGKKIRVN  180
SIHPGWIDTD IVPKDMREQV IAMTPMHHLG QPKDIAKLAT YLASDESEYT TGSELAADGG  240
LMA                                                                  243
```

| SEQ ID NO: 53 | moltype = DNA   length = 768 |
|---|---|
| FEATURE | Location/Qualifiers |
| misc_feature | 1..768 |
| | note = ADH from Ralstonia eutropha |
| source | 1..768 |
| | mol_type = other DNA |
| | organism = synthetic construct |

SEQUENCE: 53
```
atgcagggca aaattgcact ggttacgggc ggtgcgtctg gtatgggtct ggccttcacc   60
cgtcgcctgg cccaagaagg cgcacgtgtt tacttcaccg acattaacgg cgccgcgggt  120
cacgcgacgg aaagcgagct gcagggtgct ggtctcatga tcgtattcct gcgtcatgac  180
gtgacccagg aaaacgactg gctgcgcgtc ctgaacata ttggcgctgt tgacggtcgc   240
ctggatgtac tggtgaataa tgccggcatt gcgatttctc acaacattga cttgtact    300
actgaggatt tgatcgcac gctgaatgtt aacctgaagt ccgtgtttct gggctgcaaa   360
cacggtctgg ctctgatgaa acagaagggt ggcagcatca ttaacgttag ctctatcgcg  420
gcgatttgcg gcgaacctgt ggcgctggcg tatagcgcta gcaaagccgg cgtccgtttt  480
ctgagcaagt ctgttgccct gcattgtgcg gagaagggct acgccatccg tgttaacagc  540
ctgcacccgg gttacattga tacccgctg ctggcaggca gcaacgcggg tggctccctg   600
accgctgacg aggtaaccgc gagccgtgta cgtattggcg agaattcc gctgaaacgt    660
cgcggcaccc cggacgaagt tgcaggcgcg gttctgtacc tggctagcga tgaatccacc  720
tatgttactg gtactgagct ggtaattgat ggcggctacg catgtcat               768
```

| SEQ ID NO: 54 | moltype = AA   length = 256 |
|---|---|
| FEATURE | Location/Qualifiers |
| REGION | 1..256 |
| | note = ADH from Ralstonia eutropha |
| source | 1..256 |
| | mol_type = protein |
| | organism = synthetic construct |

SEQUENCE: 54
```
MQGKIALVTG GASGMGLAFT RRLAQEGARV YFTDINGAAG HATESELQGA GLAVVFLRHD   60
VTQENDWLRV LEHIGAVDGR LDVLVNNAGI AISHNIETCT TEDFDRTLNV NLKSVFLGCK  120
HGLALMKQKG GSIINVSSIT AICGEPVALA YSASKAGVRF LSKSVALHCA EKGYAIRVNS  180
LHPGYIDTPL LAGSNAGGSL TADEVTASRV RIGGEIPLKR RGTPDEVAGA VLYLASDEST  240
YVTGTELVID GGYACH                                                   256
```

| SEQ ID NO: 55 | moltype = DNA   length = 1056 |
|---|---|
| FEATURE | Location/Qualifiers |
| misc_feature | 1..1056 |
| | note = ADH from Thermoanaerobium brockii |
| source | 1..1056 |
| | mol_type = other DNA |
| | organism = synthetic construct |

-continued

```
SEQUENCE: 55
atgaaaggct tcgccatgct gagcatcggc aaagtgggtt ggattgaaaa agaaaaaccg    60
gcgccaggcc cgttcgatgc aattgtgcgc cctctggcag tagcgccgtg taccagcgat   120
attcatactg tgtttgaagg tgccattggc gagcgtcaca atatgattct gggccatgaa   180
gccgttggtg aagttgttga ggttggcagc gaagtgaagg atttcaaacc gggcgatcgc   240
gttgtcgttc cagcgattac cccggattgg cgcaccagcg aagtccagcg cggctaccat   300
cagcactctg gcggcatgct ggccggctgg aaattcagca atgtaaagga tggtgtgttc   360
ggtgaatttt tcacgttaa cgacgcagac atgaatctgg cgcacctgcc gaaagaaatc   420
ccgctggaag cagcggttat gattccggat atgatgacca cgggtttcca cggcgcagag   480
ctggcggaca ttgaactggg cgctacggta gccgtactgg gcatcggtcc ggtgggcctg   540
atggcagttg caggcgctaa gctgcgcggc gcaggtcgta ttattgccgt tggttctcgc   600
ccggtgtgtg tggacgccgc taagtattat ggtgcaacgg acattgtcaa ttacaaggac   660
ggcccaattg aatctcagat catgaacctg acggaaggta aaggcgttga cgccgcgatt   720
atcgctggcg gcaacgccga catcatggcg accgcagtta aaatcgtcaa gccaggtggt   780
actattgcta acgtcaacta cttcggcgaa ggtgaggtcc tgcctgtccc acgtctggaa   840
tggggttgcg gtatggcaca taaaaccatt aaggtggcc tgtgcccagg cggccgtctg   900
cgtatggaac gcctgatcga tctggtcttc tacaaacgcg tggatcctag caaactggtg   960
actcacgttt tccgcggctt tgataacatc gaaaaagctt ttatgctgat gaaagataaa  1020
ccgaaagatc tgattaaacc ggttgtcatc ctggct                            1056

SEQ ID NO: 56          moltype = AA  length = 352
FEATURE                Location/Qualifiers
REGION                 1..352
                       note = ADH from Thermoanaerobium brockii
source                 1..352
                       mol_type = protein
                       organism = synthetic construct
SEQUENCE: 56
MKGFAMLSIG KVGWIEKEKP APGPFDAIVR PLAVAPCTSD IHTVFEGAIG ERHNMILGHE    60
AVGEVVEVGS EVKDFKPGDR VVVPAITPDW RTSEVQRGYH QHSGGMLAGW KFSNVKDGVF   120
GEFFHVNDAD MNLAHLPKEI PLEAAVMIPD MMTTGFHGAE LADIELGATV AVLGIGPVGL   180
MAVAGAKLRG AGRIIAVGSR PVCVDAAKYY GATDIVNYKD GPIESQIMNL TEGKGVDAAI   240
IAGGNADIMA TAVKIVKPGG TIANVNYFGE GEVLPVPRLE WGCGMAHKTI KGGLCPGGRL   300
RMERLIDLVF YKRVDPSKLV THVFRGFDNI EKAFMLMKDK PKDLIKPVVI LA           352

SEQ ID NO: 57          moltype = DNA  length = 1125
FEATURE                Location/Qualifiers
misc_feature           1..1125
                       note = ADH from Horse Liver
source                 1..1125
                       mol_type = other DNA
                       organism = synthetic construct
SEQUENCE: 57
atgagcacag cagggaaagt aattaaatgc aaagcagctg tgctgtggga ggaaaagaaa    60
ccatttccca ttgaggaggt ggaggtcgca cctccgaagg cccatgaagt ccgtattaag   120
atggtggcca caggatctg tcgctcagat gaccacgtgg ttagtgggac cctggtcaca   180
cctctgcctg tgatcgcagg ccatgaggca gctggcattg tggagagcat cggggaaggc   240
gtcactacag tacgtccagg tgataaagtc atcccactgt ttactcctca gtgtgggaaa   300
tgccgtgttt gtaaacaccc tgaaggcaac ttctgcttga aaaatgatct gagcatgcct   360
cgtgggacca tgcaggatgg taccagccgt ttcctgcc gtgggaagcc tatccaccac   420
ttcctgggca ccagcacctt ctcccagtac accgtggtgg acgagatctc agtggccaac   480
atcgatgcgg cctcaccgct ggagaaagtc tgtctgattg gctgtgggtt ttctactggt   540
tatgggtctg cagtcaaggt tgccaagtc acccagggct ccaccgtgc cgtgtttggc   600
ctggggggg tgggcctgtc tgttatcatg ggctgtaaag cagccgggc ggcccgtatc   660
attggggtgg acatcaacaa agacaagttt gcaaaggcca aagaagtgg tgccactgag   720
tgtgtcaacc ctcaggacta caagaaacct atccaggagg tgctgacaga aatgagcaat   780
ggggcgtgg attttcatt gaagtcatt ggtcgtctgg acaccatggt gactgccttg   840
tcatgctgtc aagaagcata tggtgtgagc gtcatcgtag gggtacctcc tgattcccaa   900
aatctgctca tgaatcctat gttgctgctg agtgggcgta cctggaaagg ggctattttt   960
ggtggtttta agagtaaaga ttctgtccct aaactggtgg ccgattttg ggctaaaaag  1020
tttgcactgg atcctttaat cacccatgtt ttacctttg aaaaaattaa tgaagggttt  1080
gacctgctgc gctctgggga gagtatccgt accatcctga cgttt                 1125

SEQ ID NO: 58          moltype = AA  length = 375
FEATURE                Location/Qualifiers
REGION                 1..375
                       note = ADH from Horse Liver
source                 1..375
                       mol_type = protein
                       organism = synthetic construct
SEQUENCE: 58
MSTAGKVIKC KAAVLWEEKK PFSIEEVEVA PPKAHEVRIK MVATGICRSD DHVVSGTLVT    60
PLPVIAGHEA AGIVESIGEG VTTVRPGDKV IPLFTPQCGK CRVCKHPEGN FCLKNDLSMP   120
RGTMQDGTSR FTCRGKPIHH FLGTSTFSQY TVVDEISVAK IDAASPLEKV CLIGCGFSTG   180
YGSAVKVAKV TQGSTCAVFG LGGVGLSVIM GCKAAGAARI IGVDINKDKF AKAKEVGATE   240
CVNPQDYKKP IQEVLTEMSN GGVDFSFEVI GRLDTMVTAL SCCQEAYGVS VIVGVPPDSQ   300
NLSMNPMLLL SGRTWKGAIF GGFKSKDSVP KLVADFMAKK FALDPLITHV LPFEKINEGF   360
DLLRSGESIR TILTF                                                   375
```

```
SEQ ID NO: 59            moltype = DNA  length = 759
FEATURE                  Location/Qualifiers
source                   1..759
                         mol_type = other DNA
                         organism = Lactobacillus minor
SEQUENCE: 59
atgaccgatc ggttgaaggg gaaagtagca attgtaactg gcggtacctt gggaattggc   60
ttggcaatcg ctgataagtt tgttgaagaa ggcgcaaagg ttgttattac cggccgtcac  120
gctgatgtag gtgaaaaagc tgccagatca atcggcggca cagacgttat ccgttttgtc  180
caacacgatg cttctgatga aaccggctgg actaagttgt ttgatacgac tgaagaagca  240
tttggcccag ttaccacggt tgtcaacaat gccggaattg cggtcagcaa gagtgttgaa  300
gataccacaa ctgaagaatg cgcaagctg ctctcagtta acttggatgg tgtcttcttc    360
ggtacccgtc ttggaatcca acgtatgaag aataaaggac tcggagcatc aatcatcaat  420
atgtcatcta tcgaaggttt tgttggtgat ccagctctgg gtgcatacaa cgcttcaaaa  480
ggtgctgtca gaattatgtc taaatcagct gccttggatt gcgctttgaa ggactacgat  540
gttcgggtta acactgttca tccaggttat atcaagacac cattggttga cgatcttgaa  600
ggggcagaag aaatgatgtc acagcggacc aagacaccaa tgggtcatat cggtgaacct  660
aacgatatcg cttggatctg tgtttacctg gcatctgacg aatctaaatt tgccactggt  720
gcagaattcg ttgtcgacgg agggtacacc gcccaatag                          759

SEQ ID NO: 60            moltype = AA  length = 252
FEATURE                  Location/Qualifiers
source                   1..252
                         mol_type = protein
                         organism = Lactobacillus minor
SEQUENCE: 60
MTDRLKGKVA IVTGGTLGIG LAIADKFVEE GAKVVITGRH ADVGEKAARS IGGTDVIRFV    60
QHDASDETGW TKLFDTTEEA FGPVTTVVNN AGIAVSKSVE DTTTEEWRKL LSVNLDGVFF   120
GTRLGIQRMK NKGLGASIIN MSSIEGFVGD PALGAYNASK GAVRIMSKSA ALDCALKDYD   180
VRVNTVHPGY IKTPLVDDLE GAEEMMSQRT KTPMGHIGEP NDIAWICVYL ASDESKFATG   240
AEFVVDGGYT AQ                                                       252

SEQ ID NO: 61            moltype = AA  length = 252
FEATURE                  Location/Qualifiers
REGION                   1..252
                         note = Engineered Ketoreductase Sequence Formula with L.
                         kefir backbone Synthetic Construct
SITE                     7
                         note = MISC_FEATURE - Xaa is a nonpolar or constrained
                         residue
SITE                     40
                         note = MISC_FEATURE - Xaa is a constrained, hydrophilic, or
                         basic residue
SITE                     46
                         note = MISC_FEATURE - Xaa is a hydrophilic or basic residue
SITE                     60
                         note = MISC_FEATURE - Xaa is an aliphatic or non polar
                         residue
SITE                     64
                         note = MISC_FEATURE - Xaa is an aliphatic or non-polar
                         residue
SITE                     94
                         note = MISC_FEATURE - Xaa is an acidic residue
SITE                     96
                         note = MISC_FEATURE - Xaa is a polar, constrained, nonpolar
                         or aliphatic residue
SITE                     108
                         note = MISC_FEATURE - Xaa is a hydrophilic, polar, or
                         constrained residue
SITE                     109
                         note = MISC_FEATURE - Xaa is an acidic residue
SITE                     145
                         note = MISC_FEATURE - Xaa is a leucine or an aromatic
                         residue
SITE                     147
                         note = MISC_FEATURE - Xaa is a aromatic, nonpolar,
                         aliphatic, or hydrophobic residue
SITE                     152
                         note = MISC_FEATURE - Xaa is a polar residue
SITE                     153
                         note = MISC_FEATURE - Xaa is a polar, nonpolar, or
                         aliphatic residue
SITE                     157
                         note = MISC_FEATURE - Xaa is a polar residue
SITE                     190
                         note = MISC_FEATURE - Xaa is a cysteine or a constrained
                         residue
SITE                     195
                         note = MISC_FEATURE - Xaa is a nonpolar, aliphatic, or
```

```
                              basic residue
SITE                          196
                              note = MISC_FEATURE - Xaa is a non polar or aliphatic
                              residue
SITE                          198
                              note = MISC_FEATURE - Xaa is an acidic, polar, or
                              hydrophilic residue
SITE                          199
                              note = MISC_FEATURE - Xaa is an acidic, basic, hydrophilic,
                              aliphatic or nonpolar residue
SITE                          206
                              note = MISC_FEATURE - Xaa is a nonpolar, aromatic, or
                              hydrophobic residue
SITE                          226
                              note = MISC_FEATURE - Xaa is a non polar or aliphatic
                              residue
SITE                          233
                              note = MISC_FEATURE - Xaa is an acidic, nonpolar or
                              aliphatic residue
SITE                          245
                              note = MISC_FEATURE - Xaa is a non polar or aliphatic
                              residue
SITE                          249
                              note = MISC_FEATURE - Xaa is a nonpolar or aromatic residue
source                        1..252
                              mol_type = protein
                              organism = synthetic construct
SEQUENCE: 61
MTDRLKXKVA IVTGGTLGIG LAIADKFVEE GAKVVITGRX ADVGEXAAKS IGGTDVIRFX    60
QHDXSDEAGW TKLFDTTEEA FGPVTTVVNN AGIXVXKSVE DTTTEEWXXL LSVNLDGVFF   120
GTRLGIQRMK NKGLGASIIN MSSIXGXVGD PXXGAYXASK GAVRIMSKSA ALDCALKDYD   180
VRVNTVHPGX IKTPXXDXXE GAEEMXSQRT KTPMGHIGEP NDIAWXCVYL ASXESKFATG   240
AEFVXDGGXT AQ                                                      252

SEQ ID NO: 62                 moltype = AA  length = 252
FEATURE                       Location/Qualifiers
REGION                        1..252
                              note = Engineered Ketoreductase Sequence Formula with L.
                              brevis backbone Synthetic Construct
SITE                          7
                              note = MISC_FEATURE - Xaa is a nonpolar or constrained
                              residue
SITE                          40
                              note = MISC_FEATURE - Xaa is a constrained, hydrophilic, or
                              basic residue
SITE                          46
                              note = MISC_FEATURE - Xaa is a hydrophilic or basic residue
SITE                          60
                              note = MISC_FEATURE - Xaa is an aliphatic or non polar
                              residue
SITE                          64
                              note = MISC_FEATURE - Xaa is an aliphatic or non-polar
                              residue
SITE                          94
                              note = MISC_FEATURE - Xaa is an acidic residue
SITE                          96
                              note = MISC_FEATURE - Xaa is a polar, constrained, nonpolar
                              or aliphatic residue
SITE                          108
                              note = MISC_FEATURE - Xaa is a hydrophilic, polar, or
                              constrained residue
SITE                          109
                              note = MISC_FEATURE - Xaa is an acidic residue
SITE                          145
                              note = MISC_FEATURE - Xaa is a leucine or an aromatic
                              residue
SITE                          147
                              note = MISC_FEATURE - Xaa is a aromatic, nonpolar,
                              aliphatic, or hydrophobic residue
SITE                          152
                              note = MISC_FEATURE - Xaa is a polar residue
SITE                          153
                              note = MISC_FEATURE - Xaa is a polar, nonpolar, or
                              aliphatic residue
SITE                          157
                              note = MISC_FEATURE - Xaa is a polar residue
SITE                          190
                              note = MISC_FEATURE - Xaa is a cysteine or a constrained
                              residue
```

| | |
|---|---|
| SITE | 195 |
| | note = MISC_FEATURE - Xaa is a nonpolar, aliphatic, or basic residue |
| SITE | 196 |
| | note = MISC_FEATURE - Xaa is a non polar or aliphatic residue |
| SITE | 198 |
| | note = MISC_FEATURE - Xaa is an acidic, polar, or hydrophilic residue |
| SITE | 199 |
| | note = MISC_FEATURE - Xaa is an acidic, basic, hydrophilic, aliphatic or nonpolar residue |
| SITE | 206 |
| | note = MISC_FEATURE - Xaa is a nonpolar, aromatic, or hydrophobic residue |
| SITE | 226 |
| | note = MISC_FEATURE - Xaa is a non polar or aliphatic residue |
| SITE | 233 |
| | note = MISC_FEATURE - Xaa is an acidic, nonpolar or aliphatic residue |
| SITE | 245 |
| | note = MISC_FEATURE - Xaa is a non polar or aliphatic residue |
| SITE | 249 |
| | note = MISC_FEATURE - Xaa is a nonpolar or aromatic residue |
| source | 1..252 |
| | mol_type = protein |
| | organism = synthetic construct |

SEQUENCE: 62

```
MSNRLDXKVA IITGGTLGIG LAIATKFVEE GAKVMITGRX SDVGEXAAKS VGTPDQIQFX   60
QHDXSDEDGW TKLFDATEKA FGPVSTLVNN AGIXVXKSVE ETTTAEWXXL LAVNLDGVFF  120
GTRLGIQRMK NKGLGASIIN MSSIXGXVGD PXXGAYXASK GAVRIMSKSA ALDCALKDYD  180
VRVNTVHPGX IKTPXXDXXP GAEEAXSQRT KTPMGHIGEP NDIAYXCVYL ASXESKFATG  240
SEFVXDGGXT AQ                                                     252
```

| | |
|---|---|
| SEQ ID NO: 63 | moltype = AA  length = 252 |
| FEATURE | Location/Qualifiers |
| REGION | 1..252 |
| | note = Engineered Ketoreductase Sequence Formula with L. minor backbone Synthetic Construct |
| SITE | 7 |
| | note = MISC_FEATURE - Xaa is a nonpolar or constrained residue |
| SITE | 40 |
| | note = MISC_FEATURE - Xaa is a constrained, hydrophilic, or basic residue |
| SITE | 46 |
| | note = MISC_FEATURE - Xaa is a hydrophilic or basic residue |
| SITE | 60 |
| | note = MISC_FEATURE - Xaa is an aliphatic or non polar residue |
| SITE | 64 |
| | note = MISC_FEATURE - Xaa is an aliphatic or non-polar residue |
| SITE | 94 |
| | note = MISC_FEATURE - Xaa is an acidic residue |
| SITE | 96 |
| | note = MISC_FEATURE - Xaa is a polar, constrained, nonpolar or aliphatic residue |
| SITE | 108 |
| | note = MISC_FEATURE - Xaa is a hydrophilic, polar, or constrained residue |
| SITE | 109 |
| | note = MISC_FEATURE - Xaa is an acidic residue |
| SITE | 145 |
| | note = MISC_FEATURE - Xaa is a leucine or an aromatic residue |
| SITE | 147 |
| | note = MISC_FEATURE - Xaa is a aromatic, nonpolar, aliphatic, or hydrophobic residue |
| SITE | 152 |
| | note = MISC_FEATURE - Xaa is a polar residue |
| SITE | 153 |
| | note = MISC_FEATURE - Xaa is a polar, nonpolar, or aliphatic residue |
| SITE | 157 |
| | note = MISC_FEATURE - Xaa is a polar residue |
| SITE | 190 |

```
                           note = MISC_FEATURE - Xaa is a cysteine or a constrained
                           residue
SITE                       195
                           note = MISC_FEATURE - Xaa is a nonpolar, aliphatic, or
                           basic residue
SITE                       196
                           note = MISC_FEATURE - Xaa is a non polar or aliphatic
                           residue
SITE                       198
                           note = MISC_FEATURE - Xaa is an acidic, polar, or
                           hydrophilic residue
SITE                       199
                           note = MISC_FEATURE - Xaa is an acidic, basic, hydrophilic,
                           aliphatic or nonpolar residue
SITE                       206
                           note = MISC_FEATURE - Xaa is a nonpolar, aromatic, or
                           hydrophobic residue
SITE                       226
                           note = MISC_FEATURE - Xaa is a non polar or aliphatic
                           residue
SITE                       233
                           note = MISC_FEATURE - Xaa is an acidic, nonpolar or
                           aliphatic residue
SITE                       245
                           note = MISC_FEATURE - Xaa is a non polar or aliphatic
                           residue
SITE                       249
                           note = MISC_FEATURE - Xaa is a nonpolar or aromatic residue
source                     1..252
                           mol_type = protein
                           organism = synthetic construct
SEQUENCE: 63
MTDRLKXKVA IVTGGTLGIG LAIADKFVEE GAKVVITGRX ADVGEXAARS IGGTDVIRFX    60
QHDXSDETGW TKLFDTTEEA FGPVTTVVNN AGIXVXKSVE DTTTEEWXXL LSVNLDGVFF   120
GTRLGIQRMK NKGLGASIIN MSSIXGXVGD PXXGAYXASK GAVRIMSKSA ALDCALKDYD   180
VRVNTVHPGX IKTPXXDXXE GAEEMXSQRT KTPMGHIGEP NDIAWXCVYL ASXESKFATG   240
AEFVXDGGXT AQ                                                      252
```

ENGINEERED KETOREDUCTASE POLYPEPTIDES

CROSS REFERENCE TO RELATED APPLICATIONS

The present application is a Continuation of co-pending U.S. patent application Ser. No. 16/932,084, filed Jul. 17, 2020, which is a Continuation of U.S. patent application Ser. No. 15/982,291, filed May 17, 2018, now U.S. Pat. No. 10,752,926, which is a Divisional of U.S. patent application Ser. No. 15/489,946, filed Apr. 18, 2017, now U.S. Pat. No. 10,006,069, which is a Division of U.S. patent application Ser. No. 14/954,564, filed Nov. 30, 2015, now U.S. Pat. No. 9,657,320, which is a Continuation of U.S. patent application Ser. No. 14/503,758, filed Oct. 1, 2014, now U.S. Pat. No. 9,228,213, which is a Continuation of U.S. patent application Ser. No. 13/610,166, filed Sep. 11, 2012, now U.S. Pat. No. 8,877,475, which claims priority pursuant to 35 U.S.C. § 120 to U.S. patent application Ser. No. 12/549,293, filed Aug. 27, 2009, now U.S. Pat. No. 8,288,141, and which claims the benefit, pursuant 35 U.S.C. § 119(e), of U.S. Prov. Pat. Appln. Ser. No. 61/092,331, filed Aug. 27, 2008, each of which is hereby incorporated herein by reference in its entirety for all purposes.

TECHNICAL FIELD

The present disclosure relates to engineered ketoreductase polypeptides and uses thereof for the preparation of 3-aryl-3-hydroxypropanamines from the corresponding 3-aryl-3-ketopropanamines.

REFERENCE TO SEQUENCE LISTING, TABLE OR COMPUTER PROGRAM

The Sequence Listing concurrently submitted herewith under 37 C.F.R. § 1.821 in a computer readable form (CRF) via Patent Center as file name "CX2-030USD1C4 ST26.xml" is herein incorporated by reference. This electronic copy of the Sequence Listing was created on Oct. 24, 2022, with a file size of 141 kilobytes. This electronic copy of the Sequence Listing is identical to the substitute Sequence Listing submitted in the parent application on Mar. 11, 2010, and identical except for minor formatting corrections to the paper copy of the Sequence Listing filed with the parent application on Aug. 27, 2009.

BACKGROUND

Enzymes belonging to the ketoreductase (KRED) or carbonyl reductase class (EC1.1.1.184) are useful for the synthesis of optically active alcohols from the corresponding prostereoisomeric ketone substrates and by stereospecific reduction of corresponding racemic aldehyde and ketone substrates. KREDs typically convert a ketone or aldehyde substrate to the corresponding alcohol product, but may also catalyze the reverse reaction, oxidation (dehydrogenation) of an alcohol substrate to the corresponding ketone/aldehyde product. The reduction of ketones and aldehydes and the oxidation of alcohols by enzymes such as KRED requires a co-factor, most commonly reduced nicotinamide adenine dinucleotide (NADH) or reduced nicotinamide adenine dinucleotide phosphate (NADPH), and nicotinamide adenine dinucleotide (NAD) or nicotinamide adenine dinucleotide phosphate (NADP) for the oxidation reaction. NADH and NADPH serve as electron donors, while NAD and NADP serve as electron acceptors. It is frequently observed that ketoreductases and alcohol dehydrogenases accept either the phosphorylated or the non-phosphorylated co-factor (in its oxidized and reduced state).

KRED enzymes can be found in a wide range of bacteria and yeasts (for reviews: Kraus and Waldman, Enzyme catalysis in organic synthesis Vols. 1&2.VCH Weinheim 1995; Faber, K., Biotransformations in organic chemistry, 4th Ed. Springer, Berlin Heidelberg New York. 2000; Hummel and Kula Eur. J. Biochem. 1989 184:1-13). Several KRED gene and enzyme sequences have been reported, e.g., *Candida magnoliae* (Genbank Acc. No. JC7338; GI: 11360538) *Candida parapsilosis* (Genbank Acc. No. BAA24528.1; GI:2815409), *Sporobolomyces salmonicolor* (Genbank Acc. No. AF160799; GI:6539734).

In order to circumvent many chemical synthetic procedures for the production of key compounds, ketoreductases are being increasingly employed for the enzymatic conversion of different keto and aldehyde substrates to chiral alcohol products. These applications can employ whole cells expressing the ketoreductase for biocatalytic reductions, or purified enzymes in those instances where presence of multiple ketoreductases in whole cells would adversely affect the stereopurity and yield of the desired product. For in vitro applications, a co-factor (NADH or NADPH) regenerating enzyme such as glucose dehydrogenase (GDH), formate dehydrogenase etc. can be used in conjunction with the ketoreductase. Examples using ketoreductases to generate useful chemical compounds include asymmetric reduction of 4-chloroacetoacetate esters (Zhou, *J. Am. Chem. Soc.* 1983 105:5925-5926; Santaniello, *J. Chem. Res.* (S) 1984:132-133; U.S. Pat. Nos. 5,559,030; 5,700,670 and 5,891,685), reduction of dioxocarboxylic acids (e.g., U.S. Pat. No. 6,399,339), reduction of tert-butyl (S) chloro-5-hydroxy-3-oxohexanoate (e.g., U.S. Pat. No. 6,645,746 and WO 01/40450), reduction pyrrolotriazine-based compounds (e.g., US application No. 2006/0286646); reduction of substituted acetophenones (e.g., U.S. Pat. No. 6,800,477); and reduction of ketothiolanes (WO 2005/054491).

It is desirable to identify other ketoreductase enzymes that can be used to carry out conversion of various keto substrates to their corresponding chiral alcohol products.

SUMMARY

The present disclosure provides ketoreductase polypeptides having the ability to reduce a 3-aryl-3-ketopropanamine to a 3-aryl-3-hydroxypropanamine, polynucleotides encoding such polypeptides, and methods for making and using the polypeptides. Ketoreductase polypeptides of the present invention are particularly useful for preparing intermediates in the synthesis of the drug, Duloxetine (i.e., (3S)—N-methyl-3-naphthalen-1-yloxy-3-thiophen-2-yl-propan-1-amine). Exemplary substrates include, for example, N,N-dimethyl-3-keto-3-(2-thienyl)-1-propanamine ("DMAK"; "the dimethyl amino ketone substrate" or the "dimethyl substrate") and N-methyl-3-keto-3-(2-thienyl)-1-propanamine ("MMAK"; "the monomethyl amino ketone substrate" or the "monomethyl substrate") which are reduced to (S)—N,N-dimethyl-3-hydroxy-3-(2-thienyl)-1-propanamine ("(S)-DMAA"; "the dimethyl amino alcohol product" or the "dimethyl product") and (S)—N-methyl-3-hydroxy-3-(2-thienyl)-1-propanamine ("(S)-MMAA"; "the monomethyl amino alcohol product" or the "monomethyl product"), respectively. The ketoreductase polypeptides of the present invention exhibit the ability to reduce the substrate N-methyl-3-keto-3-(2-thienyl)-1-propanamine to product (S)—N-methyl-3-hydroxy-3-(2-thienyl)-1-propanamine with particularly high stereoselectivity.

In one aspect, the ketoreductase polypeptides described herein have an amino acid sequence that has one or more amino acid differences as compared to a reference wild-type ketoreductase or an engineered ketoreductase sequence, where the differences result in an improved property of the enzyme in carrying out the conversion of the specific keto substrate to the alcohol product. Generally, the engineered ketoreductase polypeptides have an improved property as compared to the naturally-occurring wild-type ketoreductase enzymes obtained from *Lactobacillus kefir* ("*L. kefir*"; SEQ ID NO:2), *Lactobacillus brevis* ("*L. brevis*"; SEQ ID NO:4), or *Lactobacillus minor* ("*L. minor*," SEQ ID NO:60), or compared to another engineered polypeptide, such as SEQ ID NO:6. Improvements in enzyme property can include increases in enzyme activity, stereoselectivity, stereospecificity, thermostability, solvent stability, or reduced product inhibition. In the present disclosure, the ketoreductase polypeptides have, as compared to the amino acid sequence of SEQ ID NO:2, 4 or 60, at least the following features: (1) the residue corresponding to position 94 is an acidic residue, (2) the residue corresponding to position 145 is an aromatic residue or leucine, and (3) the residue corresponding to position 190 is a cysteine or a constrained residue. In some embodiments, the polypeptides of the disclosure have, as compared to the sequences of SEQ ID NO:2, 4 and 60, at least the following features: (1) the residue corresponding to position 94 is aspartic acid, (2) the residue corresponding to position 145 is tyrosine, tryptophan, phenylalanine, or leucine, particularly phenylalanine or leucine and (3) the residue corresponding to position 190 is cysteine or proline. In some embodiments, the ketoreductase polypeptides of the disclosure have, as compared to the sequences of SEQ ID NO:2, 4 or 60, at least the following features: (1) residue corresponding to position 94 is aspartic acid, (2) residue corresponding to position 145 is phenylalanine, and (3) residue corresponding to position 190 is proline.

In some embodiments, the engineered ketoreductases can possess a single improved property, or they can possess two or more improved properties, in any combination(s). For example, the engineered ketoreductase polypeptide can have increased enzymatic activity as compared to the wild-type ketoreductase enzyme for reducing the monomethyl substrate to the corresponding product. Improvements in enzymatic activity can be measured by comparing the specific activity of the ketoreductase polypeptide with that of the wild-type ketoreductase enzyme using standard enzyme assays. The amount of the improvement can range from 1.5 times the enzymatic activity of the corresponding wild-type or that of a reference ketoreductase enzyme, to as much as 2, 5, 10, 15 times or more improvement of the enzymatic activity. In specific embodiments, the engineered ketoreductase enzyme exhibits improved enzymatic activity that is at least 1.5-times, 2 times, 3 times, 4 times, 5 times, 10 times, 15 times, 20 times, 25 times, 30 times, 50 times or more than that of the wild-type or of the reference ketoreductase enzyme. Improvements in enzyme activity also include increases in stereoselectivity, stereospecificity, thermostability, solvent stability, or reduced product inhibition.

In some embodiments, the ketoreductase polypeptides herein are improved as compared to SEQ ID NO:2 or SEQ ID NO:6 with respect to their rate of enzymatic activity, i.e., their rate of converting the monomethyl substrate to the corresponding product. In some embodiments, the ketoreductase polypeptides are capable of converting the monomethyl substrate to product at a rate that is at least 1.5 times, 2 times, 5 times, 10 times, or 15 times the rate displayed by the ketoreductase of SEQ ID NO:2 or SEQ ID NO:6.

In some embodiments, the ketoreductase polypeptides are capable of converting the substrate N-methyl-3-keto-3-(2-thienyl)-1-propanamine to (S)—N-methyl-3-hydroxy-3-(2-thienyl)-1-propanamine at a rate that is improved over a reference polypeptide having the amino acid sequence of SEQ ID NO:6. In some embodiments, such ketoreductase polypeptides are also capable of converting the monomethyl substrate to product with a percent stereomeric excess of at least about 95%. In some embodiments, such ketoreductase polypeptides are also capable of converting the monomethyl substrate to product with a percent stereomeric excess of at least about 99%. Exemplary polypeptides with such properties include, but are not limited to, polypeptides which comprise amino acid sequences corresponding to SEQ ID NO: 8, 10, 12, 14, 16, 18, 20, 22, 24, 26, 28, 30, and 32. Because the reference polypeptide having the amino acid sequence of SEQ ID NO:6 is capable of converting the monomethyl substrate to product at a rate improved over that of the wild-type enzyme of SEQ ID NO:2, the polypeptides herein that are improved over SEQ ID NO:6 are also improved over wild-type.

In some embodiments, the ketoreductase polypeptides of the disclosure are capable of converting the substrate N-methyl-3-keto-3-(2-thienyl)-1-propanamine to the product (S)—N-methyl-3-hydroxy-3-(2-thienyl)-1-propanamine, with a percent stereomeric excess of at least about 99% and at a rate that is at least 5-10 times the rate of a reference polypeptide having the amino acid sequence of SEQ ID NO:6. Exemplary polypeptides with such properties include, but are not limited to, polypeptides which comprise an amino acid sequence corresponding to SEQ ID NO: 8, 10, and 20.

In some embodiments, the ketoreductase polypeptides of the disclosure are capable of converting the substrate N-methyl-3-keto-3-(2-thienyl)-1-propanamine to the product (S)—N-methyl-3-hydroxy-3-(2-thienyl)-1-propanamine, with a percent stereomeric excess of at least about 99% and at a rate that is at least 10-15 times the rate of a reference polypeptide having the amino acid sequence of SEQ ID NO:6. Exemplary polypeptides with such properties include, but are not limited to, polypeptides which comprise an amino acid sequence corresponding to SEQ ID NO: 12, 14, 16, 18, and 22.

In some embodiments, the ketoreductase polypeptides are capable of converting the substrate N-methyl-3-keto-3-(2-thienyl)-1-propanamine to the product (S)—N-methyl-3-hydroxy-3-(2-thienyl)-1-propanamine, with a percent stereomeric excess of at least about 99% and at a rate that is at least 15 times the rate of a reference polypeptide having the amino acid sequence of SEQ ID NO:6. Exemplary polypeptides with such properties include, but are not limited to, polypeptides which comprise amino acid sequences corresponding to SEQ ID NO: 24, 26, 28, 30, and 32.

In some embodiments, the ketoreductase polypeptides of the disclosure are capable of converting at least about 95% of the substrate N-methyl-3-keto-3-(2-thienyl)-1-propanamine to the product (S)—N-methyl-3-hydroxy-3-(2-thienyl)-1-propanamine in less than about 24 hours when carried out with greater than about 100 g/L of substrate and less than about 5 g/L of the polypeptide. Exemplary polypeptides that have this capability include, but are not limited to, polypeptides which comprise amino acid sequences corresponding to SEQ ID NO: 24, 26, 28, 30, and 32.

In some embodiments, the ketoreductase polypeptides can highly stereoselectively reduce the substrate N-methyl-3- keto-3-(2-thienyl)-1-propanamine to the product (S)—N-methyl-3-hydroxy-3-(2-thienyl)-1-propanamine in greater than about 99%, 99.1%, 99.2%, 99.3%, 99.4%, 99.5%, 99.6%, 99.7%, 99.8% or 99.9% stereomeric excess. Exemplary ketoreductase polypeptides with such high stereoselectivity include, but are not limited to, the polypeptides comprising the amino acid sequences corresponding to SEQ ID NO: 8, 10, 12, 14, 16, 18, 20, 22, 24, 26, 28, 30, and 32.

In some embodiments, an improved ketoreductase polypeptide comprises an amino acid sequence that corresponds to the sequence formula provided in SEQ ID NO:61 or SEQ ID NO:62 or SEQ ID NO:63, or a region thereof, such as residues 90-211. SEQ ID NO:61 is based on the wild-type amino acid sequence of the *Lactobacillus kefir* ketoreductase (SEQ ID NO:2); SEQ ID NO:62 is based on the wild-type amino acid sequence of the *Lactobacillus brevis* ketoreductase (SEQ ID NO:4); and SEQ ID NO:63 is based on the wild-type amino acid sequence of the *Lactobacillus minor* ketoreductase (SEQ ID NO:60). SEQ ID NOs:61, 62 and 63 specify that (1) residue 94 is an acidic amino acid, (2) residue 145 is an aromatic amino acid or leucine, and (3) residue 190 is a cysteine or a constrained residue.

In some embodiments, an improved ketoreductase polypeptide of the disclosure is based on the sequence formula of SEQ ID NO:61, 62 or 63 and can comprise an amino acid sequence that is at least about 85%, 86%, 87%, 88%, 89%, 90%, 91%, 92%, 93%, 94%, 95%, 96%, 97%, 98%, or 99% identical to reference sequence based on SEQ ID NO:2, 4 or 60, with the proviso that (1) the amino acid residue corresponding to position 94 is an acidic amino acid, (2) the amino acid residue corresponding to position 145 is aromatic amino acid or leucine, and (3) the amino acid residue corresponding to position 190 is cysteine or proline, wherein the ketoreductase polypeptides have at least the specified provisos. In some embodiments, the ketoreductase polypeptides have the specified sequence identity to a reference sequence based on SEQ ID NO:2, 4, or 60, or a region there of, such as residues 90-211, with the proviso that (1) the amino acid residue corresponding to position 94 is aspartic acid, (2) the amino acid residue corresponding to position 145 is tyrosine, phenylalanine or leucine, particularly phenylalanine or leucine, and (3) the amino acid residue corresponding to position 190 is cysteine or proline, wherein the ketoreductase polypeptides have at least the specified provisos. In some embodiments, the ketoreductase polypeptides have the specified sequence identity to a reference sequence based on SEQ ID NO:2, 4, or 60, or a region there of, such as residues 90-211, with the proviso that (1) the amino acid residue corresponding to position 94 is aspartic acid, (2) the amino acid residue corresponding to position 145 is phenylalanine or leucine, and (3) the amino acid residue corresponding to position 190 is proline, wherein the ketoreductase polypeptides have the specified provisos. In some embodiments, the ketoreductase polypeptides can additionally have one or more amino acid residue differences as compared to the reference sequences above. These differences can be amino acid insertions, deletions, substitutions, or any combination of such changes.

In some embodiments, the amino acid sequence differences can comprise non-conservative, conservative, as well as a combination of non-conservative and conservative amino acid substitutions. Various amino acid residue positions where such changes can be made are described herein. In some embodiments, an improved ketoreductase polypeptide of the disclosure is based on the sequence formula of SEQ ID NO:89, 90 or 91 and can comprise a region or domain that is at least about 85%, 86%, 87%, 88%, 89%, 90%, 91%, 92%, 93%, 94%, 95%, 96%, 97%, 98%, or 99% identical to a region or domain thereof, such as residues 90-211 of reference sequence based on SEQ ID NO:2, 4 or 60, with the proviso that (1) the amino acid residue corresponding to position 94 is an acidic amino acid, (2) the amino acid residue corresponding to position 145 is aromatic amino acid or leucine, and (3) the amino acid residue corresponding to position 190 is cysteine or proline, wherein the ketoreductase polypeptides have at least the specified provisos. In some embodiments, the ketoreductase polypeptides have the specified sequence identity to a reference sequence based on SEQ ID NO:2, 4, or 60, or a region thereof, such as residues 90-211, with the proviso that (1) the amino acid residue corresponding to position 94 is aspartic acid, (2) the amino acid residue corresponding to position 145 is tyrosine, phenylalanine or leucine, and (3) the amino acid residue corresponding to position 190 is cysteine or proline, and wherein the ketoreductase polypeptides have at least the specified provisos. In some embodiments, the ketoreductase polypeptides have the specified sequence identity to a reference sequence based on SEQ ID NO:2, 4, or 60, or a region there of, such as residues 90-211, with the proviso that (1) the amino acid residue corresponding to position 94 is aspartic acid, (2) the amino acid residue corresponding to position 145 is phenylalanine, and (3) the amino acid residue corresponding to position 190 is proline, and wherein the ketoreductase polypeptides have at least the specified provisos. In some embodiments, the ketoreductase polypeptides can additionally have one or more amino acid residue differences in the defined region. In some embodiments, the amino acid sequence differences can comprise non-conservative, conservative, as well as a combination of non-conservative and conservative amino acid substitutions. Various amino acid residue positions where such changes can be made are described herein.

In some embodiments, an improved ketoreductase comprises an amino acid sequence that is at least about 85%, 86%, 87%, 88%, 89%, 90%, 91%, 92%, 93%, 94%, 95%, 96%, 97%, 98%, or 99% identical to the amino acid sequence corresponding to SEQ ID NO: 8, 10, 12, 14, 16, 18, 20, 22, 24, 26, 28, 30, and 32, wherein the improved ketoreductase polypeptide amino acid sequence includes any one set of the specified amino acid substitution combinations presented in Table 2. In some embodiments, these ketoreductase polypeptides can have from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, or about 1-35 mutations (i.e., differences) at other amino acid residues. In some embodiments, the number of mutations can be 1, 2, 3, 4, 5, 6, 7, 8, 9, 10, 11, 12, 14, 15, 16, 18, 20, 22, 24, 26, 30, 35 or about 40 amino acid residues. In some embodiments, the mutations are conservative mutations.

In another aspect, the present disclosure provides polynucleotides encoding the engineered ketoreductases described herein or polynucleotides that hybridize to such polynucleotides under highly stringent conditions. The polynucleotide can include promoters and other regulatory elements useful for expression of the encoded engineered ketoreductase, and can utilize codons optimized for specific desired expression systems. Exemplary polynucleotides include, but are not limited to, SEQ ID NO: 7, 9, 11, 13, 15, 17, 19, 21, 23, 25, 27, 29, and 31. Exemplary polynucleotides also include polynucleotides encoding polypeptides that correspond to the sequence formula of SEQ ID NO:61, 62 or 63.

In another aspect, the present disclosure provides host cells comprising the polynucleotides and/or expression vectors described herein. The host cells may be *L. kefir* or *L. brevis* or *L. minor*, or they may be a different organism, such as *E. coli*. The host cells can be used for the expression and isolation of the engineered ketoreductase enzymes described herein, or, alternatively, they can be used directly for the conversion of the substrate to the stereoisomeric product.

Whether carrying out the method with whole cells, cell extracts or purified ketoreductase enzymes, a single ketoreductase enzyme may be used or, alternatively, mixtures of two or more ketoreductase enzymes may be used.

The ketoreductase enzymes described herein are useful for catalyzing the reduction reaction of the keto group in the 3-aryl-3-ketopropanamine having the structural formula (I):

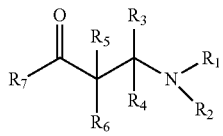

(I)

to the corresponding (S)-3-aryl-3-hydroxypropanamine having the structural formula (II):

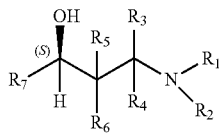

(II)

wherein for (I) and (II), $R_1$ and $R_2$ are each independently selected from the group consisting of hydrogen, an optionally substituted lower alkyl, an optionally substituted cycloalkyl, an optionally substituted aryl, or alternatively, where $R_1$ and $R_2$ together form an optionally substituted cycloalkyl or an optionally substituted cycloaryl having 3-7 carbon atoms; $R_3$, $R_4$, $R_5$, and $R_6$ are each independently selected from the group consisting of hydrogen and an optionally substituted lower alkyl; and $R_7$ is an optionally substituted aryl.

The ketoreductase polypeptides described herein are particularly capable of reducing the substrate N-methyl-3-keto-3-(2-thienyl)-1-propanamine (III):

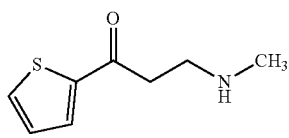

(III)

to the corresponding stereoisomeric alcohol product of structural formula (II), (S)—N-methyl-3-hydroxy-3-(2-thienyl)-1-propanamine ("the monomethyl product"):

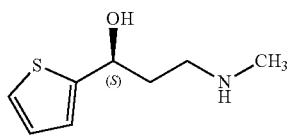

(IV)

with high stereoselectivity.

In some embodiments, the invention provides a method for reducing the substrate having the chemical formula (I) to the corresponding product of structural formula (II), comprising contacting or incubating the substrate with a ketoreductase polypeptide described herein under reaction conditions suitable for reducing or converting the substrate to the product. For example, in some embodiments of this method, the ketoreductase polypeptides have, as compared to the L. kefir or L. brevis or L. minor KRED sequences of SEQ ID NO: 2, 4 or 60, at least the following features: (1) residue corresponding to X94 is an acidic amino acid, (2) residue corresponding to X145 is an aromatic amino acid or leucine, and (3) residue corresponding to X190 is a cysteine or a constrained amino acid. In some embodiments of this method, the ketoreductase polypeptide used in the method can have, as compared to the wild-type L. kefir or L. brevis or L. minor KRED sequences of SEQ ID NO: 2, 4 and 60, respectively, at least the following features: (1) residue corresponding to residue X94 is glycine, (2) residue corresponding to position 145 tyrosine, tryptophan, phenylalanine, or leucine, particularly phenylalanine or leucine, and (3) residue corresponding to X190 is cysteine or proline, particularly proline. In some embodiments of this method, the ketoreductase polypeptides have, as compared to the L. kefir or L. brevis or L. minor KRED sequences of SEQ ID NO: 2, 4 or 60, the following features: (1) residue corresponding to X94 is glycine, (2) residue corresponding to X145 phenylalanine and (3) residue corresponding to X190 is proline.

In some embodiments of this method for reducing the substrate to the product, the monomethyl substrate (III) is reduced to the monomethyl product (IV) in greater than about 99% stereomeric excess, wherein the ketoreductase polypeptide comprises a sequence that corresponds to SEQ ID NO: 8, 10, 12, 14, 16, 18, 20, 22, 24, 26, 28, 30, or 32.

In some embodiments of this method for reducing the monomethyl substrate (III) to the monomethyl product (IV), at least about 95% of the substrate is converted to the product in less than about 24 hours when carried out with greater than about 100 g/L of substrate and less than about 5 g/L of the polypeptide, wherein the polypeptide comprises an amino acid sequence corresponding to SEQ ID NO: 24, 26, 28, 30, or 32.

In some embodiments of this method for reducing the monomethyl substrate (III) to the monomethyl product (IV), at least about 10-20% of 1 g/L substrate is converted to the product in less than about 24 hours with about 10 g/L of the polypeptide, wherein the polypeptide comprises an amino acid sequence corresponding to 12, 14, 16, 18, 22, 24, 26, 28, 30, or 32.

In some embodiments, the method for reducing or converting the compound N-methyl-3-keto-3-(2-thienyl)-1-propanamine to the product (S)—N-methyl-3-hydroxy-3-(2-thienyl)-1-propanamine is carried out at a pH of from about 5 to about 8.0. In some embodiments, the contacting is carried out a pH of about 6.5.

In some embodiments, the methods relate to the use of ketoreductase polypeptides of the present invention in the synthesis of an (S)—N-methyl-3-hydroxy-3-(aryl)-propanamine, the method comprising:

(a) providing a 3-aryl-3-ketopropanamine substrate having the structure of formula (I):

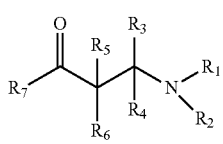

(I)

wherein $R_1$ and $R_2$ are each methyl, $R_3$, $R_4$, $R_5$, and $R_6$ are each independently selected from the group consisting of hydrogen and an optionally substituted lower alkyl, and $R_7$ is an optionally substituted aryl;

(b) contacting the 3-aryl-3-ketopropanamine substrate with one or more ketoreductase polypeptides of the present invention in a reaction mixture under conditions suitable for reduction or conversion of the substrate to an (S)-3-aryl-3-hydroxypropanime product having the structural formula (II):

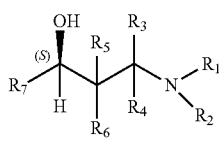

(II)

wherein $R_1$ and $R_2$ are each methyl, $R_3$, $R_4$, $R_5$, and $R_6$ are each independently selected from the group consisting of hydrogen and a an optionally substituted lower alkyl, and $R_7$ is an optionally substituted aryl;

(c) demethylating the (S)-3-aryl-3-hydroxypropanamine (i.e., N,N-dimethyl-3-hydroxy-3-(aryl)-propanamine) product of step (b) in a reaction mixture under conditions suitable for producing an (S)—N-methyl-3-hydroxy-3-(aryl)-propanamine having the formula of structure (II):

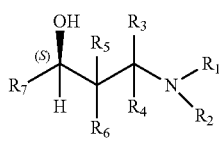

(II)

wherein one of $R_1$ and $R_2$ is methyl and the other is hydrogen, $R_3$, $R_4$, $R_5$, and $R_6$ are each independently selected from the group consisting of hydrogen and an optionally substituted lower alkyl, and $R_7$ is an optionally substituted aryl.

In some embodiments, the methods relate to the use of the ketoreductase polypeptides of the present invention in the synthesis of a 3-aryloxy-3-arylpropanamine, the method comprising:

(a) providing a 3-aryl-3-ketopropanamine having the structure of formula (I):

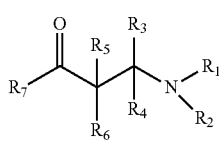

(I)

(b) contacting the 3-aryl-3-ketopropanamine with a ketoreductase polypeptide of the present invention in a reaction mixture under conditions sufficient to produce an (S)-3-aryl-3-hydroxypropanamine having the structure of formula (II):

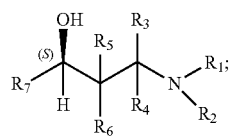

(II)

(c) contacting the (S)-3-aryl-3-hydroxypropanamine with an activated aryl compound in a reaction mixture under conditions sufficient to produce the (S)-3-aryloxy-3-(aryl)-propanamine having the structure of formula (VII):

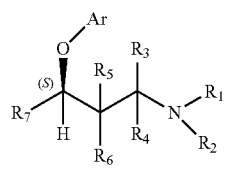

(VII)

wherein for (I), (II), and (VII), $R_1$ and $R_2$ are each independently selected from the group consisting of hydrogen, an optionally substituted lower alkyl, an optionally substituted cycloalkyl, an optionally substituted aryl, or alternatively, where $R_1$ and $R_2$ together form an optionally substituted cycloalkyl or an optionally substituted cycloaryl having 3-7 carbon atoms; $R_3$, $R_4$, $R_5$, and $R_6$ are each independently selected from the group consisting of hydrogen and an optionally substituted lower alkyl; and $R_7$ is an optionally substituted aryl and additionally, for (VII), Ar is an optionally substituted aryl group.

In some embodiments, the methods relate to use of the ketoreductase polypeptides in the synthesis of Duloxetine, (3S)—N-methyl-3-naphthalen-1-yloxy-3-thiophen-2-yl-propan-1-amine, having the structure of formula (VIII):

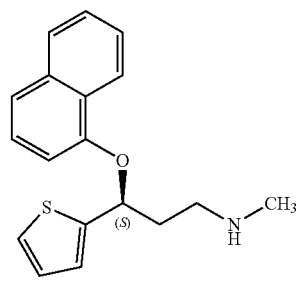

(VIII)

including salts, hydrates and solvates thereof. Thus, in a method for the synthesis of the compound of formula (VIII), a step in the method comprises reducing the substrate of structural formula (III) to the corresponding product of formula (IV) by contacting or incubating the substrate with a ketoreductase polypeptide described herein, thereby reducing the substrate to the product compound.

BRIEF DESCRIPTION OF THE DRAWINGS

FIG. 1 illustrates the role of ketoreductases in the conversion of the compound of formula (III), N-methyl-3-keto-3-(2-thienyl)-1-propanamine, to the corresponding chiral alcohol product of formula (IV), (S)—N-methyl-3-hydroxy-3-(2-thienyl)-1-propanamine. In the illustrated reaction, the reduction uses a cofactor such as NADPH. A glucose dehydrogenase can be used to convert/recycle the NADP+ to NADPH. Glucose is converted to gluconic acid, which is in turn converted to its sodium salt (sodium gluconate) with the addition of sodium hydroxide.

DETAILED DESCRIPTION

Definitions

As used herein, the following terms are intended to have the following meanings.

"Ketoreductase" and "KRED" are used interchangeably herein to refer to a polypeptide having an enzymatic capability of reducing a carbonyl group to its corresponding alcohol. More specifically, the ketoreductase polypeptides of the invention are capable of stereoselectively reducing the compound of formula (I) to the corresponding product of formula (II). The polypeptide typically utilizes a cofactor reduced nicotinamide adenine dinucleotide (NADH) or reduced nicotinamide adenine dinucleotide phosphate (NADPH) as the reducing agent. Ketoreductases as used herein include naturally occurring (wild type) ketoreductases as well as non-naturally occurring engineered polypeptides generated by human manipulation.

"Coding sequence" refers to that portion of a nucleic acid (e.g., a gene) that encodes an amino acid sequence of a protein.

"Naturally-occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

"Recombinant" when used with reference to, e.g., a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, 1981, *Adv. Appl. Math.* 2:482, by the homology alignment algorithm of Needleman and Wunsch, 1970, *J. Mol. Biol.* 48:443, by the search for similarity method of Pearson and Lipman, 1988, *Proc. Natl. Acad. Sci. USA* 85:2444, by computerized implementations of these algorithms (GAP, BESTFIT, FASTA, and TFASTA in the GCG Wisconsin Software Package), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)), all of which are incorporated herein by reference. Examples of algorithms that are suitable for determining percent sequence identity and sequence similarity are the BLAST and BLAST 2.0 algorithms, which are described in Altschul et al., 1990, *J. Mol. Biol.* 215: 403-410 and Altschul et al., 1977, *Nucleic Acids Res.* 3389-3402, respectively, which are incorporated herein by reference. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al., supra, which is incorporated herein by reference). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, *Proc Natl Acad Sci USA* 89:10915, which is incorporated herein by reference). Exemplary determination of sequence alignment and % sequence identity can employ the BESTFIT or GAP programs in the GCG Wisconsin Software package (Accelrys, Madison WI), using default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a "comparison window" to identify and compare local regions of sequence similarity.

In some embodiments, a "reference sequence" can be based on a primary amino acid sequence, where the reference sequence is a sequence that can have one or more changes in the primary sequence. For instance, a reference sequence "based on SEQ ID NO:4 having at the residue corresponding to X94 an aspartic acid" refers to a reference sequence in which the corresponding residue at X94 in SEQ ID NO:4 has been changed to an aspartic acid.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Substantial identity" refers to a polynucleotide or polypeptide sequence that has at least 80 percent sequence identity, at least 85 percent identity and 89 to 95 percent sequence identity, more usually at least 99 percent sequence identity as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term "substantial identity" means that two polypeptide sequences, when optimally aligned, such as by the programs GAP or BESTFIT using default gap weights, share at least 80 percent sequence identity, preferably at least 89 percent sequence identity, at least 95 percent sequence identity or more (e.g., 99 percent sequence identity). Preferably, residue positions which are not identical differ by conservative amino acid substitutions.

Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered ketoreductase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned. In some embodiments, unless specifically described otherwise, the terms "Xn", "residue position n", or "residue n", where "n" is the number position of a residue with respect to a reference sequence, are to be used in the context of "corresponding to" as described herein.

"Stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diastereomers, commonly alternatively reported as the diastereomeric excess (d.e.). Enantiomeric excess and diastereomeric excess are types of stereomeric excess.

"Highly stereoselective" refers to a ketoreductase polypeptide that is capable of converting or reducing the substrate to the corresponding (S)-product with at least about 99% stereomeric excess.

"Stereospecificity" refers to the preferential conversion in a chemical or enzymatic reaction of one stereoisomer over another. Stereospecificity can be partial, where the conversion of one stereoisomer is favored over the other, or it may be complete where only one stereoisomer is converted.

"Chemoselectivity" refers to the preferential formation in a chemical or enzymatic reaction of one product over another.

"Improved enzyme property" refers to a ketoreductase polypeptide that exhibits an improvement in any enzyme property as compared to a reference ketoreductase. For the engineered ketoreductase polypeptides described herein, the comparison is generally made to the wild-type ketoreductase enzyme, although in some embodiments, the reference ketoreductase can be another improved engineered ketoreductase. Enzyme properties for which improvement is desirable include, but are not limited to, enzymatic activity (which can be expressed in terms of percent conversion of the substrate), thermal stability, pH activity profile, cofactor requirements, refractoriness to inhibitors (e.g., product inhibition), stereospecificity, and stereoselectivity (including enantioselectivity).

"Increased enzymatic activity" refers to an improved property of the engineered ketoreductase polypeptides, which can be represented by an increase in specific activity (e.g., product produced/time/weight protein) or an increase in percent conversion of the substrate to the product (e.g., percent conversion of starting amount of substrate to product in a specified time period using a specified amount of KRED) as compared to the reference ketoreductase enzyme. Exemplary methods to determine enzyme activity are provided in the Examples. Any property relating to enzyme activity may be affected, including the classical enzyme properties of $K_m$, $V_{max}$ or $k_{cat}$, changes of which can lead to increased enzymatic activity. Improvements in enzyme activity can be from about 100% improved over the enzymatic activity of the corresponding wild-type ketoreductase enzyme, to as much as 200%, 500%, 1000%, 1500% or more over the enzymatic activity of the naturally occurring ketoreductase or another engineered ketoreductase from which the ketoreductase polypeptides were derived. In specific embodiments, the engineered ketoreductase enzyme exhibits improved enzymatic activity in the range of a 100% to 200%, 200% to 1000%, up to and more than a 1500% improvement over that of the parent, wild-type or other reference ketoreductase enzyme. It is understood by the skilled artisan that the activity of any enzyme is diffusion limited such that the catalytic turnover rate cannot exceed the diffusion rate of the substrate, including any required cofactors. The theoretical maximum of the diffusion limit, or $k_{cat}/K_m$, is generally about $10^8$ to $10$ $(M^{-1}s^{-1})$. Hence, any improvements in the enzyme activity of the ketoreductase will have an upper limit related to the diffusion rate of the substrates acted on by the ketoreductase enzyme. Ketoreductase activity can be measured by any one of standard assays used for measuring ketoreductase, such as a decrease in absorbance or fluorescence of NADPH due to its oxidation with the concomitant reduction of a ketone to an alcohol, or by product produced in a coupled assay. Comparisons of enzyme activities are made using a defined preparation of enzyme, a defined assay under a set condition, and one or more defined substrates, as further described in detail herein. Generally, when lysates are compared, the numbers of cells and the amount of protein assayed are determined as well as use of identical expression systems and identical host cells to minimize variations in amount of enzyme produced by the host cells and present in the lysates.

"Conversion" refers to the enzymatic reduction of the substrate to the corresponding product. "Percent conversion" refers to the percent of the substrate that is reduced to the product within a period of time under specified conditions. Thus, the "enzymatic activity" or "activity" of a ketoreductase polypeptide can be expressed as "percent conversion" of the substrate to the product.

"Thermostable" refers to a ketoreductase polypeptide that maintains similar activity (more than 60% to 80% for example) after exposure to elevated temperatures (e.g., 40-80° C.) for a period of time (e.g. 0.5-24 hrs) compared to the untreated enzyme.

"Solvent stable" refers to a ketoreductase polypeptide that maintains similar activity (more than e.g. 60% to 80%) after exposure to varying concentrations (e.g., 0.5-99%) of solvent (isopropyl alcohol, tetrahydrofuran, 2-methyltetrahydrofuran, acetone, toluene, butylacetate, methyl tert-butyleether, etc.) for a period of time (e.g., 0.5-24 hrs) compared to the untreated enzyme.

"pH stable" refers to a ketoreductase polypeptide that maintains similar activity (more than e.g., 60% to 80%) after exposure to high or low pH (e.g., 8 to 12 or 4.5-6) for a period of time (e.g., 0.5-24 hrs) compared to the untreated enzyme.

"Thermo- and solvent stable" refers to a ketoreductase polypeptide that are both thermostable and solvent stable.

"Derived from" as used herein in the context of engineered ketoreductase enzymes, identifies the originating ketoreductase enzyme, and/or the gene encoding such ketoreductase enzyme, upon which the engineering was based. For example, the engineered ketoreductase enzyme of SEQ ID NO:8 was obtained by artificially evolving, over multiple generations the gene encoding the *Lactobacillus kefir* ketoreductase enzyme of SEQ ID NO:2. Thus, this engineered ketoreductase enzyme is "derived from" the wild-type ketoreductase of SEQ ID NO: 2.

"Hydrophilic Amino Acid or Residue" refers to an amino acid or residue having a side chain exhibiting a hydrophobicity of less than zero according to the normalized consensus hydrophobicity scale of Eisenberg et al., 1984, *J. Mol. Biol.* 179:125-142. Genetically encoded hydrophilic amino acids include L-Thr (T), L-Ser (S), L-His (H), L-Glu (E), L-Asn (N), L-Gln (Q), L-Asp (D), L-Lys (K) and L-Arg (R).

"Acidic Amino Acid or Residue" refers to a hydrophilic amino acid or residue having a side chain exhibiting a pK value of less than about 6 when the amino acid is included in a peptide or polypeptide. Acidic amino acids typically have negatively charged side chains at physiological pH due to loss of a hydrogen ion. Genetically encoded acidic amino acids include L-Glu (E) and L-Asp (D).

"Basic Amino Acid or Residue" refers to a hydrophilic amino acid or residue having a side chain exhibiting a pK value of greater than about 6 when the amino acid is included in a peptide or polypeptide. Basic amino acids typically have positively charged side chains at physiological pH due to association with hydronium ion. Genetically encoded basic amino acids include L-Arg (R) and L-Lys (K).

"Polar Amino Acid or Residue" refers to a hydrophilic amino acid or residue having a side chain that is uncharged at physiological pH, but which has at least one bond in which the pair of electrons shared in common by two atoms is held more closely by one of the atoms. Genetically encoded polar amino acids include L-Asn (N), L-Gln (Q), L-Ser (S) and L-Thr (T).

"Hydrophobic Amino Acid or Residue" refers to an amino acid or residue having a side chain exhibiting a hydrophobicity of greater than zero according to the normalized consensus hydrophobicity scale of Eisenberg et al., 1984, *J. Mol. Biol.* 179:125-142. Genetically encoded hydrophobic amino acids include L-Pro (P), L-Ile (I), L-Phe (F), L-Val (V), L-Leu (L), L-Trp (W), L-Met (M), L-Ala (A) and L-Tyr (Y).

"Aromatic Amino Acid or Residue" refers to a hydrophilic or hydrophobic amino acid or residue having a side chain that includes at least one aromatic or heteroaromatic ring. Genetically encoded aromatic amino acids include L-Phe (F), L-Tyr (Y) and L-Trp (W). Although owing to the pKa of its heteroaromatic nitrogen atom L-His (H) it is sometimes classified as a basic residue, or as an aromatic residue as its side chain includes a heteroaromatic ring, herein histidine is classified as a hydrophilic residue or as a "constrained residue" (see below).

"Constrained amino acid or residue" refers to an amino acid or residue that has a constrained geometry. Herein, constrained residues include L-pro (P) and L-his (H). Histidine has a constrained geometry because it has a relatively small imidazole ring. Proline has a constrained geometry because it also has a five membered ring.

"Non-polar Amino Acid or Residue" refers to a hydrophobic amino acid or residue having a side chain that is uncharged at physiological pH and which has bonds in which the pair of electrons shared in common by two atoms is generally held equally by each of the two atoms (i.e., the side chain is not polar). Genetically encoded non-polar amino acids include L-Gly (G), L-Leu (L), L-Val (V), L-Ile (I), L-Met (M) and L-Ala (A).

"Aliphatic Amino Acid or Residue" refers to a hydrophobic amino acid or residue having an aliphatic hydrocarbon side chain. Genetically encoded aliphatic amino acids include L-Ala (A), L-Val (V), L-Leu (L) and L-Ile (I).

"Cysteine." The amino acid L-Cysteine (C) is unusual in that it can form disulfide bridges with other L-Cys (C) amino acids or other sulfanyl- or sulfhydryl-containing amino acids. The "cysteine-like residues" include cysteine and other amino acids that contain sulfhydryl moieties that are available for formation of disulfide bridges. The ability of L-Cys (C) (and other amino acids with —SH containing side chains) to exist in a peptide in either the reduced free —SH or oxidized disulfide-bridged form affects whether L-Cys (C) contributes net hydrophobic or hydrophilic character to a peptide. While L-Cys (C) exhibits a hydrophobicity of 0.29 according to the normalized consensus scale of Eisenberg (Eisenberg et al., 1984, supra), it is to be understood that for purposes of the present disclosure L-Cys (C) is categorized into its own unique group.

"Small Amino Acid or Residue" refers to an amino acid or residue having a side chain that is composed of a total three or fewer carbon and/or heteroatoms (excluding the α-carbon and hydrogens). The small amino acids or residues may be further categorized as aliphatic, non-polar, polar or acidic small amino acids or residues, in accordance with the above definitions. Genetically-encoded small amino acids include L-Ala (A), L-Val (V), L-Cys (C), L-Asn (N), L-Ser (S), L-Thr (T) and L-Asp (D).

"Hydroxyl-containing Amino Acid or Residue" refers to an amino acid containing a hydroxyl (—OH) moiety. Genetically-encoded hydroxyl-containing amino acids include L-Ser (S) L-Thr (T) and L-Tyr (Y).

"Conservative" amino acid substitutions or mutations refer to the interchangeability of residues having similar side chains, and thus typically involves substitution of the amino acid in the polypeptide with amino acids within the same or similar defined class of amino acids. However, as used herein, in some embodiments, conservative mutations do not include substitutions from a hydrophilic to hydrophilic, hydrophobic to hydrophobic, hydroxyl-containing to hydroxyl-containing, or small to small residue, if the conservative mutation can instead be a substitution from an aliphatic to an aliphatic, non-polar to non-polar, polar to polar, acidic to acidic, basic to basic, aromatic to aromatic, or constrained to constrained residue. Further, as used herein, A, V, L, or I can be conservatively mutated to either another aliphatic residue or to another non-polar residue. Table 1 below shows exemplary conservative substitutions.

TABLE 1

Conservative Substitutions

| Residue | Possible Conservative Mutations |
| --- | --- |
| A, L, V, I | Other aliphatic (A, L, V, I) |
| | Other non-polar (A, L, V, I, G, M) |
| G, M | Other non-polar (A, L, V, I, G, M) |
| D, E | Other acidic (D, E) |
| K, R | Other basic (K, R) |
| P, H | Other constrained (P, H) |
| N, Q, S, T | Other polar (N, Q, S, T) |
| Y, W, F | Other aromatic (Y, W, F) |
| C | None |

"Non-conservative substitution" refers to substitution or mutation of an amino acid in the polypeptide with an amino acid with significantly differing side chain properties. Non-conservative substitutions may use amino acids between, rather than within, the defined groups listed above. In one embodiment, a non-conservative mutation affects (a) the structure of the peptide backbone in the area of the substitution (e.g., proline for glycine) (b) the charge or hydrophobicity, or (c) the bulk of the side chain.

"Deletion" refers to modification to the polypeptide by removal of one or more amino acids from the reference polypeptide. Deletions can comprise removal of 1 or more amino acids, 2 or more amino acids, 3 or more amino acids, 4 or more amino acids, 5 or more amino acids, 6 or more amino acids, 7 or more amino acids, 8 or more amino acids, 10 or more amino acids, 12 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an engineered ketoreductase enzyme. Deletions can be directed to the internal portions and/or terminal portions of the polypeptide. In various embodiments, the deletion can comprise a continuous segment or can be discontinuous.

"Insertion" refers to modification to the polypeptide by addition of one or more amino acids from the reference polypeptide. In some embodiments, the improved engineered ketoreductase enzymes comprise insertions of one or more amino acids to the naturally occurring ketoreductase polypeptide as well as insertions of one or more amino acids to other improved ketoreductase polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

"Fragment" as used herein refers to a polypeptide that has an amino-terminal and/or carboxy-terminal deletion, but where the remaining amino acid sequence is identical to the corresponding positions in the sequence. Fragments can be at least 14 amino acids long, at least 20 amino acids long, at least 50 amino acids long or longer, and up to 70%, 80%, 90%, 95%, 98%, and 99% of a full-length ketoreductase polypeptide.

"Isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The improved ketoreductase enzymes may be present within a cell, present in the cellular medium, or prepared in various forms, such as lysates or isolated preparations. As such, in some embodiments, the improved ketoreductase enzyme can be an isolated polypeptide.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure ketoreductase composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated improved ketoreductases polypeptide is a substantially pure polypeptide composition.

"Stringent hybridization" is used herein to refer to conditions under which nucleic acid hybrids are stable. As known to those of skill in the art, the stability of hybrids is reflected in the melting temperature ($T_m$) of the hybrids. In general, the stability of a hybrid is a function of ion strength, temperature, G/C content, and the presence of chaotropic agents. The $T_m$ values for polynucleotides can be calculated using known methods for predicting melting temperatures (see, e.g., Baldino et al., *Methods Enzymology* 168:761-777; Bolton et al., 1962, *Proc. Natl. Acad. Sci. USA* 48:1390; Bresslauer et al., 1986, *Proc. Natl. Acad. Sci USA* 83:8893-8897; Freier et al., 1986, *Proc. Natl. Acad. Sci USA* 83:9373-9377; Kierzek et al., *Biochemistry* 25:7840-7846; Rychlik et al., 1990, *Nucleic Acids Res* 18:6409-6412 (erratum, 1991, *Nucleic Acids Res* 19:698); Sambrook et al., supra); Suggs et al., 1981, In Developmental Biology Using Purified Genes (Brown et al., eds.), pp. 683-693, Academic Press; and Wetmur, 1991, *Crit Rev Biochem Mol Biol* 26:227-259. All publications incorporate herein by reference). In some embodiments, the polynucleotide encodes the polypeptide disclosed herein and hybridizes under defined conditions, such as moderately stringent or highly stringent conditions, to the complement of a sequence encoding an engineered ketoreductase enzyme of the present disclosure.

"Hybridization stringency" relates to such washing conditions of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA, with greater than about 90% identity to target-polynucleotide. Exemplary moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 42° C. "High stringency hybridization" refers generally to conditions that are about 10° C. or less from the thermal melting temperature $T_m$ as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5×Denhart's solution, 5×SSPE, 0.2% SDS at 42° C., followed by washing in 0.1×SSPE, and 0.1% SDS at 65° C. Another high stringency condition is hybridizing in conditions equivalent to hybridizing in 5×SSC containing 0.1% (w:v) SDS at 65° C. and washing in 0.1×SSC containing 0.1% SDS at 65° C. Other high stringency hybridization conditions, as well as moderately stringent conditions, are described in the references cited above.

"Heterologous" polynucleotide refers to any polynucleotide that is introduced into a host cell by laboratory techniques, and includes polynucleotides that are removed from a host cell, subjected to laboratory manipulation, and then reintroduced into a host cell.

"Codon optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the ketoreductases enzymes may be codon optimized for optimal production from the host organism selected for expression.

"Preferred, optimal, high codon usage bias codons" refers interchangeably to codons that are used at higher frequency in the protein coding regions than other codons that code for the same amino acid. The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. A variety of methods are known for determining the codon frequency (e.g., codon usage, relative synonymous codon usage) and codon preference in specific organisms, including multivariat analysis, for example, using cluster analysis or correspondence analysis, and the effective number of codons used in a gene (see GCG CodonPreference, Genetics Computer Group Wisconsin Package; CodonW, John Peden, University of Nottingham; McInerney, J. O, 1998, *Bioinformatics* 14:372-73; Stenico et al., 1994, *Nucleic Acids Res.* 222437-46; Wright, F., 1990, *Gene* 87:23-29, which are incorporated herein by reference). Codon usage tables are available for a growing list of organisms (see for example, Wada et al., 1992, *Nucleic Acids Res.* 20:2111-2118; Nakamura et al., 2000, *Nucl. Acids Res.* 28:292; Duret, et al., supra; Henaut and Danchin, "*Escherichia coli* and *Salmonella,*" 1996, Neidhardt, et al. Eds., ASM Press, Washington D.C., p. 2047-2066, which are incorporated herein by reference). The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTS), or predicted coding regions of genomic sequences (see for example, Mount, D., *Bioinformatics: Sequence and Genome Analysis*, Chapter 8, Cold Spring Harbor Laboratory Press, Cold Spring Harbor, N.Y., 2001; Uberbacher, E. C., 1996, *Methods Enzymol.* 266:259-281; Tiwari et al., 1997, *Comput. Appl. Biosci.* 13:263-270, all of which are incorporated herein by reference).

"Control sequence" is defined herein to include all components, which are necessary or advantageous for the expression of a polypeptide of the present disclosure. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

"Operably linked" is defined herein as a configuration in which a control sequence is appropriately placed at a position relative to the coding sequence of the DNA sequence such that the control sequence directs the expression of a polynucleotide and/or polypeptide.

"Promoter sequence" is a nucleic acid sequence that is recognized by a host cell for expression of the coding region. The control sequence may comprise an appropriate promoter sequence. The promoter sequence contains transcriptional control sequences, which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

"Cofactor regeneration system" refers to a set of reactants that participate in a reaction that reduces the oxidized form of the cofactor (e.g., NADP+ to NADPH). Cofactors oxidized by the ketoreductase-catalyzed reduction of the keto substrate are regenerated in reduced form by the cofactor regeneration system. Cofactor regeneration systems comprise a stoichiometric reductant that is a source of reducing hydrogen equivalents and is capable of reducing the oxidized form of the cofactor. The cofactor regeneration system may further comprise a catalyst, for example an enzyme catalyst, that catalyzes the reduction of the oxidized form of the cofactor by the reductant. Cofactor regeneration systems to regenerate NADH or NADPH from NAD+ or NADP+, respectively, are known in the art and may be used in the methods described herein.

Ketoreductase Peptides

The present disclosure provides engineered ketoreductase ("KRED") enzymes that are useful for reducing or converting a 3-aryl-3-ketopropanamine substrate having the structural formula (I):

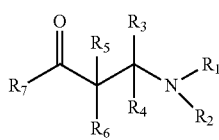

(I)

to the corresponding (S)-3-aryl-3-hydroxypropanamine having the structural formula (II):

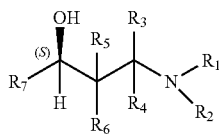

(II)

wherein for (I) and (II), $R_1$ and $R_2$ are each independently selected from the group consisting of hydrogen, an optionally substituted lower alkyl, an optionally substituted cycloalkyl, an optionally substituted aryl, or alternatively, where $R_1$ and $R_2$ together form an optionally substituted cycloalkyl or an optionally substituted cycloaryl having 3-7 carbon atoms; $R_3$, $R_4$, $R_5$, and $R_6$ are each independently selected from the group consisting of hydrogen and an optionally substituted lower alkyl; and $R_7$ is an optionally substituted aryl.

As described above, suitable substrates for the ketoreductase polypeptides of the present invention include those having the substituents described for formula (I) which may be optionally substituted. The term "optionally substituted" refers to the replacement of hydrogen with a monovalent or divalent radical. Suitable substitution groups include, for example, hydroxyl, nitro, amino, imino, cyano, halo, thio, thioamido, amidino, imidino, oxo, oxamidino, methoxamidino, imidino, guanidino, sulfonamide, carboxyl, formyl, lower alkyl, lower alkoxy, and the like. Products having the structure of formula (II) will have the same optionally substituted substituents described above.

As used herein, the term "lower alkyl" refers to branched or straight chain alkyl groups comprising one to ten carbon atoms that are unsubstituted or substituted, e.g., with one or more halogen, hydroxyl, and the like. The term "lower alkoxy" refers herein to RO—, wherein R is lower alkyl. Representative examples of lower alkoxy groups include methoxy, ethoxy, t-butoxy, trifluoromethoxy, and the like.

"Aryl" refers herein to monocyclic and polycyclic aromatic groups having from 3 to 14 backbone carbon or hetero atoms, and includes both carbocyclic aryl groups and heterocyclic aryl groups. Carbocyclic aryl groups are aryl groups in which all ring atoms in the aromatic ring are carbon. The term "heterocyclic aryl" refers herein to aryl groups having from 1 to 4 heteroatoms as ring atoms in an aromatic ring with the remainder of the ring atoms being carbon atoms. When used in connection with aryl substituents, the term "polycyclic" refers herein to fused and non-fused cyclic structures in which at least one cyclic structure is aromatic. Exemplary aryl moieties employed as substituents in compounds of the present invention include phenyl, naphthyl, thiophenyl, and the like. Exemplary substituted aryl substituents include benzyl, and the like.

"Cycloalkyl" refers herein to a mono- or polycyclic, heterocyclic or carbocyclic alkyl substituent. Typical cycloalkyl substituents have from 3 to 10 backbone (i.e., ring) atoms in which each backbone atom is either a carbon or a heteroatom. Suitable heteroatoms include nitrogen, oxygen, and sulfur.

"Cycloaryl" refers herein to a mono- or polycyclic, heterocyclic or carbocyclic alkyl substituent. Typical cycloaryl substituents have from 3 to 10 backbone atoms in which each backbone atom is either a carbon or a heteroatom. Suitable heteroatoms include nitrogen, oxygen, and sulfur.

Typical substrates have the structure of formula (I) where $R_1$ and $R_2$ are each independently hydrogen, a lower alkyl of from one to ten or from one to six carbon atoms, or a phenyl. Usually, one of $R_1$ and $R_2$ is hydrogen and the other is methyl or both $R_1$ and $R_2$ are methyl. Each of $R_3$, $R_4$, $R_5$, and $R_6$ is typically hydrogen or a lower alkyl of from one to ten or from one to six carbon atoms, and more typically each of $R_3$, $R_4$, $R_5$, and $R_6$ is hydrogen. $R_7$ is typically an optionally substituted thiophenyl (such as, for example, an optionally substituted 2-thienyl or an optionally substituted 3-thienyl) or an optionally substituted phenyl. More typically, $R_7$ is 2-thienyl or phenyl. Useful substrates have the combination of substituents: $R_1$ is hydrogen, $R_2$ is methyl, $R_3$-$R_6$ are each hydrogen, $R_7$ is selected from the group consisting of 2-thienyl and phenyl; and $R_1$ and $R_2$ are methyl, $R_3$-$R_6$ are each hydrogen, $R_7$ is selected from the group consisting of 2-thienyl and phenyl. Reduction of these substrates yields a corresponding 3-aryl-3-hydroxypropanamine product having the structure of formula (II) with $R_1$-$R_7$ as described above.

Ketoreductase polypeptides of the present invention are particularly useful for stereoselectively reducing or converting the substrate N-methyl-3-keto-3-(2-thienyl)-1-propanamine ("the monomethyl substrate", i.e., a substrate compound having structural formula (I) where one or $R_1$ and $R_2$ is hydrogen and the other is methyl, $R_3$-$R_6$ are each hydrogen, and $R_7$ is 2-thienyl) to the product (S)—N-methyl-3- hydroxy-3-(2-thienyl)-1-propanamine ("the monomethyl product", i.e., a substrate compound having structural formula (II) where one of $R_1$ and $R_2$ is hydrogen and the other is methyl, $R_3$-$R_6$ are each hydrogen, and $R_7$ is 2-thienyl) and having an improved property when compared with the naturally-occurring, wild-type KRED enzyme obtained from *L. kefir* (SEQ ID NO:2) or *L. brevis* (SEQ ID NO:4) or *L. minor* (SEQ ID NO:60) or when compared with another engineered ketoreductase enzyme. Enzyme properties for which improvement is desirable include, but are not limited to, enzymatic activity, thermal stability, pH activity profile, cofactor requirements, refractoriness to inhibitors (e.g., product inhibition), stereospecificity, stereoselectivity, and solvent stability. The improvements can relate to a single enzyme property, such as enzymatic activity, or a combination of different enzyme properties, such as enzymatic activity and stereoselectivity.

For the ketoreductase polypeptides described herein, the amino acid sequence of the ketoreductases have, as compared to the reference sequence of SEQ ID NO:2, 4, or 60, the requirement that: (1) residue corresponding to residue position 94 is an acidic residue, (2) residue corresponding to residue position 145 is an aromatic residue or leucine, and (3) residue corresponding to residue position 190 is a cysteine or a constrained residue. In some embodiments, the ketoreductase polypeptides have, as compared to the KRED sequences of SEQ ID NO:2, 4 or 60, the following features: (1) residue corresponding to residue position 94 is aspartic acid, (2) residue corresponding to residue position 145 is phenylalanine, tyrosine, tryptophan or leucine, and (3) residue corresponding to residue position 190 is cysteine or proline. In some embodiments, the ketoreductase polypeptides have, as compared to the KRED sequences of SEQ ID NO:2, 4 or 60, the following features: (1) residue corresponding to residue position 94 is aspartic acid, (2) residue corresponding to residue position 145 is phenylalanine, tyrosine, or leucine, particularly phenylalanine or leucine, and (3) residue corresponding to residue position 190 is cysteine or proline, particularly proline. In some embodiments, the ketoreductase polypeptides have, as compared to the KRED sequences of SEQ ID NO:2, 4 or 60, the following features: (1) residue corresponding to residue position 94 is aspartic acid, (2) residue corresponding to residue position 145 is phenylalanine, and (3) residue corresponding to residue position 190 is proline.

In some embodiments, as noted above, the engineered ketoreductase with improved enzyme activity is described with reference to *Lactobacillus kefir* ketoreductase of SEQ ID NO:2, *Lactobacillus brevis* ketoreductase of SEQ ID NO:4, *Lactobacillus minor* of SEQ ID NO:60, or another engineered ketoreductase, such as SEQ ID NO:6. The amino acid residue position is determined in these ketoreductases beginning from the initiating methionine (M) residue (i.e., M represents residue position 1), although it will be understood by the skilled artisan that this initiating methionine residue may be removed by biological processing machinery, such as in a host cell or in vitro translation system, to generate a mature protein lacking the initiating methionine residue. The amino acid residue position at which a particular amino acid or amino acid change is present in an amino acid sequence is sometimes describe herein in terms "Xn", or "position n", where n refers to the residue position. Where the amino acid residues at the same residue position differ between the ketoreductases, the different residues are denoted by an "/" with the arrangement being, for example, "*kefir* residue/*brevis* residue/*minor*." A substitution mutation, which is a replacement of an amino acid residue in a corresponding residue of a reference sequence, for example the wildtype ketoreductases of SEQ ID NO:2, SEQ ID NO:4, or SEQ ID NO:60 with a different amino acid residue is denoted by the symbol "→".

Herein, mutations are sometimes described as a mutation "to a" type of amino acid. For example, residue 211 can be mutated "to a" basic residue. But the use of the phrase "to a" does not exclude mutations from one amino acid of a class to another amino acid of the same class. For example, residue 211 can be mutated from a lysine to an arginine.

The naturally occurring polynucleotide encoding the naturally occurring ketoreductase of *Lactobacillus kefir*, *Lactobacillus brevis*, or *Lactobacillus minor* (also referred to as "ADH" or "alcohol dehydrogenase") can be obtained from the isolated polynucleotide known to encode the ketoreductase activity (e.g., Genbank accession no. AAP94029 GI:33112056 or SEQ ID NO:3 for *Lactobacillus kefir*; Genbank accession no. CAD66648 GI:28400789 or SEQ ID NO:1 for *Lactobacillus brevis*; and U.S. Pat. Appl. No. 20040265978 or SEQ ID NO:60 for *Lactobacillus minor*).

In some embodiments, the ketoreductase polypeptides herein can have a number of modifications to the reference sequence (e.g., an engineered ketoreductase polypeptide) to result in an improved ketoreductase enzyme property. In such embodiments, the number of modifications to the amino acid sequence can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 10% of the total number of amino acids; up to 20% of the total number of amino acids, or up to 30% of the total number of amino acids of the reference polypeptide sequence. In some embodiments, the number of modifications to the naturally occurring polypeptide or an engineered polypeptide that produces an improved ketoreductase property may comprise from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 modifications of the reference sequence. In some embodiments, the number of modifications can be 1, 2, 3, 4, 5, 6, 7, 8, 9, 10, 11, 12, 14, 15, 16, 18, 20, 22, 24, 26, 30, 35 or about 40 amino acid residues. The modifications can comprise insertions, deletions, substitutions, or combinations thereof.

In some embodiments, the modifications comprise amino acid substitutions to the reference sequence. Substitutions that can produce an improved ketoreductase property may be at one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids, or up to 30% of the total number of amino acids of the reference enzyme sequence. In some embodiments, the number of substitutions to the naturally occurring polypeptide or an engineered polypeptide that produces an improved ketoreductase property can comprise from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 amino acid substitutions of the reference sequence. In some embodiments, the number of substitutions can be 1, 2, 3, 4, 5, 6, 7, 8, 9, 10, 11, 12, 14, 15, 16, 18, 20, 22, 24, 26, 30, 35 or about 40 substitutions at other amino acid residues.

In some embodiments, the improved property (as compared to wild-type or another engineered polypeptide) of the ketoreductase polypeptide is with respect to an increase of its stereoselectivity for reducing or converting the substrate N-methyl-3-keto-3-(2-thienyl)-1-propanamine to the product (S)—N-methyl-3-hydroxy-3-(2-thienyl)-1-propanamine. In some embodiments, the improved property of the ketoreductase property is with respect to an increase in stereoselectivity, i.e., herein, an increase in the stereomeric excess of the product. In some embodiments, the improved property of the ketoreductase polypeptide is with respect to an increase in its ability to convert or reduce a greater percentage of the substrate to the product. In some embodiments, the improved property of the ketoreductase polypeptide is with respect to an increase in its rate of conversion of the substrate to the product. This improvement in enzymatic activity can be manifested by the ability to use less of the improved polypeptide as compared to the wild-type or other reference sequence (for example, SEQ ID NO:6) to reduce or convert the same amount of product. In some embodiments, the improved property of the ketoreductase polypeptide is with respect to its stability or thermostability. In some embodiments, the ketoreductase polypeptide has more than one improved property.

In some embodiments, the ketoreductase polypeptide of the disclosure is capable of converting the substrate N-methyl-3-keto-3-(2-thienyl)-1-propanamine to the product (S)—N-methyl-3-hydroxy-3-(2-thienyl)-1-propanamine ("the monomethyl product"), with a percent stereomeric excess of at least about 99% and at a rate that is improved over a reference polypeptide having the amino acid sequence of SEQ ID NO:6. Exemplary polypeptides with such properties include, but are not limited to, polypeptides which comprise amino acid sequences corresponding to SEQ ID NO: 8, 10, 12, 14, 16, 18, 20, 22, 24, 26, 28, 30, and 32. Because the reference polypeptide having the amino acid sequence of SEQ ID NO:6 is capable of converting the monomethyl substrate to the corresponding monomethyl product at a rate greater than that of wild-type (e.g., SEQ ID NO:2), the polypeptides herein that are improved over SEQ ID NO:6 are also improved over wild-type.

In some embodiments, the ketoreductase polypeptide is capable of converting the substrate N-methyl-3-keto-3-(2-thienyl)-1-propanamine to the product (S)—N-methyl-3-hydroxy-3-(2-thienyl)-1-propanamine, with a percent stereomeric excess of at least about 99% and at a rate that is at least 5-10 times greater than a reference polypeptide having the amino acid sequence of SEQ ID NO:6. Exemplary polypeptides with such properties include, but are not limited to, polypeptides which comprise amino acid sequences corresponding to SEQ ID NO: 8, 10, and 20.

In some embodiments, the ketoreductase polypeptide is capable of converting the substrate N-methyl-3-keto-3-(2-thienyl)-1-propanamine to the product (S)—N-methyl-3-hydroxy-3-(2-thienyl)-1-propanamine, with a percent stereomeric excess of at least about 99% and at a rate that is at least 10-15 times greater than a reference polypeptide having the amino acid sequence of SEQ ID NO:6. Exemplary polypeptides with such properties include, but are not limited to, polypeptides which comprise amino acid sequences corresponding to SEQ ID NO: 12, 14, 16, 18, 22, 24, 26, 28, 30, and 32.

In some embodiments, the ketoreductase polypeptide is capable of converting the substrate N-methyl-3-keto-3-(2-thienyl)-1-propanamine to the product (S)—N-methyl-3-hydroxy-3-(2-thienyl)-1-propanamine, with a percent stereomeric excess of at least about 99% and at a rate that is at least 1500% improved over a reference polypeptide having the amino acid sequence of SEQ ID NO:6. Exemplary polypeptides with such properties include, but are not limited to, polypeptides which comprise amino acid sequences corresponding to SEQ ID NO: 24, 26, 28, 30, and 32.

In some embodiments, the ketoreductase polypeptide is capable of converting at least about 95% of the monomethyl substrate to the monomethyl product in less than about 24 hours when carried out with greater than about 100 g/L of substrate and less than about 5 g/L of the polypeptide. Exemplary polypeptides that have this capability include, but are not limited to, polypeptides which comprises amino acid sequences corresponding to SEQ ID NO: 24, 26, 28, 30, and 32.

In some embodiments, the ketoreductase polypeptides of the disclosure are highly stereoselective and can reduce the monomethyl substrate to the monomethyl product in greater than about 99%, 99.1%, 99.2%, 99.3%, 99.4%, 99.5%, 99.6%, 99.7%, 99.8% or 99.9% stereomeric excess. Exemplary ketoreductase polypeptides with such high stereoselectivity include, but are not limited to, the polypeptides comprising the amino acid sequences corresponding to SEQ ID NO: 8, 10, 12, 14, 16, 18, 20, 22, 24, 26, 28, 30, and 32.

Table 2 below provides a list of the SEQ ID NOs disclosed herein with associated activity levels with respect to the reduction of the monomethyl substrate to the corresponding monomethyl product. The sequences below are also derived from the wild-type *L. kefir* ketoreductase sequences (SEQ ID NO: 1 and 2) unless otherwise specified. In Table 2 below, each row lists two SEQ ID NOs, where the odd number refers to the nucleotide sequence that codes for the amino acid sequence provided by the even number. The column listing the number of mutations is with respect to the number of amino acid substitutions as compared to the *L. kefir* KRED amino acid sequence of SEQ ID NO:2. In the activity column, one "+" indicates that the enzyme's ketoreductase activity is 5-10 times greater than that of the enzyme of SEQ ID NO:6. Similarly, a two plus sign symbol "++" indicates that the polypeptide ketoreductase activity is from 10 to about 15 times greater that the reference enzyme SEQ ID NO:6, and the three plus sign symbol "+++" indicates that the polypeptide ketoreductase activity is more than 15 times greater than the activity of the reference enzyme of SEQ ID NO: 6.

TABLE 2

List of Sequences and Corresponding Activity Improvement with respect to reduction of N-methyl-3-keto-3-(2-thienyl)-1-propanamine ("monomethyl substrate"):

| SEQ ID NO (Poly-nucleotide/ amino acid) | Residue Changes (Relative to SEQ ID NO: 2) | Number of mutations (relative to the wild-type L. kefir sequence SEQ ID NO: 2) | Activity Monomethyl Substrate |
|---|---|---|---|
| 5/6 | H40R; A94G; S96V; E145F; F147M; Y190P; L195M; V196L; M206W; I226V; D233G; Y249W | 12 | "Control" |
| 7/8 | H40R; A94D; S96V; E145F; F147M; Y190P; L195M; V196L; M206W; I226V; D233G; Y249W | 12 | + |
| 9/10 | H40R; A94D; S96V; K109E; E145F; F147M Y190P; L195M; V196L; M206W; I226V; D233G; Y249W | 13 | + |
| 11/12 | H40R; K46R; A94D; S96V; E145F; F147M; L153V; Y190P; L195M; V196L; L199V; M206W; I226V; D233G; V245I; Y249W | 16 | ++ |
| 13/14 | H40R; K46R; A94D; E145F; F147M; L153V; Y190P; L195M; V196L; L199V; M206W; I226V; D233G; V245I; Y249W | 15 | ++ |
| 15/16 | H40R; K46R; A94D; E145F; F147M; L153V; Y190P; L195M; V196L; L199R; M206W; I226V; D233G; V245I; Y249W | 15 | ++ |
| 17/18 | H40R; K46R; A94D; S96P; E145F; F147M; L153V; Y190P; L195M; V196L; L199V; M206W; I226V; D233G; V245I; Y249W | 16 | ++ |
| 19/20 | H40R; K46R; A94D; S96G; E145F; F147M; L153V; Y190P; L195M; V196L; L199V; M206W; I226V; D233G; V245I; Y249W | 16 | + |
| 21/22 | H40R; K46R; A94D; S96V; E145F; F147M; L153V; Y190P; L195M; V196L; L199E; M206W; I226V; D233G; V245I; Y249W | 16 | ++ |
| 23/24 | H40R; K46R; A94D; S96V; E145F; F147M; L153V; Y190P; L195M; V196L; D198N, L199V; M206W; I226V; D233G; V245I; Y249W | 17 | +++ |
| 25/26 | H40R; K46R; A94D; S96V; E145F; F147M; L153V; N157S, Y190P; L195M; V196L; L199V; M206W; I226V; D233G; V245I; Y249W | 17 | +++ |
| 27/28 | H40R; K46R; V60I, A94D; S96V; R108H, E145F; F147M; L153V; Y190P; L195M; V196L; L199V; M206W; I226V; D233G; V245I; Y249W | 18 | +++ |
| 29/30 | H40R; K46R; A64V, A94D; S96V; E145F; F147M; L153V; Y190P; L195M; V196L; L199V; M206W; I226V; D233G; V245I; Y249W | 17 | +++ |
| 31/32 | H40R; K46R; A94D; S96V; E145F; F147M; T152N, L153V; Y190P; L195M; V196L; L199E; M206W; I226V; D233G; V245I; Y249W | 17 | +++ |

In some embodiments, the improved ketoreductase polypeptide herein comprises an amino acid sequence that is at least about 85%, 86%, 87%, 88%, 89%, 90%, 91%, 92%, 93%, 94%, 95%, 96%, 97%, 98%, or 99% identical as compared a reference sequence based on SEQ ID NO:2, 4 or 60 having the following features described herein, for example: the amino acid residue corresponding to position 94 is an acidic residue; the amino acid residue corresponding to position 145 is aromatic residue or leucine; and the amino acid corresponding to position 190 is cysteine or proline, and wherein the ketoreductase polypeptides have at least the preceding features. In some embodiments, the improved ketoreductases have the specified sequence identity based on a reference ketoreductase and have the following features: the amino acid residue corresponding to position 94 is an aspartic acid; the amino acid residue corresponding to position 145 is phenylalanine, tyrosine, tryptophan, or leucine, particularly phenylalanine or leucine; and the amino acid corresponding to position 190 is cysteine or proline, particularly proline, and wherein the ketoreductase polypeptides have at least the preceding features. In some embodiments, these ketoreductase polypeptides can have one or more modifications as compared to the reference amino acid sequence. The modifications can include substitutions, deletions, and insertions. The substitutions can be non-conservative substitutions, conservative substitutions, or a combination of non-conservative and conservative substitutions. In some embodiments, these ketoreductase polypeptides can have optionally from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, or about 1-35 mutations at other amino acid residues. In some embodiments, the number of mutations can be 1, 2, 3, 4, 5, 6, 7, 8, 9, 10, 11, 12, 14, 15, 16, 18, 20, 22, 24, 26, 30, 35 or about 40 mutations at other amino acid residues.

In some embodiments, an improved ketoreductase polypeptide comprises an amino acid sequence that corresponds to the sequence formula as presented in SEQ ID NO:61, 62, or 63, or a region thereof, such as residues 90-211. SEQ ID NO:61 is based on the amino acid sequence of the *Lactobacillus kefir* ketoreductase (SEQ ID NO:2); SEQ ID NO:62 is based on the amino acid sequence of the *Lactobacillus brevis* ketoreductase (SEQ ID NO:4); and SEQ ID NO:63 is based on the amino acid sequence of the *Lactobacillus minor* ketoreductase (SEQ ID NO:60). SEQ ID NOs:61, 62 and 63 specify that residue corresponding to X94 is an acidic amino acid, residue corresponding to X145 is an aromatic amino acid or leucine, and residue corresponding to X190 is cysteine or a constrained amino acid. In some embodiments, the ketoreductase polypeptide based on the sequence formula of SEQ ID NOs:61, 62 or 63 can comprise an amino acid sequence that is at least about 85%, 86%, 87%, 88%, 89%, 90%, 91%, 92%, 93%, 94%, 95%, 96%, 97%, 98%, or 99% identical to a reference amino acid sequence based on SEQ ID NO:2, 4, or 60 having at least the features described herein for amino acid residues X94, X145, and X190, with the proviso that the ketoreductase polypeptides have at least the specified features. In some embodiments, the amino acid sequence of the ketoreductase polypeptides have at least the following features: the amino acid residue corresponding to X94 is aspartic acid; the amino acid residue corresponding to X145 is phenylalanine, tyrosine, or leucine, particularly phenylalanine or leucine; and the amino acid corresponding to X190 is cysteine or proline, particularly proline, with the proviso that the ketoreductase polypeptides have at least the specified features.

In some embodiments, the improved ketoreductase polypeptides comprising an amino acid sequence based on the sequence formula of SEQ ID NO:61, 62 or 63, or region thereof, such as residue 90-211, having the specified features for residues X94, X145, and X190 as described herein, can further include one or more features selected from the following: residue corresponding to X7 is nonpolar or constrained residue; residue corresponding to X40 is a constrained, hydrophilic or basic residue; residue corresponding to X46 is a hydrophilic or basic residue; residue corresponding to X60 is an aliphatic or non polar residue; residue corresponding to X64 is an aliphatic or non-polar residue; residue corresponding to X96 is a polar, constrained, non-polar or aliphatic residue; residue corresponding to X108 is a hydrophilic, polar or constrained residue; residue corresponding to X109 is an acidic residue; residue corresponding to X147 is an aromatic, non-polar, aliphatic, or hydrophobic residue; residue corresponding to X152 is a polar residue; residue corresponding to X153 is a polar, non-polar, or aliphatic residue; residue corresponding to X157 is a polar residue; residue corresponding to X195 is a non-polar, aliphatic, or basic residue; residue corresponding to X196 is a non polar or aliphatic residue; residue corresponding to X198 is an acidic, polar residue, hydrophilic residue; residue corresponding to X199 is an acidic, basic, hydrophilic, aliphatic or nonpolar residue; residue corresponding to X206 is a nonpolar, aromatic, or hydrophobic residue; residue corresponding to X226 is a non polar or aliphatic residue; residue corresponding to X233 is an acidic, non-polar, or aliphatic residue; residue corresponding to X245 is a non polar or aliphatic residue; and residue corresponding to X249 is a nonpolar or aromatic residue. In some of the foregoing embodiments, the amino acid residue corresponding to X94 is aspartic acid; the amino acid residue corresponding to X145 is phenylalanine, tyrosine, or leucine, particularly phenylalanine; and the amino acid corresponding to X190 is cysteine or proline, particularly proline. In some embodiments, the polypeptides comprising an amino acid sequence that corresponds to the sequence formula provided in SEQ ID NO:61, 62 or 63, or region thereof, can have additionally one or more of the residues not specified by an X to be mutated as compared to the reference sequence of SEQ ID NO:2, 4 or 60. In some embodiments, the mutations can be from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 mutations at other amino acid residues not defined by X above. In some embodiments, the number of mutations can be 1, 2, 3, 4, 5, 6, 7, 8, 9, 10, 11, 12, 14, 15, 16, 18, 20, 22, 24, 26, 30, 35 or about 40 amino acid residues. In some embodiments, the mutations comprise conservative mutations.

In some embodiments, the improved ketoreductase polypeptides comprising an amino acid sequence based on the sequence formula of SEQ ID NO:61, 62 and 63, or region thereof, such as residue 90-211, having the specified features for residues X94, X145, and X190 as described herein, can have one or more conservative mutations as compared to the amino acid sequence of SEQ ID NO:2, 4, or 60. Examples of such conservative mutations include amino acid replacements such as, but not limited to, replacement of residue X46 lysine (K) with another hydrophilic or basic residue, e.g. arginine (R); replacement of residue X60 valine (V) with another aliphatic or non-polar residue, e.g. isoleucine (I); replacement of residue X64 alanine (A) with another aliphatic or non-polar residue, e.g. valine (V); replacement of residue X152 threonine (T) with another polar residue, e.g., asparagine (N); replacement of residue X153 with another aliphatic or non-polar residue, e.g., valine; replacement of residue X157 asparagine (N) with another polar residue, e.g., serine (S); replacement of residue 185 threonine (T) with another polar residue, e.g., serine (S); replacement of residue X195 leucine (L) with another aliphatic or non-polar residue, e.g., methionine (M); replacement of residue X196 valine (V) with another non polar, hydrophobic, or aliphatic residue, e.g., leucine (L) or isoleucine (I); replacement of residue X199 leucine (L) with another non-polar or aliphatic residue, e.g., valine (V); replacement of residue 226 isoleucine (I) with another non-polar or aliphatic residue, e.g. valine (V); replacement of residue 245 valine (V) with another non-polar or aliphatic residue, e.g. isoleucine (I); and replacement of residue 249 tyrosine (Y) with another hydrophobic or aromatic residue, e.g. tryptophan (W).

In some embodiments, the improved ketoreductase polypeptides based on the sequence formula of SEQ ID NO: 61, 62 or 63, or a region thereof, such as residues 90-211, having the features at residues X94, X145, and X190 as described herein, can further include one or more the features selected from the following: residue corresponding to X7 is glycine, methionine, alanine, valine, leucine, isoleucine, proline or histidine, particularly histidine; residue corresponding to X40 is threonine, serine, histidine, glutamic acid, asparagine, glutamine, aspartic acid, lysine, or arginine, particularly arginine; residue corresponding to X46 is arginine or lysine; residue corresponding to X60 is glycine, methionine, alanine, valine, leucine, or isoleucine, particularly isoleucine; residue corresponding to X64 is glycine, methionine, alanine, valine, leucine, isoleucine, particularly valine; residue corresponding to X96 is proline, serine, threonine, asparagine, glutamine, glycine, methionine, alanine, valine, leucine, or isoleucine, particularly valine, proline, or glycine; residue corresponding to X108 is threonine, serine, histidine, glutamic acid, asparagine, glutamine, aspartic acid, lysine, particularly histidine; residue corresponding to X109 is aspartic or glutamic acid; residue corresponding to X147 is isoleucine, phenylalanine, valine, leucine, tryptophan, methionine, alanine and tyrosine, particularly isoleucine, methionine, valine, or leucine; residue corresponding to X152 is serine, threonine, asparagine or glutamine, particularly asparagine; residue corresponding to X153 is alanine, valine, leucine, isoleucine, serine, threonine, asparagine, or glutamine, particularly valine; residue corresponding to X157 is serine, threonine, asparagine, or glutamine, particularly serine; residue corresponding to X195 is glycine, methionine, alanine, valine, leucine, or isoleucine, particularly methionine; residue corresponding to X196 is glycine, methionine, alanine, valine, leucine, isoleucine, particularly leucine; residue corresponding to X198 is aspartic acid, glutamic acid, serine, threonine, asparagine, or glutamine, particularly asparagine; residue corresponding to X199 is aspartic acid, glutamic acid, arginine, lysine, serine, threonine, asparagine, glutamine, glycine, methionine, alanine, valine, leucine, or isoleucine, particularly valine, arginine, or glutamic acid; residue corresponding to X206 is isoleucine, phenylalanine, valine, leucine, tryptophan, methionine, alanine or tyrosine, particularly tyrosine, tryptophan, or phenylalanine; residue corresponding to X226 is glycine, methionine, alanine, valine, leucine, or isoleucine, particularly valine; residue corresponding to X233 is glycine, methionine, alanine, valine, leucine, isoleucine, aspartic acid, or glutamic acid, particularly glycine; residue corresponding to X245 is glycine, methionine, alanine, valine, leucine, or isoleucine, particularly isoleucine; and residue corresponding to X249 is isoleucine, phenylalanine, valine, leucine, tryptophan, methionine, alanine or tyrosine, particularly tryptophan. In some embodiments, the polypeptides comprising an amino acid sequence that corresponds to the sequence formula provided in SEQ ID NO: 61, 62 or 63 (or region thereof) can have additionally one or more of the residues not specified by an X to be mutated as compared to the reference sequence of SEQ ID NO: 2, 4 or 60. In some embodiments, the mutations can be 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 mutations at other amino acid residues not defined by X above. In some embodiments, the number of mutations can be 1, 2, 3, 4, 5, 6, 7, 8, 9, 10, 11, 12, 14, 15, 16, 18, 20, 22, 24, 26, 30, 35 or about 40 mutations at other amino acid residues. In some embodiments, the mutations comprise conservative mutations.

In some embodiments, the improved ketoreductase polypeptides comprising an amino acid sequence based on the sequence formula of SEQ ID NO:61, 62 or 63, or region thereof, such as residues 90-211, having the specified features for residues X94, X145, and X190 as described herein, can further include one or more or at least all of the following features: residue corresponding to X147 is an aromatic, non-polar, aliphatic, or hydrophobic residue; residue corresponding to X206 is nonpolar, aromatic, or hydrophobic residue; and residue corresponding to X233 is an acidic, non-polar, or aliphatic residue. In some of the foregoing embodiments, the amino acid residue corresponding to X94 is aspartic acid; the amino acid residue corresponding to X145 is phenylalanine, tyrosine, or leucine, particularly phenylalanine or leucine; and the amino acid corresponding to X190 is cysteine or proline, particularly proline. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 60. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 60 with the preceding features.

In some embodiments, the improved ketoreductase polypeptides comprising an amino acid sequence based on the sequence formula of SEQ ID NO:61, 62 or 63, or region thereof, such as residues 90-211, having the specified features for residues X94, X145, and X190 as described herein, can further include one or more or at least all of the following features: residue corresponding to X40 is a constrained, hydrophilic or basic residue; residue corresponding to X96 is a polar, constrained, non-polar or aliphatic residue; residue corresponding to X147 is an aromatic, non-polar, aliphatic, or hydrophobic residue; residue corresponding to X199 is an acidic, basic, hydrophilic, aliphatic or nonpolar residue; residue corresponding to X206 is a nonpolar, aromatic, or hydrophobic residue; and residue corresponding to X233 is an acidic, non-polar, or aliphatic residue. In some of the foregoing embodiments, the amino acid residue corresponding to X94 is aspartic acid; the amino acid residue corresponding to X145 is phenylalanine, tyrosine, or leucine, particularly phenylalanine or leucine; and the amino acid corresponding to X190 is cysteine or proline, particularly proline. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 60. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 60 with the preceding features.

In some embodiments, the improved ketoreductase polypeptides comprising an amino acid sequence based on the sequence formula of SEQ ID NO:61, 62 or 63, or region thereof, such as residues 90-211, having the specified features for residues X94, X145, and X190 as described herein, can further include one or more or at least all of the following features: residue corresponding to X147 is an aromatic, non-polar, aliphatic, or hydrophobic residue; residue corresponding to X195 is a non-polar, aliphatic, or basic residue; residue corresponding to X196 is a non polar or aliphatic residue; residue corresponding to X206 is a nonpolar, aromatic, or hydrophobic residue; residue corresponding to X226 is a non polar or aliphatic residue; residue corresponding to X233 is an acidic, non-polar, or aliphatic residue; and residue corresponding to X249 is a nonpolar or aromatic residue.

In some of the foregoing embodiments, the amino acid residue corresponding to X94 is aspartic acid; the amino acid residue corresponding to X145 is phenylalanine, tyrosine, or leucine, particularly phenylalanine or leucine; and the amino acid corresponding to X190 is cysteine or proline, particularly proline. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 60. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 60 with the preceding features.

In some embodiments, the improved ketoreductase polypeptides based on the sequence formula of SEQ ID NO: 61, 62 or 63, or a region thereof, such as residues 90-211, having the features described herein at residues X94, X145, and X190 as described herein, can further include one or more or at least all of the following features: residue corresponding to X147 is isoleucine, phenylalanine, valine, leucine, tryptophan, methionine, alanine and tyrosine, particularly isoleucine, methionine, valine, or leucine; residue corresponding to X195 is glycine, methionine, alanine, valine, leucine, or isoleucine, particularly methionine; residue corresponding to X196 is glycine, methionine, alanine, valine, leucine, isoleucine, particularly leucine; residue corresponding to X206 is isoleucine, phenylalanine, valine, leucine, tryptophan, methionine, alanine or tyrosine, particularly tyrosine, tryptophan, or phenylalanine; residue corresponding to X226 is glycine, methionine, alanine, valine, leucine, or isoleucine, particularly valine; residue corresponding to X233 is glycine, methionine, alanine, valine, leucine, isoleucine, aspartic acid, or glutamic acid, particularly glycine; and residue corresponding to X249 is isoleucine, phenylalanine, valine, leucine, tryptophan, methionine, alanine or tyrosine, particularly tryptophan. In some of the foregoing embodiments, and the amino acid residue corresponding to X94 is aspartic acid; the amino acid residue corresponding to X145 is phenylalanine, tyrosine, or leucine, particularly phenylalanine or leucine; and the amino acid corresponding to X190 is cysteine or proline, particularly proline. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 60. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 60 with the preceding features.

In some embodiments, the improved ketoreductase polypeptides comprising an amino acid sequence based on the sequence formula of SEQ ID NO:61, 62 or 63, or region thereof, such as residue 90-211, having the specified features for residues X94, X145, and X190 as described herein, can further include at one or more or at least all of the following features: residue corresponding to X40 is a constrained, hydrophilic or basic residue; residue corresponding to X46 is a hydrophilic or basic residue; residue corresponding to X96 is a polar, constrained, non-polar or aliphatic residue; residue corresponding to X147 is an aromatic, non-polar, aliphatic, or hydrophobic residue; residue corresponding to X153 is a polar, non-polar, or aliphatic residue; residue corresponding to X195 is a non-polar, aliphatic, or basic residue; residue corresponding to X196 is a non polar or aliphatic residue; residue corresponding to X199 is an acidic, basic, hydrophilic, aliphatic or nonpolar residue; residue corresponding to X206 is a nonpolar, aromatic, or hydrophobic residue; residue corresponding to X226 is a non polar or aliphatic residue; residue corresponding to X233 is an acidic, non-polar, or aliphatic residue; residue corresponding to X245 is a non polar or aliphatic residue; and residue corresponding to X249 is a nonpolar or aromatic residue. In some of the foregoing embodiments, the amino acid residue corresponding to X94 is aspartic acid; the amino acid residue corresponding to X145 is phenylalanine, tyrosine, or leucine, particularly phenylalanine or leucine; and the amino acid corresponding to X190 is cysteine or proline, particularly proline. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 60. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 60 with the preceding features.

In some embodiments, the improved ketoreductase polypeptides based on the sequence formula of SEQ ID NO: 61, 62 or 63, or a region thereof, such as residues 90-211, having the features described herein at residues X94, X145, and X190 as described herein, can further include one or more or at least all of the following features: residue corresponding to X40 is threonine, serine, histidine, glutamic acid, asparagine, glutamine, aspartic acid, lysine, or arginine, particularly arginine; residue corresponding to X46 is arginine or lysine; residue corresponding to X96 s proline, serine, threonine, asparagine, glutamine, glycine, methionine, alanine, valine, leucine, or isoleucine, particularly valine, proline, or glycine; residue corresponding to X147 s isoleucine, phenylalanine, valine, leucine, tryptophan, methionine, alanine and tyrosine, particularly isoleucine, methionine, valine, or leucine; residue corresponding to X153 is alanine, valine, leucine, isoleucine, serine, threonine, asparagine, or glutamine, particularly valine; residue corresponding to X195 is glycine, methionine, alanine, valine, leucine, or isoleucine, particularly methionine; residue corresponding to X196 is glycine, methionine, alanine, valine, leucine, isoleucine, particularly leucine; residue corresponding to X199 is aspartic acid, glutamic acid, arginine, lysine, serine, threonine, asparagine, glutamine, glycine, methionine, alanine, valine, leucine, or isoleucine, particularly valine, arginine, or glutamic acid; residue corresponding to X206 is isoleucine, phenylalanine, valine, leucine, tryptophan, methionine, alanine or tyrosine, particularly tyrosine, tryptophan, or phenylalanine; residue corresponding to X226 is glycine, methionine, alanine, valine, leucine, or isoleucine, particularly valine; residue corresponding to X233 is glycine, methionine, alanine, valine, leucine, isoleucine, aspartic acid, or glutamic acid, particularly glycine; residue corresponding to X245 is glycine, methionine, alanine, valine, leucine, or isoleucine, particularly isoleucine; and residue corresponding to X249 is isoleucine, phenylalanine, valine, leucine, tryptophan, methionine, alanine or tyrosine, particularly tryptophan. In some of the foregoing embodiments, the amino acid residue corresponding to X94 is aspartic acid; the amino acid residue corresponding to X145 is phenylalanine, tyrosine, or leucine, particularly phenylalanine or leucine; and the amino acid corresponding to X190 is cysteine or proline, particularly proline. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 60. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 60 with the preceding features.

In some embodiments, an improved ketoreductase comprises an amino acid sequence based on the sequence formula of SEQ ID NO: 61, 62 or 63, or a region thereof, such as residues 90-211, in which the amino acid sequence has at least the following features: residue corresponding to X94 is aspartic acid; residue corresponding to X145 is phenylalanine, tyrosine, or leucine, particularly phenylalanine or leucine; residue corresponding to X190 is cysteine or proline, particularly proline; and residue corresponding to X7 is a nonpolar or constrained residue, particularly a histidine. In some embodiments, the ketoreductase polypeptides can have additionally from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 mutations at other amino acid residues. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 60. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 60 with the preceding features.

In some embodiments, an improved ketoreductase comprises an amino acid sequence based on the sequence formula of SEQ ID NO: 61, 62 or 63, or a region thereof, such as residues 90-211, in which the amino acid sequence has at least the following features: residue corresponding to X94 is aspartic acid; residue corresponding to X145 is phenylalanine, tyrosine, or leucine, particularly phenylalanine or leucine; residue corresponding to X190 is cysteine or proline, particularly proline; and residue corresponding to X40 is a constrained, hydrophilic or basic residue, particularly arginine. In some embodiments, the ketoreductase polypeptides can have additionally from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 mutations at other amino acid residues. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 60. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 60 with the preceding features.

In some embodiments, an improved ketoreductase comprises an amino acid sequence based on the sequence formula of SEQ ID NO: 61, 62 or 63, or a region thereof, such as residues 90-211, in which the amino acid sequence has at least the following features: residue corresponding to X94 is aspartic acid; residue corresponding to X145 is phenylalanine, tyrosine, or leucine, particularly phenylalanine or leucine; residue corresponding to X190 is cysteine or proline, particularly proline; and residue corresponding to X46 is a hydrophilic or basic residue, particularly arginine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 60. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 60 with the preceding features.

In some embodiments, an improved ketoreductase comprises an amino acid sequence based on the sequence formula of SEQ ID NO: 61, 62 or 63, or a region thereof, such as residues 90-211, in which the amino acid sequence has at least the following features: residue corresponding to X94 is aspartic acid; residue corresponding to X145 is phenylalanine, tyrosine, or leucine, particularly phenylalanine or leucine; residue corresponding to X190 is cysteine or proline, particularly proline; and residue corresponding to X60 is an aliphatic or non polar residue, particularly isoleucine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 60. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 60 with the preceding features.

In some embodiments, an improved ketoreductase comprises an amino acid sequence based on the sequence formula of SEQ ID NO: 61, 62 or 63, or a region thereof, such as residues 90-211, in which the amino acid sequence has at least the following features: residue corresponding to X94 is aspartic acid; residue corresponding to X145 is phenylalanine, tyrosine, or leucine, particularly phenylalanine or leucine; residue corresponding to X190 is cysteine or proline, particularly proline; and residue corresponding to X64 is an aliphatic or non-polar residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 60. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 60 with the preceding features.

In some embodiments, an improved ketoreductase comprises an amino acid sequence based on the sequence formula of SEQ ID NO: 61, 62 or 63, or a region thereof, such as residues 90-211, in which the amino acid sequence has at least the following features: residue corresponding to X94 is aspartic acid; residue corresponding to X145 is phenylalanine, tyrosine, or leucine, particularly phenylalanine or leucine; residue corresponding to X190 is cysteine or proline, particularly proline; and residue corresponding to X96 is a polar, constrained, non-polar or aliphatic residue, particularly proline, glycine, and valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 60. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 60 with the preceding features.

In some embodiments, an improved ketoreductase comprises an amino acid sequence based on the sequence formula of SEQ ID NO: 61, 62 or 63, or a region thereof, such as residues 90-211, in which the amino acid sequence has at least the following features: residue corresponding to X94 is aspartic acid; residue corresponding to X145 is phenylalanine, tyrosine, or leucine, particularly phenylalanine or leucine; residue corresponding to X190 is cysteine or proline, particularly proline; and residue corresponding to X108 is a hydrophilic, polar or constrained residue, particularly histidine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 60. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 60 with the preceding features.

In some embodiments, an improved ketoreductase comprises an amino acid sequence based on the sequence formula of SEQ ID NO: 61, 62 or 63, or a region thereof, such as residues 90-211, in which the amino acid sequence has at least the following features: residue corresponding to X94 is aspartic acid; residue corresponding to X145 is phenylalanine, tyrosine, or leucine, particularly phenylalanine or leucine; residue corresponding to X190 is cysteine or proline, particularly proline; and residue corresponding to X109 is an acidic residue, particularly glutamic acid. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 60. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 60 with the preceding features.

In some embodiments, an improved ketoreductase comprises an amino acid sequence based on the sequence formula of SEQ ID NO: 61, 62 or 63, or a region thereof, such as residues 90-211, in which the amino acid sequence has at least the following features: residue corresponding to X94 is aspartic acid; residue corresponding to X145 is phenylalanine, tyrosine, or leucine, particularly phenylalanine or leucine; residue corresponding to X190 is cysteine or proline, particularly proline; and residue corresponding to X147 is an aromatic, non-polar, aliphatic, or hydrophobic residue, particularly methionine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 60. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 60 with the preceding features.

In some embodiments, an improved ketoreductase comprises an amino acid sequence based on the sequence formula of SEQ ID NO: 61, 62 or 63, or a region thereof, such as residues 90-211, in which the amino acid sequence has at least the following features: residue corresponding to X94 is aspartic acid; residue corresponding to X145 is phenylalanine, tyrosine, or leucine, particularly phenylalanine or leucine; residue corresponding to X190 is cysteine or proline, particularly proline; and residue corresponding to X152 is a polar residue, particularly asparagine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 60. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 60 with the preceding features.

In some embodiments, an improved ketoreductase comprises an amino acid sequence based on the sequence formula of SEQ ID NO: 61, 62 or 63, or a region thereof, such as residues 90-211, in which the amino acid sequence has at least the following features: residue corresponding to X94 is aspartic acid; residue corresponding to X145 is phenylalanine, tyrosine, or leucine, particularly phenylalanine or leucine; residue corresponding to X190 is cysteine or proline, particularly proline; and residue corresponding to X153 is a polar, non-polar, or aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 60. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 60 with the preceding features.

In some embodiments, an improved ketoreductase comprises an amino acid sequence based on the sequence formula of SEQ ID NO: 61, 62 or 63, or a region thereof, such as residues 90-211, in which the amino acid sequence has at least the following features: residue corresponding to X94 is aspartic acid; residue corresponding to X145 is phenylalanine, tyrosine, or leucine, particularly phenylalanine or leucine; residue corresponding to X190 is cysteine or proline, particularly proline; and residue corresponding to X157 is a polar residue, particularly serine or threonine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 60. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 60 with the preceding features.

In some embodiments, an improved ketoreductase comprises an amino acid sequence based on the sequence formula of SEQ ID NO: 61, 62 or 63, or a region thereof, such as residues 90-211, in which the amino acid sequence has at least the following features: residue corresponding to X94 is aspartic acid; residue corresponding to X145 is phenylalanine, tyrosine, or leucine, particularly phenylalanine or leucine; residue corresponding to X190 is cysteine or proline, particularly proline; and residue corresponding to X195 is a non-polar, aliphatic, or basic residue, particularly methionine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 60. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 60 with the preceding features.

In some embodiments, an improved ketoreductase comprises an amino acid sequence based on the sequence formula of SEQ ID NO: 61, 62 or 63, or a region thereof, such as residues 90-211, in which the amino acid sequence has at least the following features: residue corresponding to X94 is aspartic acid; residue corresponding to X145 is phenylalanine, tyrosine, or leucine, particularly phenylalanine or leucine; residue corresponding to X190 is cysteine or proline, particularly proline; and residue corresponding to X196 is a non polar or aliphatic residue, particularly leucine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 60. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 60 with the preceding features.

In some embodiments, an improved ketoreductase comprises an amino acid sequence based on the sequence formula of SEQ ID NO: 61, 62 or 63, or a region thereof, such as residues 90-211, in which the amino acid sequence has at least the following features: residue corresponding to X94 is aspartic acid; residue corresponding to X145 is phenylalanine, tyrosine, or leucine, particularly phenylalanine or leucine; residue corresponding to X190 is cysteine or proline, particularly proline; and residue corresponding to X198 is an acidic, polar residue, hydrophilic residue, particularly asparagine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 60. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 60 with the preceding features.

In some embodiments, an improved ketoreductase comprises an amino acid sequence based on the sequence formula of SEQ ID NO: 61, 62 or 63, or a region thereof, such as residues 90-211, in which the amino acid sequence has at least the following features: residue corresponding to X94 is aspartic acid; residue corresponding to X145 is phenylalanine, tyrosine, or leucine, particularly phenylalanine or leucine; residue corresponding to X190 is cysteine or proline, particularly proline; and residue corresponding to X199 is acidic, basic, hydrophilic, aliphatic or nonpolar residue, particularly valine, glutamic acid, or arginine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 60. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 60 with the preceding features.

In some embodiments, an improved ketoreductase comprises an amino acid sequence based on the sequence formula of SEQ ID NO: 61, 62 or 63, or a region thereof, such as residues 90-211, in which the amino acid sequence has at least the following features: residue corresponding to X94 is aspartic acid; residue corresponding to X145 is phenylalanine, tyrosine, or leucine, particularly phenylalanine or leucine; residue corresponding to X190 is cysteine or proline, particularly proline; and residue corresponding to X206 is a nonpolar, aromatic, or hydrophobic residue, particularly phenylalanine, tyrosine, or tryptophan. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 60. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 60 with the preceding features.

In some embodiments, an improved ketoreductase comprises an amino acid sequence based on the sequence formula of SEQ ID NO: 61, 62 or 63, or a region thereof, such as residues 90-211, in which the amino acid sequence has at least the following features: residue corresponding to X94 is aspartic acid; residue corresponding to X145 is phenylalanine, tyrosine, or leucine, particularly phenylalanine or leucine; residue corresponding to X190 is cysteine or proline, particularly proline; and residue corresponding to X226 is a non polar or aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 60. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 60 with the preceding features.

In some embodiments, an improved ketoreductase comprises an amino acid sequence based on the sequence formula of SEQ ID NO: 61, 62 or 63, or a region thereof, such as residues 90-211, in which the amino acid sequence has at least the following features: residue corresponding to X94 is aspartic acid; residue corresponding to X145 is phenylalanine, tyrosine, or leucine, particularly phenylalanine or leucine; residue corresponding to X190 is cysteine or proline, particularly proline; and residue corresponding to X233 is an acidic, non-polar, or aliphatic residue, particularly glycine.

In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO: 2, 4 or 60. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 60 with the preceding features.

In some embodiments, an improved ketoreductase comprises an amino acid sequence based on the sequence formula of SEQ ID NO: 61, 62 or 63, or a region thereof, such as residues 90-211, in which the amino acid sequence has at least the following features: residue corresponding to X94 is aspartic acid; residue corresponding to X145 is phenylalanine, tyrosine, or leucine, particularly phenylalanine or leucine; residue corresponding to X190 is cysteine or proline, particularly proline; and residue corresponding to X245 is a non polar or aliphatic residue, particularly isoleucine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 60. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 60 with the preceding features.

In some embodiments, an improved ketoreductase comprises an amino acid sequence based on the sequence formula of SEQ ID NO: 61, 62 or 63, or a region thereof, such as residues 90-211, in which the amino acid sequence has at least the following features: amino acid residue corresponding to X94 is aspartic acid; the amino acid residue corresponding to X145 is phenylalanine, tyrosine, or leucine, particularly phenylalanine or leucine; the amino acid corresponding to X190 is cysteine or proline, particularly proline; and the amino acid residue corresponding to X249 is a nonpolar or aromatic residue, particularly tryptophan. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 60. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:2, 4 or 60 with the preceding features.

In some embodiments, an improved ketoreductase comprises an amino acid sequence that is at least about 85%, 86%, 87%, 88%, 89%, 90%, 91%, 92%, 93%, 94%, 95%, 96%, 97%, 98%, or 99% identical to the amino acid sequence corresponding to SEQ ID NO: 8, 10, 12, 14, 16, 18, 20, 22, 24, 26, 28, 30, and 32, as listed in Table 2, wherein the improved ketoreductase polypeptide amino acid sequence includes any one set of the specified amino acid substitution combinations presented in Table 2. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, the ketoreductases of the disclosure are subject to the proviso that they do not include the specific sequences corresponding to SEQ ID NO:12 and SEQ ID NO:22. Thus, each and every of the embodiments described herein has the proviso that it excludes the specific polypeptides defined by SEQ ID NO: 12 and 22.

In some embodiments, the improved ketoreductases comprise amino acid sequences corresponding to SEQ ID NO: 8, 10, 12, 14, 16, 18, 20, 22, 24, 26, 28, 30, and 32.

In some embodiments, an improved ketoreductase polypeptides comprises an amino acid sequence based on the sequence formula of SEQ ID NO: 61, 62 or 63, or a region thereof, such as residues 90-211, and has at least the following features: residue corresponding to X40 is a constrained, hydrophilic or basic residue, particularly arginine; residue corresponding to X94 is an acidic residue, particularly aspartic acid; residue corresponding to X96 is a polar, constrained, non-polar or aliphatic residue; residue corresponding to X145 is an aromatic residue or leucine; residue corresponding to X147 is an aromatic, non-polar, aliphatic, or hydrophobic residue, particularly methionine; residue corresponding to X190 is cysteine or a constrained residue, particularly proline; residue corresponding to X195 is a non-polar, aliphatic, or basic residue, particularly methionine; residue corresponding to X196 is a non polar or aliphatic residue, particularly leucine; residue corresponding to X206 is a nonpolar, aromatic, or hydrophobic residue, particularly tryptophan; residue corresponding to X226 is a non polar or aliphatic residue, particularly valine; residue corresponding to X233 is an acidic, non-polar, or aliphatic residue, particularly glycine; and residue corresponding to X249 is a nonpolar or aromatic residue, particularly tryptophan. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:10. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO: 10.

In some embodiments, an improved ketoreductase polypeptides comprises an amino acid sequence based on the sequence formula of SEQ ID NO: 61, 62 or 63, or a region thereof, such as residues 90-211, in which the amino acid sequence has at least the following features: residue corresponding to X40 is a constrained, hydrophilic or basic residue, particularly arginine; residue corresponding to X46 is a hydrophilic or basic residue, particularly arginine; residue corresponding to X94 is an acidic residue, particularly aspartic acid; residue corresponding to X96 is a polar, constrained, non-polar or aliphatic residue, particularly valine; residue corresponding to X145 is an aromatic residue or leucine, particularly phenylalanine; residue corresponding to X147 is an aromatic, non-polar, aliphatic, or hydrophobic residue, particularly methionine; residue corresponding to X153 is a polar, non-polar, or aliphatic residue, particularly valine; residue corresponding to X190 is cysteine or a constrained residue, particularly proline; residue corresponding to X195 is a non-polar, aliphatic, or basic residue, particularly methionine; residue corresponding to X196 is a non polar or aliphatic residue, particularly leucine; residue corresponding to X199 is an acidic, basic, hydrophilic, aliphatic or nonpolar residue, particularly valine; residue corresponding to X206 is a nonpolar, aromatic, or hydrophobic residue, particularly tryptophan; residue corresponding to X226 is a non polar or aliphatic residue, particularly valine; residue corresponding to X233 is an acidic, non-polar, or aliphatic residue, particularly glycine; residue corresponding to X245 is a non polar or aliphatic residue, particularly isoleucine; and residue corresponding to X249 is a nonpolar or aromatic residue, particularly tryptophan. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO: 12. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:12.

In some embodiments, an improved ketoreductase polypeptides comprises an amino acid sequence based on the sequence formula of SEQ ID NO: 61, 62 or 63, or a region thereof, such as residues 90-211, in which the amino acid sequence has at least the following features: residue corresponding to X40 is a constrained, hydrophilic or basic residue, particularly arginine; residue corresponding to X46 is a hydrophilic or basic residue, particularly arginine; residue corresponding to X94 is an acidic residue, particularly aspartic acid; residue corresponding to X145 is an aromatic residue or leucine, particularly phenylalanine; residue corresponding to X147 is an aromatic, non-polar, aliphatic, or hydrophobic residue, particularly methionine; residue corresponding to X153 is a polar, non-polar, or aliphatic residue, particularly valine; residue corresponding to X190 is cysteine or a constrained residue, particularly proline; residue corresponding to X195 is a non-polar, aliphatic, or basic residue, particularly methionine; residue corresponding to X196 is a non polar or aliphatic residue, particularly leucine; residue corresponding to X199 is an acidic, basic, hydrophilic, aliphatic or nonpolar residue, particularly valine or arginine; residue corresponding to X206 is a nonpolar, aromatic, or hydrophobic residue, particularly tryptophan; residue corresponding to X226 is a non polar or aliphatic residue, particularly valine; residue corresponding to X233 is an acidic, non-polar, or aliphatic residue, particularly glycine; residue corresponding to X245 is a non polar or aliphatic residue, particularly isoleucine, and residue corresponding to X249 is a nonpolar or aromatic residue, particularly tryptophan. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:14 or 16. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:14 or 16.

In some embodiments, an improved ketoreductase polypeptides comprises an amino acid sequence based on the sequence formula of SEQ ID NO: 61, 62 or 63, or a region thereof, such as residues 90-211, in which the amino acid sequence has at least the following features: residue corresponding to X40 is a constrained, hydrophilic or basic residue, particularly arginine; residue corresponding to X46 is a hydrophilic or basic residue, particularly arginine; residue corresponding to X94 is an acidic residue, particularly aspartic acid; residue corresponding to X96 is a polar, constrained, non-polar or aliphatic residue, particularly proline or glycine; residue corresponding to X145 is an aromatic residue or leucine, particularly phenylalanine; residue corresponding to X147 is an aromatic, non-polar, aliphatic, or hydrophobic residue, particularly methionine; residue corresponding to X153 is a polar, non-polar, or aliphatic residue, particularly valine; residue corresponding to X190 is cysteine or constrained residue, particularly proline; residue corresponding to X195 is a non-polar, aliphatic, or basic residue, particularly methionine; residue corresponding to X196 is a non polar or aliphatic residue, particularly leucine; residue corresponding to X199 is an acidic, basic, hydrophilic, aliphatic or nonpolar residue, particularly valine; residue corresponding to X206 is a nonpolar, aromatic, or hydrophobic residue, particularly tryptophan; residue corresponding to X226 is a non polar or aliphatic residue, particularly valine; residue corresponding to X233 is an acidic, non-polar, or aliphatic residue, particularly glycine; residue corresponding to X245 is a non polar or aliphatic residue, particularly isoleucine; and residue corresponding to X249 is a nonpolar or aromatic residue, particularly tryptophan. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:18 or 20. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:18 or 20.

In some embodiments, an improved ketoreductase polypeptides comprises an amino acid sequence based on the sequence formula of SEQ ID NO: 61, 62 or 63, or a region thereof, such as residues 90-211, in which the amino acid sequence has at least the following features: residue corresponding to X40 is a constrained, hydrophilic or basic residue, particularly arginine; residue corresponding to X46 is a hydrophilic or basic residue, particularly arginine; residue corresponding to X94 is an acidic residue, particularly aspartic acid; residue corresponding to X96 is a polar, constrained, non-polar or aliphatic residue, particularly valine; residue corresponding to X145 is an aromatic residue or leucine, particularly phenylalanine; residue corresponding to X147 is an aromatic, non-polar, aliphatic, or hydrophobic residue, particularly methionine; residue corresponding to X153 is a polar, non-polar, or aliphatic residue, particularly valine; residue corresponding to X190 is cysteine or constrained residue, particularly proline; residue corresponding to X195 is a non-polar, aliphatic, or basic residue, particularly methionine; residue corresponding to X199 is an acidic, basic, hydrophilic, aliphatic or nonpolar residue, particularly glutamic acid; residue corresponding to X206 is a nonpolar, aromatic, or hydrophobic residue, particularly tryptophan; residue corresponding to X226 is a non polar or aliphatic residue, particularly valine; residue corresponding to X233 is an acidic, non-polar, or aliphatic residue, particularly glycine; residue corresponding to X245 is a non polar or aliphatic residue, particularly isoleucine; and residue corresponding to X249 is a nonpolar or aromatic residue, particularly tryptophan. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:22. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:22.

In some embodiments, an improved ketoreductase polypeptides comprises an amino acid sequence based on the sequence formula of SEQ ID NO: 61, 62 or 63, or a region thereof, such as residues 90-211, in which the amino acid sequence has at least the following features: residue corresponding to X40 is a constrained, hydrophilic or basic residue, particularly arginine; residue corresponding to X46 is a hydrophilic or basic residue, particularly arginine; residue corresponding to X94 is an acidic residue, particularly aspartic acid; residue corresponding to X96 is a polar, constrained, non-polar or aliphatic residue, particularly valine; residue corresponding to X145 is an aromatic residue or leucine, particularly phenylalanine; residue corresponding to X147 is an aromatic, non-polar, aliphatic, or hydrophobic residue, particularly methionine; residue corresponding to X153 is a polar, non-polar, or aliphatic residue, particularly valine; residue corresponding to X190 is cysteine or constrained residue, particularly proline; residue corresponding to X195 is a non-polar, aliphatic, or basic residue, particularly methionine; residue corresponding to X196 is a non polar or aliphatic residue, particularly leucine; residue corresponding to X198 is an acidic, polar residue, hydrophilic residue, particularly asparagine; residue corresponding to X199 is an acidic, basic, hydrophilic, aliphatic or nonpolar residue, particularly valine; residue corresponding to X206 is a nonpolar, aromatic, or hydrophobic residue, particularly tryptophan; residue corresponding to X226 is a non polar or aliphatic residue, particularly valine; residue corresponding to X233 is an acidic, non-polar, or aliphatic residue, particularly glycine; residue corresponding to X245 is a non polar or aliphatic residue, particularly isoleucine; and residue corresponding to X249 is a nonpolar or aromatic residue, particularly tryptophan. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:22. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:24.

In some embodiments, an improved ketoreductase polypeptides comprises an amino acid sequence based on the sequence formula of SEQ ID NO: 61, 62 or 63, or a region thereof, such as residues 90-211, in which the amino acid sequence has at least the following features: residue corresponding to X40 is a constrained, hydrophilic or basic residue, particularly arginine; residue corresponding to X46 is a hydrophilic or basic residue, particularly arginine; residue corresponding to X94 is an acidic residue, particularly aspartic acid; residue corresponding to X96 is a polar, constrained, non-polar or aliphatic residue, particularly valine; residue corresponding to X145 is an aromatic residue or leucine, particularly phenylalanine; residue corresponding to X147 is an aromatic, non-polar, aliphatic, or hydrophobic residue, particularly methionine; residue corresponding to X153 is a polar, non-polar, or aliphatic residue, particularly valine; residue corresponding to X157 is a polar residue, particularly serine; residue corresponding to X190 is cysteine or constrained residue, particularly proline; residue corresponding to X195 is a non-polar, aliphatic, or basic residue, particularly methionine; residue corresponding to X196 is a non polar or aliphatic residue, particularly leucine; residue corresponding to X199 is an acidic, basic, hydrophilic, aliphatic or nonpolar residue, particularly valine; residue corresponding to X206 is a nonpolar, aromatic, or hydrophobic residue, particularly tryptophan; residue corresponding to X226 is a non polar or aliphatic residue, particularly valine; residue corresponding to X233 is an acidic, non-polar, or aliphatic residue, particularly glycine; residue corresponding to X245 is a non polar or aliphatic residue, particularly isoleucine; and residue corresponding to X249 is a nonpolar or aromatic residue, particularly tryptophan. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:26. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:26.

In some embodiments, an improved ketoreductase polypeptides comprises an amino acid sequence based on the sequence formula of SEQ ID NO: 61, 62 or 63, or a region thereof, such as residues 90-211, in which the amino acid sequence has at least the following features: residue corresponding to X40 is a constrained, hydrophilic or basic residue, particularly arginine; residue corresponding to X46 is a hydrophilic or basic residue, particularly arginine; residue corresponding to X60 is an aliphatic or non polar residue, particularly isoleucine; residue corresponding to X94 is an acidic residue, particularly aspartic acid; residue corresponding to X96 is a polar, constrained, non-polar or aliphatic residue, particularly valine; residue corresponding to X108 is a hydrophilic, polar or constrained residue, particularly histidine; residue corresponding to X145 is an aromatic residue or leucine, particularly phenylalanine; residue corresponding to X147 is an aromatic, non-polar, aliphatic, or hydrophobic residue, particularly methionine; residue corresponding to X153 is a polar, non-polar, or aliphatic residue, particularly valine; residue corresponding to X190 is cysteine or constrained residue, particularly proline; residue corresponding to X195 is a non-polar, aliphatic, or basic residue, particularly methionine; residue corresponding to X196 is a non polar or aliphatic residue, particularly leucine; residue corresponding to X199 is an acidic, basic, hydrophilic, aliphatic or nonpolar residue, particularly valine; residue corresponding to X206 is a nonpolar, aromatic, or hydrophobic residue, particularly tryptophan; residue corresponding to X226 is a non polar or aliphatic residue, particularly valine; residue corresponding to X233 is an acidic, non-polar, or aliphatic residue, particularly glycine; residue corresponding to X245 is a non polar or aliphatic residue, particularly isoleucine; and residue corresponding to X249 is a nonpolar or aromatic residue, particularly tryptophan. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:28. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:28.

In some embodiments, an improved ketoreductase polypeptides comprises an amino acid sequence based on the sequence formula of SEQ ID NO: 61, 62 or 63, or a region thereof, such as residues 90-211, in which the amino acid sequence has at least the following features: residue corresponding to X40 is a constrained, hydrophilic or basic residue, particularly arginine; residue corresponding to X46 is a hydrophilic or basic residue, particularly arginine; residue corresponding to X64 is an aliphatic or non-polar residue, particularly valine; residue corresponding to X94 is an acidic residue, particularly aspartic acid; residue corresponding to X96 is a polar, constrained, non-polar or aliphatic residue, particularly valine; residue corresponding to X108 is hydrophilic, polar or constrained residue, particularly histidine; residue corresponding to X145 is an aromatic residue or leucine, particularly phenylalanine; residue corresponding to X147 is an aromatic, non-polar, aliphatic, or hydrophobic residue, particularly methionine; residue corresponding to X153 is a polar, non-polar, or aliphatic residue, particularly valine; residue corresponding to X190 is cysteine or constrained residue, particularly proline; residue corresponding to X195 is a non-polar, aliphatic, or basic residue, particularly methionine; residue corresponding to X196 is a non polar or aliphatic residue, particularly leucine; residue corresponding to X199 is an acidic, basic, hydrophilic, aliphatic or nonpolar residue, particularly valine; residue corresponding to X206 is a nonpolar, aromatic, or hydrophobic residue, particularly tryptophan; residue corresponding to X226 is a non polar or aliphatic residue, particularly valine; residue corresponding to X233 is an acidic, non-polar, or aliphatic residue, particularly glycine; residue corresponding to X245 is a non polar or aliphatic residue, particularly isoleucine; and residue corresponding to X249 is a nonpolar or aromatic residue, particularly tryptophan. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:30. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:30.

In some embodiments, an improved ketoreductase polypeptides comprises an amino acid sequence based on the sequence formula of SEQ ID NO: 61, 62 or 63, or a region thereof, such as residues 90-211, in which the amino acid sequence has at least the following features: residue corresponding to X40 is a constrained, hydrophilic or basic residue, particularly arginine; residue corresponding to X46 is a hydrophilic or basic residue, particularly arginine; residue corresponding to X94 is an acidic residue, particularly aspartic acid; residue corresponding to X96 is a polar, constrained, non-polar or aliphatic residue, particularly valine; residue corresponding to X145 is an aromatic residue or leucine, particularly phenylalanine; residue corresponding to X147 is an aromatic, non-polar, aliphatic, or hydrophobic residue, particularly methionine; residue corresponding to X152 is a polar residue, particularly asparagine; residue corresponding to X153 is a polar, non-polar, or aliphatic residue, particularly valine; residue corresponding to X190 is cysteine or constrained residue, particularly proline; residue corresponding to X195 is a non-polar, aliphatic, or basic residue, particularly methionine; residue corresponding to X196 is a non polar or aliphatic residue, particularly leucine; residue corresponding to X199 is an acidic, basic, hydrophilic, aliphatic or nonpolar residue, particularly valine; residue corresponding to X206 is a nonpolar, aromatic, or hydrophobic residue, particularly tryptophan; residue corresponding to X226 is a non polar or aliphatic residue, particularly valine; residue corresponding to X233 is an acidic, non-polar, or aliphatic residue, particularly glycine; residue corresponding to X245 is a non polar or aliphatic residue, particularly isoleucine; and residue corresponding to X249 is a nonpolar or aromatic residue, particularly tryptophan. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:32. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:32.

In some embodiments, an improved ketoreductase comprises an amino acid sequence that has a region or domain corresponding to residues 90-211 of sequence formula of SEQ ID NO: 61, 62 or 63, in which the amino acid sequence of the domain has at least the following features: (1) the amino acid residue corresponding to residue X94 is an acidic residue, (2) the amino acid residue corresponding to residue X145 is an aromatic residue or leucine, and (3) the amino acid residue corresponding to residue X190 is a cysteine or a constrained residue. In some embodiments, the region or domain that corresponds to residues 90-211 of sequence formula of SEQ ID NO: 61, 62 or 63 has at least the following features in the domain: (1) the amino acid residue corresponding to X94 is aspartic acid or glutamic acid, (2) the amino acid residue corresponding to X145 is tyrosine, tryptophan, phenylalanine, or leucine, and (3) the amino acid residue corresponding to X190 is cysteine or proline. In some embodiments, the region or domain that corresponds to residues 90-211 of sequence formula of SEQ ID NO: 61, 62 or 63 has at least the following features: (1) the amino acid residue corresponding to position 94 is aspartic acid, (2) the amino acid residue corresponding to position 145 is phenylalanine, tyrosine, or leucine, particularly phenylalanine or leucine, and (3) the amino acid corresponding to position 190 is proline. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the corresponding domain of a reference sequence based on SEQ ID NO: 2, 4, or 60. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:2, 4 or 60 with the preceding features.

In some embodiments, the ketoreductase polypeptides with a region corresponding to residues 90-211 and having the specified features for residues X94, X145 and X190 as described herein, can further include in the domain one or more features selected from the following: residue corresponding to X96 is a polar, constrained, non-polar or aliphatic residue; residue corresponding to X108 is hydrophilic, polar or constrained residue; residue corresponding to X109 is an acidic residue; residue corresponding to X147 is an aromatic, non-polar, aliphatic, or hydrophobic residue; residue corresponding to X152 is a polar residue; residue corresponding to X153 is a polar, non-polar, or aliphatic residue; residue corresponding to X157 is a polar residue; residue corresponding to X195 is a non-polar, aliphatic, or basic residue; residue corresponding to X196 is a non polar or aliphatic residue; residue corresponding to X198 is an acidic, polar residue, hydrophilic residue; residue corresponding to X199 is an acidic, basic, hydrophilic, aliphatic or nonpolar residue; and residue corresponding to X206 is a nonpolar, aromatic, or hydrophobic residue. In some of the foregoing embodiments, the residue corresponding to X94 is aspartic acid; the residue corresponding to X145 is phenylalanine, tyrosine, or leucine, particularly phenylalanine; and the residue corresponding to X190 is cysteine or proline, particularly proline. In some embodiments, the domain or region corresponding to residues 90-211 can have additionally one or more of the residues not specified by an X to be conservatively mutated. In some embodiments, the region or domain corresponding to residues 90-211 can have additionally from about 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the corresponding domain of a reference sequence based on SEQ ID NO:2, 4 or 60. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations.

In some embodiments, the ketoreductases polypeptides having a domain with an amino acid sequence corresponding to residues 90-211 based on sequence formula of SEQ ID NO: 61, 62, or 63, as described above, where the domain can have one or more conservative mutations as compared to the amino acid sequences of the corresponding domain of SEQ ID NO: 2, 4 or 60. Examples of such conservative mutations include amino acid replacements such as, but limited to: replacement of residue X152 threonine (T) with another polar residue, e.g., asparagine (N); replacement of residue X153 with another aliphatic or non-polar residue, e.g., valine; replacement of residue X157 asparagine (N) with another polar residue, e.g., serine (S); replacement of residue 185 threonine (T) with another polar residue, e.g., serine (S); replacement of residue X195 leucine (L) with another aliphatic or non-polar residue, e.g., methionine (M); replacement of residue X196 valine (V) with another non polar, hydrophobic, or aliphatic residue, e.g., leucine (L) or isoleucine (I); replacement of residue X199 leucine (L) with another non-polar or aliphatic residue, e.g., valine (V).

In some embodiments, the ketoreductase polypeptides with a region corresponding to residues 90-211 and having the specified features for residues X94, X145 and X190 as described herein, can further include in the region or domain one or more features selected from the following: residue corresponding to X96 is proline, serine, threonine, asparagine, glutamine, glycine, methionine, alanine, valine, leucine, or isoleucine, particularly valine, proline, or glycine; residue corresponding to X108 is threonine, serine, histidine, glutamic acid, asparagine, glutamine, aspartic acid, lysine, particularly histidine; residue corresponding to X109 is aspartic or glutamic acid; residue corresponding to X147 is isoleucine, phenylalanine, valine, leucine, tryptophan, methionine, alanine and tyrosine, particularly isoleucine, methionine, valine, or leucine; residue corresponding to X152 is serine, threonine, asparagine or glutamine, particularly asparagine; residue corresponding to X153 is alanine, valine, leucine, isoleucine, serine, threonine, asparagine, or glutamine, particularly valine; residue corresponding to X157 is serine, threonine, asparagine, or glutamine, particularly serine; residue corresponding to X195 is glycine, methionine, alanine, valine, leucine, or isoleucine, particularly methionine; residue corresponding to X196 is glycine, methionine, alanine, valine, leucine, isoleucine, particularly leucine; residue corresponding to X198 is aspartic acid, glutamic acid, serine, threonine, asparagine, or glutamine, particularly asparagine; residue corresponding to X199 is aspartic acid, glutamic acid, arginine, lysine, serine, threonine, asparagine, glutamine, glycine, methionine, alanine, valine, leucine, or isoleucine, particularly valine, arginine, or glutamic acid; residue corresponding to X206 is isoleucine, phenylalanine, valine, leucine, tryptophan, methionine, alanine or tyrosine, particularly tyrosine, tryptophan, or phenylalanine. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4 or 60. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations.

In some embodiments, the ketoreductase polypeptides with a region corresponding to residues 90-211 and having the specified features for residues X94, X145 and X190 as described herein, can further include in the region or domain at least the following features: residue corresponding to X147 is an aromatic, non-polar, aliphatic, or hydrophobic residue; and residue corresponding to X206 is nonpolar, aromatic, or hydrophobic residue. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4 or 60. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:2, 4 or 60 with the preceding features.

In some embodiments, the ketoreductase polypeptides with a region corresponding to residues 90-211 and having the specified features for residues X94, X145 and X190 as described herein, can further include in the region or domain at least the following features: residue corresponding to X96 is a polar, constrained, non-polar or aliphatic residue; residue corresponding to X147 is an aromatic, non-polar, aliphatic, or hydrophobic residue; residue corresponding to X199 is an acidic, basic, hydrophilic, aliphatic or nonpolar residue; and residue corresponding to X206 is a nonpolar, aromatic, or hydrophobic residue. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4 or 60. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:2, 4 or 60 with the preceding features.

In some embodiments, the ketoreductase polypeptides with a region corresponding to residues 90-211 and having the specified features for residues X94, X145 and X190 as described herein, can further include in the region or domain at least the following features: residue corresponding to X147 is an aromatic, non-polar, aliphatic, or hydrophobic residue; residue corresponding to X195 is a non-polar, aliphatic, or basic residue; residue corresponding to X196 is a non polar or aliphatic residue; and residue corresponding to X206 is a nonpolar, aromatic, or hydrophobic residue. In some of the foregoing embodiments, the amino acid residue corresponding to X94 is aspartic acid; the amino acid residue corresponding to X145 is phenylalanine, tyrosine, or leucine, particularly phenylalanine; and the amino acid corresponding to X190 is cysteine or proline, particularly proline. In some of the foregoing embodiments, the amino acid residue corresponding to X94 is aspartic acid; the amino acid residue corresponding to X145 is phenylalanine, tyrosine, or leucine, particularly phenylalanine or leucine; and the amino acid corresponding to X190 is cysteine or proline, particularly proline. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4 or 60. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:2, 4 or 60 with the preceding features.

In some embodiments, the ketoreductase polypeptides with a region corresponding to residues 90-211 and having the specified features for residues X94, X145 and X190 as described herein, can further include in the region or domain at least the following features: residue corresponding to X147 is isoleucine, phenylalanine, valine, leucine, tryptophan, methionine, alanine and tyrosine, particularly isoleucine, methionine, valine, or leucine; residue corresponding to X195 is glycine, methionine, alanine, valine, leucine, or isoleucine, particularly methionine; residue corresponding to X196 s glycine, methionine, alanine, valine, leucine, isoleucine, particularly leucine; and residue corresponding to X206 is isoleucine, phenylalanine, valine, leucine, tryptophan, methionine, alanine or tyrosine, particularly tyrosine, tryptophan, or phenylalanine. In some of the foregoing embodiments, the amino acid residue corresponding to X94 is aspartic acid; the amino acid residue corresponding to X145 is phenylalanine, tyrosine, or leucine, particularly phenylalanine; and the amino acid corresponding to X190 is cysteine or proline, particularly proline. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4 or 60. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:2, 4 or 60 with the preceding features.

In some embodiments, the ketoreductase polypeptides with a region corresponding to residues 90-211 and having the specified features for residues X94, X145 and X190 as described herein, can further include in the region or domain at least the following features: residue corresponding to X96 is a polar, constrained, non-polar or aliphatic residue; residue corresponding to X147 is an aromatic, non-polar, aliphatic, or hydrophobic residue; residue corresponding to X153 is a polar, non-polar, or aliphatic residue; residue corresponding to X195 is a non-polar, aliphatic, or basic residue; residue corresponding to X196 is a non polar or aliphatic residue; residue corresponding to X199 is an acidic, basic, hydrophilic, aliphatic or nonpolar residue; and residue corresponding to X206 is a nonpolar, aromatic, or hydrophobic residue. In some of the foregoing embodiments, the amino acid residue corresponding to X94 is aspartic acid; the amino acid residue corresponding to X145 is phenylalanine, tyrosine, or leucine, particularly phenylalanine; and the amino acid corresponding to X190 is cysteine or proline, particularly proline. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4 or 60. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:2, 4 or 60 with the preceding features.

In some embodiments, the ketoreductase polypeptides with a region corresponding to residues 90-211 and having the specified features for residues X94, X145 and X190 as described herein, can further include in the region or domain at least the following features: residue corresponding to X96 s proline, serine, threonine, asparagine, glutamine, glycine, methionine, alanine, valine, leucine, or isoleucine, particularly valine, proline, or glycine; residue corresponding to X147 is isoleucine, phenylalanine, valine, leucine, tryptophan, methionine, alanine and tyrosine, particularly isoleucine, methionine, valine, or leucine; residue corresponding to X153 is alanine, valine, leucine, isoleucine, serine, threonine, asparagine, or glutamine, particularly valine; residue corresponding to X195 is glycine, methionine, alanine, valine, leucine, or isoleucine, particularly methionine; residue corresponding to X196 is glycine, methionine, alanine, valine, leucine, isoleucine, particularly leucine; residue corresponding to X199 is aspartic acid, glutamic acid, arginine, lysine, serine, threonine, asparagine, glutamine, glycine, methionine, alanine, valine, leucine, or isoleucine, particularly valine, arginine, or glutamic acid; and residue corresponding to X206 is isoleucine, phenylalanine, valine, leucine, tryptophan, methionine, alanine or tyrosine, particularly tyrosine, tryptophan, or phenylalanine. In some of the foregoing embodiments, the amino acid residue corresponding to X94 is aspartic acid; the amino acid residue corresponding to X145 is phenylalanine, tyrosine, or leucine, particular phenylalanine or leucine; and the amino acid corresponding to X190 is cysteine or proline, particularly proline. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4 or 60. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:2, 4 or 60 with the preceding features.

In some embodiments, the ketoreductase polypeptides of the invention can comprise an amino acid sequence that is at least about 85%, 86%, 87%, 88%, 89%, 90%, 91%, 92%, 93%, 94%, 95%, 96%, 97%, 98%, or 99% identical to a reference sequence based on SEQ ID NO:2, 4 or 60, or a region or domain thereof, such as residues 90-211, with the proviso that the residue corresponding to position 94 is aspartic acid; the residue corresponding to position 145 is phenylalanine, tyrosine or leucine, particularly phenylalanine or leucine; the residue corresponding to position 190 is cysteine or proline, particularly proline; and wherein the polypeptide can additionally have one or more of the following substitutions such that the polypeptide is further improved (e.g., with respect to stereoselectivity, enzymatic activity, and/or thermostability) over the wild-type kefir ketoreductase or another engineered ketoreductase, such as SEQ ID NO:6: 7→H; 40→R; 46→R; 60→I; 64→V; 96→P, G,V; 108→H; 109→E; 147→M; 152→N,S; 153→A,V; 157→S; 195→R, M; 196→L; 198→N; 199→V,E,R; 206→F,W,Y; 226→V; 233→G,A; 245→I; and 249→W.

In some embodiments, the ketoreductase polypeptides of the invention can comprise a region having an amino acid sequence that is at least about 85%, 86%, 87%, 88%, 89%, 90%, 91%, 92%, 93%, 94%, 95%, 96%, 97%, 98%, or 99% identical to a reference sequence based on SEQ ID NO:2, 4 or 60, or a region or domain thereof, such as residues 90-211, with the proviso that the residue corresponding to position 94 is aspartic acid; the residue corresponding to position 145 is phenylalanine; the residue corresponding to position 190 is proline; and wherein the polypeptide can additionally have one or more of the following substitutions such that the polypeptide is further improved (with respect to stereoselectivity, enzymatic activity, and/or thermostability) over the wild-type kefir ketoreductase or another engineered ketoreductase (e.g., SEQ ID NO:6): 7→H; 40→R; 46→R; 60→I; 64→V; 96→P,G,V; 108→H; 109→E; 147→M; 152→N; 153→A,V; 157→S; 195→M; 196→L; 198→N; 199→V,E,R; 206→W; 226→V; 233→G; 245→I; and 249→W.

In some embodiments, the ketoreductase polypeptides of the invention can comprise an amino acid sequence that is at least about 85%, 86%, 87%, 88%, 89%, 90%, 91%, 92%, 93%, 94%, 95%, 96%, 97%, 98%, or 99% identical to a reference sequence based on SEQ ID NO:2, 4 or 60, or a region or domain thereof, such as residues 90-211, with the proviso that the residue corresponding to position 94 is aspartic acid; the residue corresponding to position 145 is phenylalanine, tyrosine or leucine, particularly phenylalanine or leucine; the residue corresponding to position 190 is cysteine or proline; the residue corresponding to position 40 is arginine, and wherein the polypeptide can additionally have one or more of the following substitutions such that the polypeptide is further improved (e.g., with respect to stereoselectivity, enzymatic activity, and/or thermostability) over the wild-type kefir ketoreductase or another engineered ketoreductase (e.g., such as SEQ ID NO:6): 46→R; 96→V; 99→E; 108→H; 147→M; 152→N; 153→V; 157→S; 195→M; 196→L; 199→V,E,R; 206→W; 226→V; 233→G; 245→I; and 249→W.

In some embodiments, the ketoreductase polypeptides of the invention can comprise a region having an amino acid sequence that is at least about 85%, 86%, 87%, 88%, 89%, 90%, 91%, 92%, 93%, 94%, 95%, 96%, 97%, 98%, or 99% identical to a reference sequence based on SEQ ID NO:2, 4 or 60, or a region or domain thereof, such as residues 90-211, with the proviso that the residue corresponding to position 94 is aspartic acid; the residue corresponding to position 145 is phenylalanine, tyrosine or leucine, particularly phenylalanine or leucine; the residue corresponding to position 190 is cysteine or proline, particularly proline; the residue corresponding to position 40 is arginine; the residue corresponding to position 147 is methionine, and wherein the polypeptide can additionally have one or more of the following substitutions such that the polypeptide is further improved (e.g., with respect to stereoselectivity, enzymatic activity, and/or thermostability) over the wild-type kefir ketoreductase or another engineered ketoreductase (such as SEQ ID NO:6): 46→R; 96→V; 108→H; 152→N; 153→V; 157→S; 195→M; 196→L; 199→V,E,R; 206→W; 226→V; 233→G; 245→I; and 249→W.

In some embodiments, the improved engineered ketoreductase enzymes comprise deletions of the naturally occurring ketoreductase polypeptides as well as deletions of other improved ketoreductase polypeptides. In some embodiments, each of the improved engineered ketoreductase enzymes described herein can comprise deletions of the polypeptides described herein. Thus, for each and every embodiment of the ketoreductase polypeptides of the disclosure, the deletions, which can be internal or external (i.e., C- and/or N-terminal truncations) deletions, can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids, or up to 30% of the total number of amino acids of the ketoreductase polypeptides, as long as the functional activity of the ketoreductase activity is maintained. In some embodiments, the deletions can comprise, 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 amino acid residues. In some embodiments, the number of deletions can be 1, 2, 3, 4, 5, 6, 7, 8, 9, 10, 11, 12, 14, 15, 16, 18, 20, 22, 24, 26, 30, 35 or about 40 amino acids. In some embodiments, the deletions can comprise deletions of 1, 2, 3, 4, 5, 6, 7, 8, 9, 10, 11, 12, 13, 14, 15, 16, 18, or 20 amino acid residues.

The present invention also provides fragments of the above-described improved engineered ketoreductase enzymes that exhibit ketoreductase activity where the amino acid sequence of the fragment comprises the following features: (a) the residue corresponding to residue X94 is aspartic acid, (b) the residue corresponding to residue X145 is tyrosine, tryptophan, phenylalanine, or leucine, particularly phenylalanine or leucine; and (c) the residue corresponding to residue X190 is a cysteine or proline, where amino acid position is determined by optimal alignment with a reference sequence selected from SEQ ID NO: 2, 4, or 60.

The polypeptides described herein are not restricted to the genetically encoded amino acids. In addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-stereomers of the genetically-encoded amino acids; 2,3-diaminopropionic acid (Dpr); α-aminoisobutyric acid (Aib); ε-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Ocf); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutanic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisolencine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (see, e.g., the various amino acids provided in Fasman, 1989, CRC Practical Handbook of Biochemistry and Molecular Biology, CRC Press, Boca Raton, FL, at pp. 3-70 and the references cited therein, all of which are incorporated by reference). These amino acids may be in either the L- or D-configuration.

Those of skill in the art will recognize that amino acids or residues bearing side chain protecting groups may also comprise the polypeptides described herein. Non-limiting examples of such protected amino acids, which in this case belong to the aromatic category, include (protecting groups listed in parentheses), but are not limited to: Arg(tos), Cys(methylbenzyl), Cys(nitropyridinesulfenyl), Glu(δ-benzylester), Gln(xanthyl), Asn(N-δ-xanthyl), His(bom), His (benzyl), His(tos), Lys(fmoc), Lys(tos), Ser(O-benzyl), Thr (O-benzyl) and Tyr(O-benzyl).

Non-encoding amino acids that are conformationally constrained of which the polypeptides described herein may be composed include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid.

The residues in the catalytic domain of L. kefir are S143, Y156, K160, and N114. The binding pocket domain residues are located at positions 94, 96, 153, 150, 144, 145, 190, 195, 196, 199, 202, 206, 211, and 249 in L. kefir KRED. Q252 is located in the $Mg^{2+}$ binding domain. Residues in the NADP binding domain are residues 14-20, 37-40, 62-64, 90-93, 113, 141, 188-191, 193, and 195. Sequence-activity analyses indicated that the specific substitutions described herein at positions 94, 145, and 190 were important with respect to the ability of the engineered ketoreductase polypeptides described herein to stereoselectively reduce the substrate N-methyl-3-keto-3-(2-thienyl)-1-propanamine to (S)—N-methyl-3-hydroxy-3-(2-thienyl)-1-propanamine at a high percent stereomeric excess. These positions directly interact with the substrate in the binding pocket of the ketoreductase.

Polynucleotides Encoding Engineered Ketoreductases

In another aspect, the present disclosure provides polynucleotides encoding the engineered ketoreductase enzymes. The polynucleotides may be operatively linked to one or more heterologous regulatory sequences that control gene expression to create a recombinant polynucleotide capable of expressing the polypeptide. Expression constructs containing a heterologous polynucleotide encoding the engineered ketoreductase can be introduced into appropriate host cells to express the corresponding ketoreductase polypeptide.

Because of the knowledge of the codons corresponding to the various amino acids, availability of a protein sequence provides a description of all the polynucleotides capable of encoding the subject. The degeneracy of the genetic code, where the same amino acids are encoded by alternative or synonymous codons allows an extremely large number of nucleic acids to be made, all of which encode the improved ketoreductase enzymes disclosed herein. Thus, having identified a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made by selecting combinations based on the possible codon choices, and all such variations are to be considered specifically disclosed for any polypeptide disclosed herein, including the amino acid sequences presented in Table 2. In various embodiments, the codons are preferably selected to fit the host cell in which the protein is being produced. For example, preferred codons used in bacteria are used to express the gene in bacteria; preferred codons used in yeast are used for expression in yeast; and preferred codons used in mammals are used for expression in mammalian cells. By way of example, the polynucleotide of SEQ ID NO: 1 has been codon optimized for expression in E. coli, but otherwise encodes the naturally occurring ketoreductase of Lactobacillus kefir.

In some embodiments, the polynucleotide comprises a nucleotide sequence encoding a ketoreductase polypeptide with an amino acid sequence that has at least about 85%, 86%, 87%, 88%, 89%, 90%, 91%, 92%, 93%, 94%, 95%, 96%, 97%, 98%, or 99% or more sequence identity to any of the reference engineered ketoreductase polypeptides described herein, where the encoded ketoreductase polypeptide comprises an amino acid sequence that has at least the following features: (1) the amino acid residue corresponding to residue position 94 of SEQ ID NO:2, 4 or 60 is an acidic amino acid, (2) the amino acid residue corresponding to residue position 145 of SEQ ID NO:2, 4 or 60 is an aromatic amino acid or leucine, and (3) the amino acid residue corresponding to residue position 190 of SEQ ID NO:2, 4 or 60 is a cysteine or a constrained amino acid. In some embodiments, the polynucleotides with the specified sequence identity above encode ketoreductase polypeptides having at least the following features: (1) the amino acid residue corresponding to position 94 is aspartic acid, (2) the amino acid residue corresponding to position 145 is tyrosine, tryptophan, phenylalanine, or leucine, particularly phenylalanine or leucine, and (3) the amino acid residue corresponding to position 190 is cysteine or proline. In some embodiments, the polynucleotides with the above specified sequence identity encode ketoreductase polypeptides having at least the following features: (1) the amino acid residue corresponding to position 94 is aspartic acid, (2) the amino acid residue corresponding to position 145 is phenylalanine or leucine, and (3) the amino acid corresponding to position 190 is cysteine or proline, particularly proline. In some embodiments, the polynucleotides encode an engineered ketoreductase polypeptide comprising an amino acid sequence selected from SEQ ID NOS: SEQ ID NO: 8, 10, 12, 14, 16, 18, 20, 22, 24, 26, 28, 30, and 32.

In some embodiments, the polynucleotides encoding the engineered ketoreductases are selected from SEQ ID NO: 7, 9, 11, 13, 15, 17, 19, 21, 23, 25, 27, 29, and 31. In some embodiments, the polynucleotides are capable of hybridizing under highly stringent conditions to a polynucleotide selected from SEQ ID NO: 7, 9, 11, 13, 15, 17, 19, 21, 23, 25, 27, 29, and 31, where the polynucleotide that hybridizes under highly stringent conditions encode a functional ketoreductase capable of converting the substrate of structural formula (I) to the product of structural formula (II), including, for example, the substrate having the structural formula (III) to the product having the structural formula (IV).

In some embodiments, the polynucleotides encode the polypeptides described herein but have about 80% or more sequence identity, about 85%, 86%, 87%, 88%, 89%, 90%, 91%, 92%, 93%, 94%, 95%, 96%, 97%, 98%, or 99% or more sequence identity at the nucleotide level to a reference polynucleotide encoding the engineered ketoreductase. In some embodiments, the reference polynucleotide is selected from polynucleotide sequences represented by SEQ ID NO: 7, 9, 11, 13, 15, 17, 19, 21, 23, 25, 27, 29, and 31.

An isolated polynucleotide encoding an improved ketoreductase polypeptide may be manipulated in a variety of ways to provide for expression of the polypeptide. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., 2001, *Molecular Cloning: A Laboratory Manual*, 3$^{rd}$ Ed., Cold Spring Harbor Laboratory Press; and *Current Protocols in Molecular Biology*, Ausubel. F. ed., Greene Pub. Associates, 1998, updates to 2006, which are incorporated herein by reference.

For bacterial host cells, suitable promoters for directing transcription of the nucleic acid constructs of the present disclosure, include the promoters obtained from the *E. coli* lac operon, trp operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (See, Villa-Kamaroff et al., 1978, *Proc. Natl Acad. Sci. USA* 75: 3727-3731, which is incorporated herein by reference), as well as the tac promoter (DeBoer et al., 1983, *Proc. Natl Acad. Sci. USA* 80: 21-25, which is incorporated herein by reference). In some embodiments, the promoters can be those based on bacteriophage promoters, such as phage a promoters. Further promoters are described in Sambrook et al., supra, which is incorporated herein by reference.

For filamentous fungal host cells, suitable promoters for directing the transcription of the nucleic acid constructs of the present disclosure include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8:423-488, which is incorporated herein by reference.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra, which is incorporated herein by reference.

The control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are described by Guo and Sherman, 1995, *Mol Cell Bio* 15:5983-5990, which is incorporated herein by reference.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region.

Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NC1B 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiol Rev* 57: 109-137, which is incorporated herein by reference.

Effective signal peptide coding regions for filamentous fungal host cells can be the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells can be from the genes for *Saccharomyces cerevisiae* alpha-factor and *Saccharomyces cerevisiae* invertase. Other useful signal peptide coding regions are described by Romanos et al., 1992, supra, which is incorporated herein by reference.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (See, WO 95/33836, which is incorporated herein by reference).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter.

Other examples of regulatory sequences are those which allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the KRED polypeptide of the present invention would be operably linked with the regulatory sequence.

Thus, in another embodiment, the present disclosure is also directed to a recombinant expression vector comprising a polynucleotide encoding an engineered ketoreductase polypeptide or a variant thereof, and one or more expression regulating regions such as a promoter and a terminator, a replication origin, etc., depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present disclosure may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The expression vector of the present invention preferably contains one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol (Example 1) or tetracycline resistance. Suitable markers for yeast host cells are ADE2, HIS3, LEU2, LYS2, MET3, TRP1, and URA3.

Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus*.

The expression vectors of the present invention preferably contain an element(s) that permits integration of the vector into the host cell's genome or autonomous replication of the vector in the cell independent of the genome. For integration into the host cell genome, the vector may rely on the nucleic acid sequence encoding the polypeptide or any other element of the vector for integration of the vector into the genome by homologous or nonhomologous recombination.

Alternatively, the expression vector may contain additional nucleic acid sequences for directing integration by homologous recombination into the genome of the host cell. The additional nucleic acid sequences enable the vector to be integrated into the host cell genome at a precise location (s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are P15A on (as shown in the plasmid of FIG. 5) or the origins of replication of plasmids pBR322, pUC19, pACYC177 (which plasmid has the P15A ori), or pACYC184 permitting replication in *E. coli*, and pUB 110, pE194, pTA1060, or pAM□1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes it's functioning temperature-sensitive in the host cell (see, e.g., Ehrlich, 1978, *Proc Nal Acad Sci. USA* 75:1433, which is incorporated herein by reference).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

Many of the expression vectors for use in the present invention are commercially available. Suitable commercial expression vectors include p3×FLAG™™ expression vectors from Sigma-Aldrich Chemicals, St. Louis MO., which includes a CMV promoter and hGH polyadenylation site for expression in mammalian host cells and a pBR322 origin of replication and ampicillin resistance markers for amplification in *E. coli*. Other suitable expression vectors are pBluescriptII SK(-) and pBK-CMV, which are commercially available from Stratagene, LaJolla CA, and plasmids which are derived from pBR322 (Gibco BRL), pUC (Gibco BRL), pREP4, pCEP4 (Invitrogen) or pPoly (See Lathe et al., 1987, *Gene* 57:193-201, which is incorporated herein by reference).

Host Cells for Expression of Ketoreductase Polypeptides

In another aspect, the present disclosure provides a host cell comprising a polynucleotide encoding an improved ketoreductase polypeptide of the present disclosure, the polynucleotide being operatively linked to one or more control sequences for expression of the ketoreductase enzyme in the host cell. Host cells for use in expressing the KRED polypeptides encoded by the expression vectors of the present invention are well known in the art and include but are not limited to, bacterial cells, such as *E. coli, Lactobacillus kefir, Lactobacillus brevis, Lactobacillus minor, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Appropriate culture mediums and growth conditions for the above-described host cells are well known in the art.

Polynucleotides for expression of the ketoreductase may be introduced into cells by various methods known in the art. Techniques include among others, electroporation, biolistic particle bombardment, liposome mediated transfection, calcium chloride transfection, and protoplast fusion. Various methods for introducing polynucleotides into cells will be apparent to the skilled artisan.

As described in Example 1, an exemplary host cell is *Escherichia coli* W3110. In Example 1, the expression vector was created by operatively linking a polynucleotide encoding an improved ketoreductase into the plasmid pCK110900 operatively linked to the lac promoter under control of the lacI repressor. The expression vector also contained the P15a origin of replication and the chloramphenicol resistance gene. Cells containing the subject polynucleotide in *Escherichia coli* W3110 were isolated by subjecting the cells to chloramphenicol selection.

Methods of Generating Engineered Ketoreductase Polypeptides.

In some embodiments, to make the improved KRED polynucleotides and polypeptides of the present disclosure, the naturally-occurring ketoreductase enzyme that catalyzes the reduction reaction is obtained (or derived) from *Lactobacillus kefir* or *Lactobacillus brevis* or *Lactobacillus minor*. In some embodiments, the parent polynucleotide sequence is codon optimized to enhance expression of the ketoreductase in a specified host cell. As an illustration, the parental polynucleotide sequence encoding the wild-type KRED polypeptide of *Lactobacillus kefir* was constructed from oligonucleotides prepared based upon the known polypeptide sequence of *Lactobacillus kefir* KRED sequence available in Genbank database (Genbank accession no. AAP94029 GI:33112056). The parental polynucleotide sequence, designated as SEQ ID NO: 1, was codon optimized for expression in *E. coli* and the codon-optimized polynucleotide cloned into an expression vector, placing the expression of the ketoreductase gene under the control of the lac promoter and lacI repressor gene. Clones expressing the active ketoreductase in *E. coli* were identified and the genes sequenced to confirm their identity. The sequence designated (SEQ ID NO:1) was the parent sequence utilized as the starting point for most experiments and library construction of engineered ketoreductases evolved from the *Lactobacillus kefir* ketoreductase.

The engineered ketoreductases can be obtained by subjecting the polynucleotide encoding the naturally occurring ketoreductase to mutagenesis and/or directed evolution methods, as discussed above. An exemplary directed evolution technique is mutagenesis and/or DNA shuffling as described in Stemmer, 1994, *Proc Natl Acad Sci USA* 91:10747-10751; WO 95/22625; WO 97/0078; WO 97/35966; WO 98/27230; WO 00/42651; WO 01/75767 and U.S. Pat. No. 6,537,746. Other directed evolution procedures that can be used include, among others, staggered extension process (StEP), in vitro recombination (Zhao et al., 1998, *Nat. Biotechnol.* 16:258-261), mutagenic PCR (Caldwell et al., 1994, *PCR Methods Appl.* 3:S136-S140), and cassette mutagenesis (Black et al., 1996, *Proc Natl Acad Sci USA* 93:3525-3529). All of which references are incorporated herein by reference.

The clones obtained following mutagenesis treatment are screened for engineered ketoreductases having a desired improved enzyme property. Measuring enzyme activity from the expression libraries can be performed using the standard biochemistry technique of monitoring the rate of decrease (via a decrease in absorbance or fluorescence) of NADH or NADPH concentration, as it is converted into $NAD^+$ or $NADP^+$. In this reaction, the NADH or NADPH is consumed (oxidized) by the ketoreductase as the ketoreductase reduces a ketone substrate to the corresponding hydroxyl group. The rate of decrease of NADH or NADPH concentration, as measured by the decrease in absorbance or fluorescence, per unit time indicates the relative (enzymatic) activity of the KRED polypeptide in a fixed amount of the lysate (or a lyophilized powder made therefrom). Where the improved enzyme property desired is thermal stability, enzyme activity may be measured after subjecting the enzyme preparations to a defined temperature and measuring the amount of enzyme activity remaining after heat treatments. Clones containing a polynucleotide encoding a ketoreductase are then isolated, sequenced to identify the nucleotide sequence changes (if any), and used to express the enzyme in a host cell.

Where the sequence of the engineered polypeptide is known, the polynucleotides encoding the enzyme can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides and oligonucleotides of the invention can be prepared by chemical synthesis using, e.g., the classical phosphoramidite method described by Beaucage et al., 1981, *Tet Lett* 22:1859-69, or the method described by Matthes et al., 1984, *EMBO J.* 3:801-05, e.g., as it is typically practiced in automated synthetic methods. According to the phosphoramidite method, oligonucleotides are synthesized, e.g., in an automatic DNA synthesizer, purified, annealed, ligated and cloned in appropriate vectors. In addition, essentially any nucleic acid can be obtained from any of a variety of commercial sources, such as The Midland Certified Reagent Company, Midland, TX, The Great American Gene Company, Ramona, CA, ExpressGen Inc. Chicago, IL, Operon Technologies Inc., Alameda, CA, and many others.

Engineered ketoreductase enzymes expressed in a host cell can be recovered from the cells and or the culture medium using any one or more of the well known techniques for protein purification, including, among others, lysozyme treatment, sonication, filtration, salting-out, ultra-centrifugation, and chromatography. Suitable solutions for lysing and the high efficiency extraction of proteins from bacteria, such as *E. coli*, are commercially available under the trade name CelLytic B™ from Sigma-Aldrich of St. Louis MO.

Chromatographic techniques for isolation of the ketoreductase polypeptide include, among others, reverse phase chromatography high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art.

In some embodiments, affinity techniques may be used to isolate the improved ketoreductase enzymes. For affinity chromatography purification, any antibody which specifically binds the ketoreductase polypeptide may be used. For the production of antibodies, various host animals, including but not limited to rabbits, mice, rats, etc., may be immunized by injection with a compound. The compound may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette Guerin) and *Corynebacterium parvum*.

Methods of Using the Engineered Ketoreductase Enzymes and Compounds Prepared Therewith In some embodiments, the invention provides a method for producing an (S)-3-aryl-3-hydroxypropanamine, the method comprising:

(a) providing a 3-aryl-3-ketopropanamine substrate having the structure of formula (I):

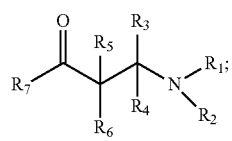

(I)

(b) contacting or incubating the 3-aryl-3-ketopropanamine substrate with one (or more) of the ketoreductase polypeptides described herein in a reaction mixture under conditions suitable for reduction or conversion of the substrate to an (S) 3-aryl-3-hydroxypropanime product having the structural formula (II):

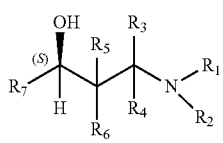

(II)

wherein for (I) and (II), $R_1$ and $R_2$ are each independently selected from the group consisting of hydrogen, an optionally substituted lower alkyl, an optionally substituted cycloalkyl, an optionally substituted aryl, or alternatively, where $R_1$ and $R_2$ together form an optionally substituted cycloalkyl or an optionally substituted cycloaryl having 3-7 carbon atoms; $R_3$, $R_4$, $R_5$, and $R_6$ are each independently selected from the group consisting of hydrogen and an optionally substituted lower alkyl; and $R_7$ is an optionally substituted aryl.

The resulting (S)-3-aryl-3-hydroxypropanamine may be recovered from step (b) and optionally purified using known methods.

Typically, for each of (I) and (II), $R_1$ and $R_2$ are each independently hydrogen, a lower alkyl of from one to ten or one to six carbon atoms, or a phenyl. Usually, one of $R_1$ and $R_2$ is hydrogen and the other is methyl or both $R_1$ and $R_2$ are methyl. Each of $R_3$, $R_4$, $R_5$, and $R_6$ is typically hydrogen or a lower alkyl of one to six carbon atoms, and more typically each of $R_3$, $R_4$, $R_5$, and $R_6$ is hydrogen. $R_7$ is typically an optionally substituted thiophenyl (such as, for example, an optionally substituted 2-thienyl or an optionally 3-thienyl) or an optionally substituted phenyl. More typically, $R_7$ is 2-thienyl or phenyl. Usually, $R_7$ is 2-thienyl. In certain exemplary substrates/products, $R_1$ is hydrogen, $R_2$ is methyl, $R_3$-$R_6$ are each hydrogen, $R_7$ is selected from the group consisting of 2-thienyl and phenyl; and $R_1$ and $R_2$ are methyl, $R_3$-$R_6$ are each hydrogen, $R_7$ is selected from the group consisting of 2-thienyl and phenyl.

In some embodiments, any one of the ketoreductase polypeptides provided herein can be used in the production of intermediates for the synthesis of Duloxetine (i.e., (3S)—N-methyl-3-naphthalen-1-yloxy-3-thiophen-2-yl-propan-1amine), a drug for the treatment of depression. In certain approaches to the synthesis of Duloxetine, an important step is the conversion of certain compounds of formula (I) to the corresponding compounds of formula (II).

More specifically, the ketoreductase enzymes described herein can catalyze the reduction of the substrate compound of structural formula (III), N-methyl-3-keto-3-(2-thienyl)-1-propanamine ("the monomethyl substrate", i.e., with respect to formula (I), one of $R_1$ and $R_2$ is hydrogen and the other is methyl, $R_3$, $R_4$, $R_5$, and $R_6$ are each hydrogen, and $R_7$ is 2-thienyl):

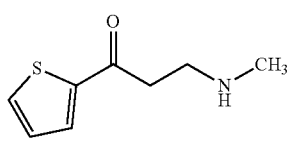

(III)

to the corresponding stereoisomeric alcohol product of structural formula (IV), (S)—N-methyl-3-hydroxy-3-(2-thienyl)-1-propanamine ("the monomethyl product", i.e., with respect to formula (II), one of $R_1$ and $R_2$ is hydrogen and the other is methyl, $R_3$, $R_4$, $R_5$, and $R_6$ are each hydrogen, and $R_7$ is 2-thienyl):

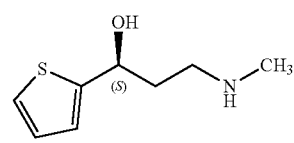

(IV)

The ketoreductase polypeptides described herein are also useful for catalyzing the reduction of the substrate compound of structural formula (V), N,N-dimethyl-3-keto-3-(2-thienyl)-1-propanamine ("the dimethyl substrate", i.e., with respect to formula (I), $R_1$ and $R_2$ are each methyl, $R_3$, $R_4$, $R_5$, and $R_6$ are each hydrogen, and $R_7$ is 2-thienyl):

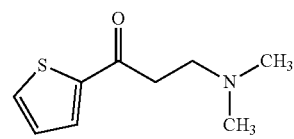

(V)

to the stereoisomeric alcohol product of structural formula (VI), (S)—N,N-dimethyl-3-hydroxy-3-(2-thienyl)-1-propanamine ("the dimethyl product", i.e., with respect to formula (II), $R_1$ and $R_2$ are each methyl, $R_3$, $R_4$, $R_5$, and $R_6$ are each hydrogen, and $R_7$ is 2-thienyl):

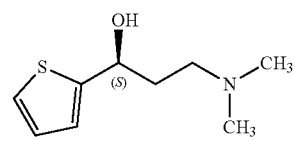

(VI)

Products (IV) and (VI) are both useful as intermediates in the synthesis of Duloxetine.

For instance, in some embodiments of this method for reducing the substrate, i.e. the monomethyl substrate) to the corresponding product, the ketoreductase polypeptide useful in the method has, as compared to the wild-type *L. kefir* or *L. brevis* or *L. minor* KRED sequences of SEQ ID NO: 2, 4 or 60, an amino acid sequence with at least the following features: (1) residue corresponding to X94 is an acidic residue, (2) residue corresponding to X145 is an aromatic residue or leucine, and (3) residue corresponding to X190 is a cysteine or a constrained residue. In some embodiments, the ketoreductase polypeptide has, as compared to the wild-type *L. kefir* or *L. brevis* or *L. minor* KRED sequences of SEQ ID NO:2, 4 or 60, at least the following features: (1) residue 40 is an aspartic acid, (2) residue 190 is a phenylalanine or leucine, and (3) residue corresponding to X190 is a cysteine or proline. As noted herein, the polynucleotides can encode a ketoreductase polypeptide with the foregoing features, and have in addition, one or more mutations at other amino acid residues as compared to the references sequences of SEQ ID NO:2, 4, or 60.

In some embodiments of this method for reducing the monomethyl substrate to the monomethyl product, the substrate is reduced to the product in greater than about 99% stereomeric excess, wherein the ketoreductase polypeptide comprises a sequence that corresponds to SEQ ID NO: 8, 10, 12, 14, 16, 18, 20, or 22.

In some embodiments of this method for reducing the monomethyl substrate to the corresponding monomethyl product, at least about 95% of the substrate is converted to the product in less than about 24 hours when carried out with greater than about 100 g/L of substrate and less than about 5 g/L of the polypeptide, wherein the polypeptide comprises an amino acid sequence corresponding to SEQ ID NO: 24, 26, 28, or 32.

In some embodiments of this method for reducing the monomethyl substrate to the product, at least about 10-20% of 1 g/L substrate is converted to the corresponding monomethyl product in less than about 24 hours with about 10 g/L of the polypeptide, wherein the polypeptide comprises an amino acid sequence corresponding to 12, 14, 16, 18, 22, 24, 26, 28, 30, or 32.

In some embodiments, the method for catalyzing the reduction of the 3-aryl-3-ketopropanamine substrate compound of structural formula (I), to the stereoisomeric alcohol product of structural formula (II) comprises contacting the ketoreductase polypeptide under reaction conditions in which the pH is about 8 or below. In some embodiments, the reaction condition is a pH from about 4 to 8. In some embodiments, the reaction condition is a pH of about 6 to 8. In some embodiments, the reaction condition is a pH of about 6.5.

In some embodiments, the reduction of the substrate compound of structural formula (I) to the corresponding alcohol product of structural formula (II) is carried out in the presence of isopropyl alcohol (IPA). In some embodiments, the IPA is present at >50% v/v. In some embodiments, the IPA in the reaction is present at least about 75% v/v. In some embodiments, the IPA is present at least about 90% v/v. In some embodiments, the reaction condition is from about pH 9 to about 10 and has ≥75% v/v of IPA.

In some embodiments where the substrate is N,N-dimethyl-3-keto-3-(2-thienyl)-1-propanamine, the reaction condition is chosen to reduce or minimize the formation of side products, such as 1-(thiophen-2-yl)prop-2-en-1-one); 1(thiophen-2-yl)propan-1-one; 1-(thiophen-2-yl)propan-1-ol; and 1-(thiophen-2-yl)prop-2-en-1-ol.

As is known by those of skill in the art, ketoreductase-catalyzed reduction reactions typically require a cofactor. Reduction reactions catalyzed by the engineered ketoreductase enzymes described herein also typically require a cofactor, although many embodiments of the engineered ketoreductases require far less cofactor than reactions catalyzed with wild-type ketoreductase enzymes. As used herein, the term "cofactor" refers to a non-protein compound that operates in combination with a ketoreductase enzyme. Cofactors suitable for use with the engineered ketoreductase enzymes described herein include, but are not limited to, NADP$^+$ (nicotinamide adenine dinucleotide phosphate), NADPH (the reduced form of NADP$^+$), NAD$^+$ (nicotinamide adenine dinucleotide) and NADH (the reduced form of NAD$^+$). Generally, the reduced form of the cofactor is added to the reaction mixture. The reduced NAD(P)H form can be optionally regenerated from the oxidized NAD(P)$^+$ form using a cofactor regeneration system.

The term "cofactor regeneration system" refers to a set of reactants that participate in a reaction that reduces the oxidized form of the cofactor (e.g., NADP$^+$ to NADPH). Cofactors oxidized by the ketoreductase-catalyzed reduction of the keto substrate are regenerated in reduced form by the cofactor regeneration system. Cofactor regeneration systems comprise a stoichiometric reductant that is a source of reducing hydrogen equivalents and is capable of reducing the oxidized form of the cofactor. The cofactor regeneration system may further comprise a catalyst, for example an enzyme catalyst, that catalyzes the reduction of the oxidized form of the cofactor by the reductant. Cofactor regeneration systems to regenerate NADH or NADPH from NAD$^+$ or NADP$^+$, respectively, are known in the art and may be used in the methods described herein.

The terms "secondary alcohol dehydrogenase" and "sADH" are used interchangeably herein to refer to an NAD$^+$ or NADP$^+$-dependent enzyme that catalyzes the conversion of a secondary alcohol and NAD$^+$ or NADP$^+$ to a ketone and NADH or NADPH, respectively. Scheme (1), below, describes the reduction of NAD$^+$ or NADP$^+$ by a secondary alcohol, illustrated by isopropanol.

Scheme (1)

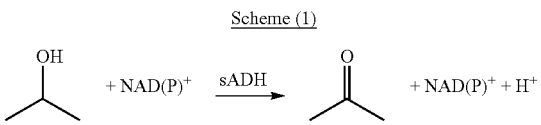

Secondary alcohol dehydrogenases that are suitable for use as cofactor regenerating systems in the ketoreductase-catalyzed reduction reactions described herein include both naturally occurring secondary alcohol dehydrogenases, as well as non-naturally occurring secondary alcohol dehydrogenases. Naturally occurring secondary alcohol dehydrogenases include known alcohol dehydrogenases from, *Thermoanaerobium brockii, Rhodococcus erythropolis, Lactobacillus kefir, Lactobacillus minor* and *Lactobacillus brevis*, and non-naturally occurring secondary alcohol dehydrogenases include engineered alcohol dehdyrogenases derived therefrom. Secondary alcohol dehydrogenases employed in the methods described herein, whether naturally occurring or non-naturally occurring, may exhibit an activity of at least about 1 μmol/min/mg, sometimes at least about 10 μmol/min/mg, or at least about 10$^2$ μmol/min/mg, up to about 10$^3$ μmol/min/mg or higher.

Suitable secondary alcohols include lower secondary alkanols and aryl-alkyl carbinols. Examples of lower secondary alcohols include isopropanol, 2-butanol, 3-methyl-2-butanol, 2-pentanol, 3-pentanol, 3,3-dimethyl-2-butanol, and the like. In some embodiments, the secondary alcohol is isopropanol. Suitable aryl-akyl carbinols include unsubstituted and substituted 1-arylethanols.

When a secondary alcohol and secondary alcohol dehydrogenase are employed as the cofactor regeneration system, the resulting NAD$^+$ or NADP$^+$ is reduced by the coupled oxidation of the secondary alcohol to the ketone by the secondary alcohol dehydrogenase. Some engineered ketoreductases also have activity to dehydrogenate a secondary alcohol reductant. In some embodiments using secondary alcohol as reductant, the engineered ketoreductase and the secondary alcohol dehydrogenase are the same enzyme.

Accumulation of acetone generated by reduction of isopropanol by the KRED enzymes of the invention can prevent the desired reaction (reduction of N-methyl-3-keto-3-(2-thienyl)-1-propanamine to (S)—N-methyl-3-hydroxy-3-(2-thienyl)-1-propanamine) from going to completion. Accordingly, in certain embodiments, the desired reduction reaction is carried out at reduced pressure (e.g. at 100 Torr) to remove acetone from the reaction mixture by distillation. In such embodiments, isopropanol can be added to the ongoing reaction to replenish that consumed by reduction to acetone as well as that lost by distillation under reduced pressure.

Suitable exemplary cofactor regeneration systems that may be employed may include, but are not limited to, glucose and glucose dehydrogenase, formate and formate dehydrogenase, glucose-6-phosphate and glucose-6-phosphate dehydrogenase, a secondary (e.g., isopropanol) alcohol and secondary alcohol dehydrogenase, phosphite and phosphite dehydrogenase, molecular hydrogen and hydrogenase, and the like. These systems may be used in combination with either NADP$^+$/NADPH or NAD$^+$/NADH as the cofactor. Electrochemical regeneration using hydrogenase may also be used as a cofactor regeneration system. See, e.g., U.S. Pat. Nos. 5,538,867 and 6,495,023, both of which are incorporated herein by reference. Chemical cofactor regeneration systems comprising a metal catalyst and a reducing agent (for example, molecular hydrogen or formate) are also suitable. See, e.g., PCT publication WO 2000/053731, which is incorporated herein by reference.

The terms "glucose dehydrogenase" and "GDH" are used interchangeably herein to refer to an NAD$^+$ or NADP$^+$-dependent enzyme that catalyzes the conversion of D-glucose and NAD$^+$ or NADP$^+$ to gluconic acid and NADH or NADPH, respectively. Equation (1), below, describes the glucose dehydrogenase-catalyzed reduction of NAD$^+$ or NADP$^+$ by glucose:

Glucose dehydrogenases that are suitable for use in the practice of the methods described herein include both naturally occurring glucose dehydrogenases, as well as non-naturally occurring glucose dehydrogenases. Naturally occurring glucose dehydrogenase encoding genes have been reported in the literature. For example, the *Bacillus subtilis* 61297 GDH gene was expressed in *E. coli* and was reported to exhibit the same physicochemical properties as the enzyme produced in its native host (Vasantha et al., 1983, *Proc. Natl. Acad. Sci. USA* 80:785). The gene sequence of the *B. subtilis* GDH gene, which corresponds to Genbank Acc. No. M12276, was reported by Lampel et al., 1986, *J. Bacteriol.* 166:238-243, and in corrected form by Yamane et al., 1996, *Microbiology* 142:3047-3056 as Genbank Acc. No. D50453. Naturally occurring GDH genes also include those that encode the GDH from *B. cereus* ATCC 14579 (Nature, 2003, 423:87-91; Genbank Acc. No. AE017013) and *B. megaterium* (*Eur. J. Biochem.*, 1988, 174:485-490, Genbank Acc. No. X12370; *J. Ferment. Bioeng.*, 1990, 70:363-369, Genbank Acc. No. GI216270). Glucose dehydrogenases from *Bacillus* sp. are provided in PCT publication WO 2005/018579 as SEQ ID NOS: 10 and 12 (encoded by polynucleotide sequences corresponding to SEQ ID NOS: 9 and 11, respectively, of the PCT publication), the disclosure of which is incorporated herein by reference. FIG. 1 depicts the conversion of the substrate compound of formula (III) to the corresponding product of formula (IV) using cofactors NAD(P)H/NAD(P)+ and a glucose/glucose dehydrogenase cofactor recycling system.

Non-naturally occurring glucose dehydrogenases may be generated using known methods, such as, for example, mutagenesis, directed evolution, and the like. GDH enzymes having suitable activity, whether naturally occurring or non-naturally occurring, may be readily identified using the assay described in Example 4 of PCT publication WO 2005/018579, the disclosure of which is incorporated herein by reference. Exemplary non-naturally occurring glucose dehydrogenases are provided in PCT publication WO 2005/018579 as SEQ ID NOS: 62, 64, 66, 68, 122, 124, and 126. The polynucleotide sequences that encode them are provided in PCT publication WO 2005/018579 as SEQ ID NOS: 61, 63, 65, 67, 121, 123, and 125, respectively. All of these sequences are incorporated herein by reference. Additional non-naturally occurring glucose dehydrogenases that are suitable for use in the ketoreductase-catalyzed reduction reactions disclosed herein are provided in U.S. application publication Nos. 2005/0095619 and 2005/0153417, the disclosures of which are incorporated herein by reference.

Glucose dehydrogenases employed in the ketoreductase-catalyzed reduction reactions described herein may exhibit an activity of at least about 10 μmol/min/mg and sometimes at least about $10^2$ μmol/min/mg or about $10^3$ μmol/min/mg, up to about $10^4$ μmol/min/mg or higher in the assay described in Example 4 of PCT publication WO 2005/018579.

The ketoreductase-catalyzed reduction reactions described herein are generally carried out in a solvent. Suitable solvents include water, organic solvents (e.g., ethyl acetate, butyl acetate, 1-octanol, heptane, octane, methyl t-butyl ether (MTBE), toluene, and the like), ionic liquids (e.g., 1-ethyl 4-methylimidazolium tetrafluoroborate, 1-butyl-3-methylimidazolium tetrafluoroborate, 1-butyl-3-methylimidazolium hexafluorophosphate, and the like). In some embodiments, aqueous solvents, including water and aqueous co-solvent systems, are used.

Exemplary aqueous co-solvent systems have water and one or more organic solvent. In general, an organic solvent component of an aqueous co-solvent system is selected such that it does not completely inactivate the ketoreductase enzyme. Appropriate co-solvent systems can be readily identified by measuring the enzymatic activity of the specified engineered ketoreductase enzyme with a defined substrate of interest in the candidate solvent system, utilizing an enzyme activity assay, such as those described herein.

The organic solvent component of an aqueous co-solvent system may be miscible with the aqueous component, providing a single liquid phase, or may be partly miscible or immiscible with the aqueous component, providing two liquid phases. Generally, when an aqueous co-solvent system is employed, it is selected to be biphasic, with water dispersed in an organic solvent, or vice-versa. Generally, when an aqueous co-solvent system is utilized, it is desirable to select an organic solvent that can be readily separated from the aqueous phase. In general, the ratio of water to organic solvent in the co-solvent system is typically in the range of from about 90:10 to about 10:90 (v/v) organic solvent to water, and between 80:20 and 20:80 (v/v) organic solvent to water. The co-solvent system may be pre-formed prior to addition to the reaction mixture, or it may be formed in situ in the reaction vessel.

The aqueous solvent (water or aqueous co-solvent system) may be pH-buffered or unbuffered. Generally, the reduction can be carried out at a pH of about 7 or below, usually in the range of from about 3 to about 7. In some embodiments, the reduction is carried out at a pH of about 6 or below, usually in the range of from about 4 to about 6. In some embodiments, the reduction is carried out at a pH of about 6 or below, often in the range of from about 5 to about 6. In a specific embodiment, the reduction may be carried out at pH 6.

During the course of the reduction reactions, the pH of the reaction mixture may change. The pH of the reaction mixture may be maintained at a desired pH or within a desired pH range by the addition of an acid or a base during the course of the reaction. Alternatively, the pH may be controlled by using an aqueous solvent that comprises a buffer. Suitable buffers to maintain desired pH ranges are known in the art and include, for example, phosphate buffer, triethanolamine buffer, and the like. Combinations of buffering and acid or base addition may also be used.

When a glucose/glucose dehydrogenase cofactor regeneration system is employed, the co-production of gluconic acid (pKa=3.6), as represented in equation (3) can cause the pH of the reaction mixture to drop if the resulting aqueous gluconic acid is not otherwise neutralized. The pH of the reaction mixture may be maintained at the desired level by standard buffering techniques, wherein the buffer neutralizes the gluconic acid up to the buffering capacity provided, or by the addition of a base concurrent with the course of the conversion. Combinations of buffering and base addition may also be used. Suitable buffers to maintain desired pH ranges are described above. Suitable bases for neutralization of gluconic acid are organic bases, for example amines, alkoxides and the like, and inorganic bases, for example, hydroxide salts (e.g., NaOH), carbonate salts (e.g., NaHCO$_3$), bicarbonate salts (e.g., K$_2$CO$_3$), basic phosphate salts (e.g., K$_2$HPO$_4$, Na$_3$PO$_4$), and the like. The addition of a base concurrent with the course of the conversion may be done manually while monitoring the reaction mixture pH or, more conveniently, by using an automatic titrator as a pH stat. A combination of partial buffering capacity and base addition can also be used for process control.

When base addition is employed to neutralize gluconic acid released during a ketoreductase-catalyzed reduction reaction, the progress of the conversion may be monitored by the amount of base added to maintain the pH. Typically, bases added to unbuffered or partially buffered reaction mixtures over the course of the reduction are added in aqueous solutions.

In some embodiments, the a co-factor regenerating system may comprise a formate dehydrogenase. The terms "formate dehydrogenase" and "FDH" are used interchangeably herein to refer to an NAD$^+$ or NADP$^+$-dependent enzyme that catalyzes the conversion of formate and NAD$^+$ or NADP$^+$ to carbon dioxide and NADH or NADPH, respectively. Formate dehydrogenases that may be suitable for use as cofactor regenerating systems in the ketoreductase-catalyzed reduction reactions described herein include both naturally occurring formate dehydrogenases, as well as non-naturally occurring formate dehydrogenases. Formate dehydrogenases include those corresponding to SEQ ID NOS: 70 (*Pseudomonas* sp.) and 72 (*Candida boidinii*) of PCT publication WO 2005/018579, which are encoded by polynucleotide sequences corresponding to SEQ ID NOS: 69 and 71, respectively, of PCT publication 2005/018579, the disclosures of which are incorporated herein by reference. Formate dehydrogenases that may be employed in the methods described herein, whether naturally occurring or non-naturally occurring, may exhibit an activity of at least about 1 µmol/min/mg, sometimes at least about 10 µmol/min/mg, or at least about 10$^2$ µmol/min/mg, up to about 10$^3$ µmol/min/mg or higher, and can be readily screened for activity in the assay described in Example 4 of PCT publication WO 2005/018579.

As used herein, the term "formate" refers to formate anion (HCO$_2$$^-$), formic acid (HCO$_2$H), and mixtures thereof. Formate may be provided in the form of a salt, typically an alkali or ammonium salt (for example, HCO$_2$Na, HCO$_2$NH$_4$, and the like), in the form of formic acid, typically aqueous formic acid, or mixtures thereof. Formic acid is a moderate acid. In aqueous solutions within several pH units of its pKa (pKa=3.7 in water) formate is present as both HCO$_2$$^-$ and HCO$_2$H in equilibrium concentrations. At pH values above about pH 4, formate is predominantly present as HCO$_2$$^-$. When formate is provided as formic acid, the reaction mixture is typically buffered or made less acidic by adding a base to provide the desired pH, typically of about pH 5 or above. Suitable bases for neutralization of formic acid include, but are not limited to, organic bases, for example amines, alkoxides and the like, and inorganic bases, for example, hydroxide salts (e.g., NaOH), carbonate salts (e.g., NaHCO$_3$), bicarbonate salts (e.g., K$_2$CO$_3$), basic phosphate salts (e.g., K$_2$HPO$_4$, Na$_3$PO$_4$), and the like.

For pH values above about pH 5, at which formate is predominantly present as HCO$_2$$^-$, Equation (2) below, describes the formate dehydrogenase-catalyzed reduction of NAD$^+$ or NADP$^+$ by formate:

$$HCO_2^- + NAD(P)^+ \xrightarrow{FDH} CO_2 + NAD(P)H$$

When formate and formate dehydrogenase are employed as the cofactor regeneration system, the pH of the reaction mixture may be maintained at the desired level by standard buffering techniques, wherein the buffer releases protons up to the buffering capacity provided, or by the addition of an acid concurrent with the course of the conversion. Suitable acids to add during the course of the reaction to maintain the pH include organic acids, for example carboxylic acids, sulfonic acids, phosphonic acids, and the like, mineral acids, for example hydrohalic acids (such as hydrochloric acid), sulfuric acid, phosphoric acid, and the like, acidic salts, for example dihydrogenphosphate salts (e.g., KH$_2$PO$_4$), bisulfate salts (e.g., NaHSO$_4$) and the like. Some embodiments utilize formic acid, whereby both the formate concentration and the pH of the solution are maintained.

When acid addition is employed to maintain the pH during a reduction reaction using the formate/formate dehydrogenase cofactor regeneration system, the progress of the conversion may be monitored by the amount of acid added to maintain the pH. Typically, acids added to unbuffered or partially buffered reaction mixtures over the course of conversion are added in aqueous solutions.

In carrying out embodiments of the ketoreductase-catalyzed reduction reactions described herein employing a cofactor regeneration system, either the oxidized or reduced form of the cofactor may be provided initially. As described above, the cofactor regeneration system converts oxidized cofactor to its reduced form, which is then utilized in the reduction of the ketoreductase substrate.

In some embodiments, cofactor regeneration systems are not used. For reduction reactions carried out without the use of a cofactor regenerating systems, the cofactor is added to the reaction mixture in reduced form.

In some embodiments, when the process is carried out using whole cells of the host organism, the whole cell may natively provide the cofactor. Alternatively or in combination, the cell may natively or recombinantly provide the glucose dehydrogenase.

In carrying out the stereoselective reduction reactions described herein, the engineered ketoreductase enzyme, and any enzymes comprising the optional cofactor regeneration system, may be added to the reaction mixture in the form of the purified enzymes, whole cells transformed with gene(s) encoding the enzymes, and/or cell extracts and/or lysates of such cells. The gene(s) encoding the engineered ketoreductase enzyme and the optional cofactor regeneration enzymes can be transformed into host cells separately or together into the same host cell. For example, in some embodiments one set of host cells can be transformed with gene(s) encoding the engineered ketoreductase enzyme and another set can be transformed with gene(s) encoding the cofactor regeneration enzymes. Both sets of transformed cells can be utilized together in the reaction mixture in the form of whole cells, or in the form of lysates or extracts derived therefrom. In other embodiments, a host cell can be transformed with gene(s) encoding both the engineered ketoreductase enzyme and the cofactor regeneration enzymes.

Whole cells transformed with gene(s) encoding the engineered ketoreductase enzyme and/or the optional cofactor regeneration enzymes, or cell extracts and/or lysates thereof, may be employed in a variety of different forms, including solid (e.g., lyophilized, spray-dried, and the like) or semi-solid (e.g., a crude paste).

The cell extracts or cell lysates may be partially purified by precipitation (ammonium sulfate, polyethyleneimine, heat treatment or the like, followed by a desalting procedure prior to lyophilization (e.g., ultrafiltration, dialysis, and the like). Any of the cell preparations may be stabilized by crosslinking using known crosslinking agents, such as, for example, glutaraldehyde or immobilization to a solid phase (e.g., Eupergit C, and the like).

The solid reactants (e.g., enzyme, salts, etc.) may be provided to the reaction in a variety of different forms, including powder (e.g., lyophilized, spray dried, and the like), solution, emulsion, suspension, and the like. The reactants can be readily lyophilized or spray dried using methods and equipment that are known to those having ordinary skill in the art. For example, the protein solution can be frozen at −80° C. in small aliquots, then added to a prechilled lyophilization chamber, followed by the application of a vacuum. After the removal of water from the samples, the temperature is typically raised to 4° C. for two hours before release of the vacuum and retrieval of the lyophilized samples.

The quantities of reactants used in the reduction reaction will generally vary depending on the quantities of product desired, and concomitantly the amount of ketoreductase substrate employed. The following guidelines can be used to determine the amounts of ketoreductase, cofactor, and optional cofactor regeneration system to use. Generally, keto substrates can be employed at a concentration of about 20 to 300 grams/liter using from about 50 mg to about 5 g of ketoreductase and about 10 mg to about 150 mg of cofactor. Those having ordinary skill in the art will readily understand how to vary these quantities to tailor them to the desired level of productivity and scale of production. Appropriate quantities of optional cofactor regeneration system may be readily determined by routine experimentation based on the amount of cofactor and/or ketoreductase utilized. In general, the reductant (e.g., glucose, formate, isopropanol) is utilized at levels above the equimolar level of ketoreductase substrate to achieve essentially complete or near complete conversion of the ketoreductase substrate.

The order of addition of reactants is not critical. The reactants may be added together at the same time to a solvent (e.g., monophasic solvent, biphasic aqueous co-solvent system, and the like), or alternatively, some of the reactants may be added separately, and some together at different time points. For example, the cofactor regeneration system, cofactor, ketoreductase, and ketoreductase substrate may be added first to the solvent.

For improved mixing efficiency when an aqueous co-solvent system is used, the cofactor regeneration system, ketoreductase, and cofactor may be added and mixed into the aqueous phase first. The organic phase may then be added and mixed in, followed by addition of the ketoreductase substrate. Alternatively, the ketoreductase substrate may be premixed in the organic phase, prior to addition to the aqueous phase Suitable conditions for carrying out the ketoreductase-catalyzed reduction reactions described herein include a wide variety of conditions which can be readily optimized by routine experimentation that includes, but is not limited to, contacting the engineered ketoreductase enzyme and substrate at an experimental pH and temperature and detecting product, for example, using the methods described in the Examples provided herein.

The ketoreductase catalyzed reduction is typically carried out at a temperature in the range of from about 15° C. to about 75° C. For some embodiments, the reaction is carried out at a temperature in the range of from about 20° C. to about 55° C. In still other embodiments, it is carried out at a temperature in the range of from about 20° C. to about 45° C. The reaction may also be carried out under ambient conditions.

The reduction reaction is generally allowed to proceed until essentially complete, or near complete, reduction of substrate is obtained. Reduction of substrate to product can be monitored using known methods by detecting substrate and/or product. Suitable methods include gas chromatography, HPLC, and the like. Conversion yields of the alcohol reduction product generated in the reaction mixture are generally greater than about 50%, may also be greater than about 60%, may also be greater than about 70%, may also be greater than about 80%, may also be greater than about 90%, and are often greater than about 97%.

The present invention provides a method for making an (S)—N-methyl-3-hydroxy-3-(aryl)-propanamine, the method comprising:

(a) providing a 3-aryl-3-ketopropanamine substrate having the structure of formula (I):

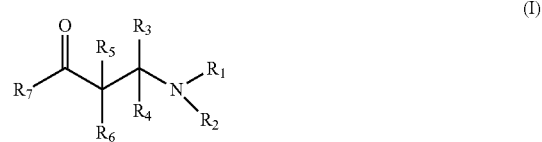

wherein $R_1$ and $R_2$ are each methyl, $R_3$, $R_4$, $R_5$, and $R_6$ are each independently selected from the group consisting of hydrogen and an optionally substituted lower alkyl, and $R_7$ is an optionally substituted aryl;

(b) contacting or incubating the 3-aryl-3-ketopropanamine substrate with one or more ketoreductase polypeptides of the present invention in a reaction mixture under conditions suitable for reduction or conversion of the substrate to an (S)-3-aryl-3-hydroxypropanamine product having the structural formula (II):

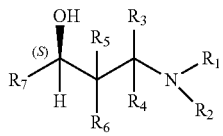
(II)

wherein $R_1$ and $R_2$ are each methyl, $R_3$, $R_4$, $R_5$, and $R_6$ are each independently selected from the group consisting of hydrogen and an optionally substituted lower alkyl, and $R_7$ is an optionally substituted aryl;

(c) demethylating the (S)-3-aryl-3-hydroxypropanamine (i.e., N,N-dimethyl-3-hydroxy-3-(aryl)-propanamine) product of step (b) in a reaction mixture under conditions suitable for producing an (S)—N-methyl-3-hydroxy-3-(aryl)-propanamine having the formula of structure (II):

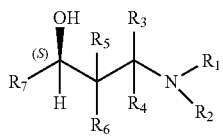
(II)

wherein one of $R_1$ and $R_2$ is methyl and the other is hydrogen, $R_3$, $R_4$, $R_5$, and $R_6$ are each independently selected from the group consisting of hydrogen and a an optionally substituted lower alkyl, and $R_7$ is an optionally substituted aryl.

The substituents $R_3$-$R_7$ are as described hereinabove for compounds having the structures of formula (I) and (II). Typically, $R_3$, $R_4$, $R_5$, and $R_6$ are all hydrogen and $R_7$ is an aryl selected from the group consisting of phenyl and a thienyl. Usually, $R_7$ is 2-thienyl.

Conditions suitable for producing the (S)—N-methyl-3-hydroxy-3-(aryl)-propanamine in step (b) include contacting the N,N-dimethyl-3-hydroxy-3-(aryl)-propanamine product of step (b) with a demethylating agent in the presence of a base to form an intermediate that is subjected to further hydrolysis to yield the (S)—N-methyl-3-hydroxy-3-(aryl)-propanamine product of step (c). The term "demethylating agent" refers herein to a compound that facilitates removal of a methyl group from an amine. Suitable demethylating agents include chloroformate and derivatives thereof, phosgene and derivatives thereof, and other suitable compounds that are well known in the art. Exemplary chloroformate derivatives include ethyl chloroformate, methyl chloroformate, propyl chloroformate, butyl chloroformate, i-butyl chloroformate, phenyl chloroformate, 2,2,2-trichloroethyl chloroformate, 2-chloroethyl chloroformate, 2-iodoethyl chloroformate, benzyl chloroformate, nitrobenzyl chloroformate, 1-chloroethyl chloroformate, 2,2-dichloroethyl chloroformate, 1,1-dimethyl-2,2,2-trichloroethyl chloroformate, 1,1-dimethyl-2-chloroethyl chloroformate, 1,1-dimethyl-2-bromoethyl chloroformate, and the like. Typically, the chloroformate derivative is i-butyl chloroformate or phenyl chloroformate. Phosgene derivatives suitable for use in the practice of the invention include diphosgene (i.e., trichloromethyl chloroformate), triphosgene (i.e., bis(trichloromethyl carbonate), and the like.

Suitable bases to use in conjunction with the demethylating agent include amines (e.g., trialkylamines such as triethylamine, trimethylamine, dialkylamines, and the like), hydroxides of an alkali metal or their salts with weak acid (such as, for example, sodium hydroxide, potassium hydroxide, sodium carbonate, sodium hydrogencarbonate, potassium carbonate, potassium hydrogencarbonate, cesium carbonate, tripotassium phosphate, tripotassium phosphate dehydrate, and the like), hydroxides of quaternary ammonium or their salts with a weak acid, and the like. Typically, the base is an amine, such as, for example, triethylamine.

The intermediate is prepared in a reaction mixture of the demethylating agent, base, and a solvent, such as, for example, a pyrrolidone, a ketone (e.g., acetone, ethyl methyl ketone, and the like), a dipolar aprotic solvent (e.g., dimethyl sulfoxide (DMSO), N-methyl-2-pyrrolidone, dimethylformamide, dimethylacetamide, and the like), an aromatic hydrocarbon (e.g., benzene, toluene, xylene, mesitylene, and the like), a nitrile (e.g., acetonitrile, and the like), an ether (e.g., t-butyl methyl ether, diisopropyl ether, tetrahydrofuran, 1,4-dioxane, 1,2-dimethoxyethane, anisole, and the like), an amide and the like, as well as combinations of any two or more thereof. Typically, the solvent is an aromatic hydrocarbon, such as, for example, toluene. If the solvent is not replaced for the subsequence hydrolysis step, the solvent is typically an aromatic hydrocarbon, such as, for example, benzene, toluene, xylene, and mesitylene, an ether, such as, for example, t-butyl methyl ether, diisopropyl ether, tetrahydrofuran, 1,4-dioxane, 1,2-dimethoxyethane and anisole, or any combination of two or more thereof.

The reaction is typically carried out at a temperature in the range of from about −30° C. to about 100° C. Typically, the reaction is carried out at a temperature in the range of from about 0° C. to about 90° C., and usually at a temperature in the range of from about 25° C. or 30° C. to about 80° C., and often at a temperature of about 75° C.

The subsequent hydrolysis reaction is carried out in the presence of a base and a solvent, such as, for example, an alcohol (e.g., methanol, ethanol, propanol, isopropanol, butanol, and the like), an amide, a pyrrolidone, a dipolar aprotic solvent (e.g., DMSO, N-methyl-2-pyrrolidone, dimethylformamide, dimethylacetamide, and the like), a ketone (e.g., acetone, ethyl methyl ketone, and the like), an aromatic hydrocarbon (e.g., benzene, toluene, xylene, mesitylene, and the like), and ether (e.g., butyl methyl ether, eiisopropyl ether, tetrahydrofuran, 1,4-dioxane, 1,2-dimethoxyethane, anisole, and the like), water, and the like, as well as any combination of two or more thereof. Aqueous co-solvent systems that are suitable for use in the hydrolysis system include water and an alcohol in a mixture of 25:75, 50:50, or 75:25 water:alcohol. Bases suitable for using in the hydrolysis step include a hydroxide of an alkali metal or salt thereof with a weak acid, a hydroxide of quaternary ammonium or salt thereof with a weak acid, and the like. Exemplary bases include sodium hydroxide, potassium hydroxide, sodium carbonate, sodium hydrogencarbonate, potassium carbonate, potassium hydrogencarbonate, cesium carbonate, tripotassium phosphate and tripotassium phosphate dihydrate. Typically, the hydrolysis is carried out using a hydroxide of an alkali metal, such as, for example, potassium or sodium, in a water-alcohol co-solvent system, such as for example water-methanol, water-isopropanol, and the like. Conditions suitable for carrying out demethylation are described in U.S. Patent Publication 2006/0167278, U.S. Pat. Nos. 5,023,269, 5,491,243, 6,541,668, WO 2007/095200, EP 0 457 559A2, and EP 0 273 658A1, all of which are incorporated herein by reference.

The (S)—N,N-dimethyl-3-hydroxy-3-(aryl)-propanamine may optionally be recovered after carrying out step (b), prior to the demethylation step (c). The demethylated product, (S)—N-methyl-3-hydroxy-3-(aryl)-propanamine, may subsequently be recovered and optionally further purified after carrying out step (c) using methods that are well known in the art. The present invention includes (S)—N-methyl-3-hydroxy-3-(aryl)-propanamine produced by the methods described herein.

In a further embodiment, the present invention provides a method of making an (S)-3-aryloxy-3-(aryl)-propanamine, the method comprising:

(a) providing a 3-aryl-3-ketopropanamine having the structure of formula (I):

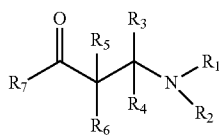

(b) contacting the 3-aryl-3-ketopropanamine with a ketoreductase polypeptide of the present invention in a reaction mixture under conditions sufficient to produce an (S)-3-aryl-3-hydroxypropanamine having the structure of formula (II):

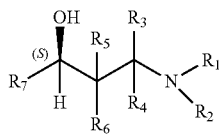

and
(c) contacting the (S)-3-aryl-3-hydroxypropanamine with an activated aryl compound in a reaction mixture under conditions sufficient to produce the (S)-3-aryloxy-3-arylpropanamine having the structure of formula (VII)

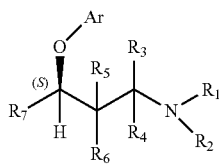

wherein for (I), (II), and (VII), $R_1$ and $R_2$ are each independently selected from the group consisting of hydrogen, an optionally substituted lower alkyl, an optionally substituted cycloalkyl, an optionally substituted aryl, or alternatively, where $R_1$ and $R_2$ together form an optionally substituted cycloalkyl or an optionally substituted cycloaryl having 3-7 carbon atoms; $R_3$, $R_4$, $R_5$, and $R_6$ are each independently selected from the group consisting of hydrogen and an optionally substituted lower alkyl; and $R_7$ is an optionally substituted aryl and additionally, for (VII), Ar is an optionally substituted aryl group. Typically, $R_1$-$R_7$ are substituents as described hereinabove with respect to formulas (I)

and (II). Typically, Ar is an aryl selected from the group consisting of 1-naphthyl, phenyl, 4-trifluoromethylphenyl, 2-methylphenyl, 2-methoxyphenyl, and 2-thiomethoxyphenyl.

The method may optionally include a demethylation step if $R_1$ and $R_2$ of the 3-aryl-3-ketopropanamine are both methyl as described hereinabove. The demethylation step may occur before or after step (c). Preferably, the demethylation step occurs before step (c).

As used herein, the term "activated aryl compound" refers to an aryl compound that is substituted with a leaving group. Suitable leaving groups include halides (such as, for example, fluoro-, chloro-, and the like), pseudohalides (such as, for example, sulfonates, such as triflate, tosylate, mesylate, and the like), and the like. Reaction conditions sufficient to produce the 3-aryloxy-3-(aryl)-propanamine having the structure of formula (VII) include contacting the 3-aryl-3-hydroxypropanamine with the activated aryl compound in the presence of an alkali metal hydride, such as, for example, sodium hydride, potassium hydride, and the like, or an alkali metal hydroxide, such as, for example, potassium hydroxide, sodium hydroxide, and the like. The 3-aryl-3-hydroxypropanamine may also be contacted with an aryl compound activated with a pseudohalide (such as, for example, triflate, tosylate, and the like) or a halide in the presence of a transition metal catalyst (such as, for example, palladium (Pd), Copper (Cu), and the like). The reaction is carried out in a solvent, such as, for example, N,N-dimethylacetamide, dimethylsulfoxide, dimethylformamide, pyridine, and the like. The reaction is typically carried out at a temperature in the range of from about 10° C. up to the reflux temperature of the solvent used. Methods for preparing a 3-aryloxy-3-(aryl)-propanamine from a 3-aryl-3-hydroxypropanamine are described, for example, in, U.S. Pat. Nos. 5,023,269, 5,491,243, 6,541,668, WO 2007/095200, EP 0 457 559A2, and EP 0 273 658A1, all of which are incorporated herein by reference.

The methods for making a 3-aryloxy-3-(aryl)-propanamine optionally include the further step of making a pharmaceutically acceptable salt of the 3-aryloxy-3-(aryl)-propanamine. Methods for making a pharmaceutically acceptable salt are well known in the art. See, for example, U.S. Pat. Nos. 5,023,269, 5,491,243, 6,541,668, WO 2007/095200, EP 0 457 559A2, and EP 0 273 658A1, all of which are incorporated herein by reference. Pharmaceutically acceptable acid addition salts are typically prepared by reacting a 3-aryloxy-3-(aryl)-propanamine with an equimolar or excess amount of acid. Suitable acids include both inorganic and organic acids. Exemplary inorganic acids include hydrochloric, hydrobromic, hydroiodic, nitric, sulfuric, phosphoric, metaphosphoric, pyrophosphoric, and the like. Exemplary organic acids include aliphatic mono- and dicarboxylic acids, substituted alkanoic acids (e.g., phenyl-substituted, hydroxyl-substituted, and the like), aromatic acids, aliphatic and aromatic sulfonic acids, and the like.

In some embodiments, the methods relate more specifically to use of the ketoreductase polypeptides provided herein in the synthesis of Duloxetine (i.e., (3S)—N-methyl-3-naphthalen-1-yloxy-3-thiophen-2-yl-propan-1-amine), having the structural formula (VIII):

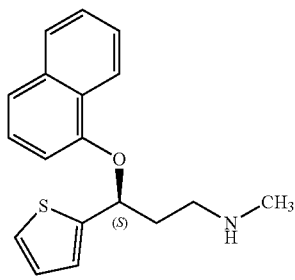

(VIII)

and salts, hydrates and solvates thereof. Accordingly, in a method for the synthesis of the compound of formula (VIII), a step in the method can comprise stereoselectively reducing the substrate of structural formula (III) to the corresponding alcohol product of structural formula (IV) by contacting or incubating the substrate with any one or more of the ketoreductase polypeptides of the disclosure. Once formed, the compound of structure (IV) can be used with known methods for synthesis of the compound of formula (VIII). An exemplary process is described in patent publication US2007/0167636, the description of which are incorporated herein by reference.

The present invention therefore provides methods for making Duloxetine, i.e., (3S)—N-methyl-3-naphthalen-1-yloxy-3-thiophen-2-yl-propan-1-amine (Formula VIII). In one embodiment the method comprises:

(a) providing N,N-dimethyl-3-keto-3-(2-thienyl)-1-propanamine;

(b) contacting the N,N-dimethyl-3-keto-3-(2-thienyl)-propanamine with a ketoreductase polypeptide of the present invention in a reaction mixture under conditions sufficient for producing (S)—N,N-dimethyl-3-hydroxy-3-(2-thienyl)-1-propanamine;

(c) demethylating the (S)—N,N-dimethyl-3-hydroxy-3-(2-thienyl)-1-propanamine to produce (S)—N-methyl-3-hydroxy-3-(2-thienyl)-1-propanamine; and (d) contacting the (S)—N-methyl-3-hydroxy-3-(2-thienyl)-1-propanamine with an activated naphthalene in a reaction mixture under conditions sufficient to produce (3S)—N-methyl-3-naphthalen-1-yloxy-3-thiophen-2-yl-propan-1-amine (Duloxetine) having the structure of formula (VIII); and (e) recovering the (3S)—N-methyl-3-naphthalen-1-yloxy-3-thiophen-2-yl-propan-1-amine from the reaction mixture.

In another embodiment for making Duloxetine, the method comprises:

(a) providing N-dimethyl-3-keto-3-(2-thienyl)-1-propanamine;

(b) contacting the N-dimethyl-3-keto-3-(2-thienyl)-propanamine with a ketoreductase polypeptide of the present invention in a reaction mixture under conditions sufficient for producing (S)—N-methyl-3-hydroxy-3-(2-thienyl)-1-propanamine; and (c) contacting the (S)—N-methyl-3-hydroxy-3-(2-thienyl)-1-propanamine with an activated naphthalene in a reaction mixture under conditions sufficient to produce (3S)—N-methyl-3-naphthalen-1-yloxy-3-thiophen-2-yl-propan-1amine (Duloxetine) having the structure of formula (VIII); and (d) recovering the (3S)—N-methyl-3-naphthalen-1-yloxy-3-thiophen-2-yl-propan-1-amine from the reaction mixture.

As used herein, the term "activated naphthalene" refers to an activated aryl as described above, where the aryl group is 1-naphthyl. Reaction conditions for carrying out the naphthylation and demethylation are as previously described above in the description of the method for making a 3-aryloxy-3-arylpropanamine from an (S)-3-aryl-3-hydroxypropanamine. Demethylating agents suitable for use in the method for making Duloxetine from (S)—N,N-dimethyl-3-napthalen-1-yloxy-3-thiophen-2-yl-propan-1-diamine include those described hereinabove. Methods for preparing a 3-arloxy-3-arylpropanamine from a 3-aryl-3-hydroxypropanamine are described, for example, in, U.S. Pat. Nos. 5,023,269, 5,491,243, and 6,541,668, WO 2007/095200, EP 0 457 449A2, and EP 0 273 658A1, all of which are incorporated herein by reference.

Various features and embodiments of the disclosure are illustrated in the following representative examples, which are intended to be illustrative, and not limiting.

EXAMPLES

Example 1: Wild-type Ketoreductase Gene Acquisition and Construction of Expression Vectors Ketoreductase (KRED) encoding genes are designed for expression in *E. coli* based on the reported amino acid sequence of the ketoreductase and using standard codon-optimization methods. Standard codon-optimization software is reviewed in e.g., ÓPTIMIZER: a web server for optimizing the codon usage of DNA sequences," Puigbò et al., *Nucleic Acids Res.* (2007 July); 35 (Seb Server issue): W126-31, Epub 2007 Apr. 16. Genes are synthesized using oligonucleotides, generally composed of 42 nucleotides, which are cloned into the expression vector pCK110900, depicted as FIG. 3 in United States Patent Application Publication 20060195947, which is incorporated herein by reference, under the control of a lac promoter. This expression vector also contains the P15a origin of replication and the chloramphenicol resistance gene. Resulting plasmids are transformed into *E. coli* W3110 using standard methods. Codon-optimized genes and the encoding polypeptides as well are listed in Tables 2 and 3, and their sequences provided in SEQ ID NO: 5-112. Ketoreductases useful for development of enzymes capable of reducing compounds of Formula (III) to the compounds of Formula (IV) are provided in Table 3, below.

TABLE 3

| Ketoreductase | Microorganism from which enzyme was originally identified | Genbank Accession Number | GI number | Polynucleotide SEQ ID NO | Polypeptide SEQ ID NO or source |
|---|---|---|---|---|---|
| ADH-CM | Candida magnoliae | AB036927.1 | 12657576 | SEQ ID NO: 33 | SEQ ID NO: 34 |
| YDL | Saccharomyces cerevisiae | NP_010159.1 | 6320079 | SEQ ID NO: 39 | SEQ ID NO: 40 |
| ADH-LB | Lactobacillus brevis | 1NXQ_A | 30749782 | SEQ ID NO: 3 | SEQ ID NO: 4 |
| ADH-RE | Rhodococcus erythropolis | AAN73270.1 | 34776951 | SEQ ID NO: 5 | SEQ ID NO: 6 |
| YGL | Saccharomyces cerevisiae | NP_011476 | 6321399 | SEQ ID NO: 37 | SEQ ID NO: 38 |
| YPR | Saccharomyces cerevisiae | NP_010656.1 | 6320576 | SEQ ID NO: 41 | SEQ ID NO: 42 |
| GRE | Saccharomyces cerevisiae | NP_014490.1 | 6324421 | SEQ ID NO: 43 | SEQ ID NO: 44 |
| ADH-LK | Lactobacillus kefir | AAP94029.1 | 33112056 | SEQ ID NO: 1 | SEQ ID NO: 2 |
| ADH-SB | Sporobolomyces salmonicolor | Q9UUN9 | 30315955 | SEQ ID NO: 47 | SEQ ID NO: 48 |
| ADH-SC | Streptomyces coelicolor | NP_631415.1 | 21225636 | SEQ ID NO: 45 | SEQ ID NO: 46 |
| ADH-TB | Thermoanaerobium brockii | X64841.1 | 1771790 | SEQ ID NO: 55 | SEQ ID NO: 56 |
| ADH-CP | Candida parapsilosis | BAA24528 | 2815409 | | Julich Chiral Solutions Cat. No. 03.11 |
| DR-LB | Lactobacillus brevis diacetyl reductase | ABJ63353.1 | 116098204 | | Julich Chiral Solutions Cat. No. 8.1 |
| ADH-HE | Horse liver | DEHOAL | 625197 | SEQ ID NO: 57 | SEQ ID NO: 58 |
| ADH-CB | Candida boidinii | CAD66648 | 28400789 | | Julich Chiral Solutions Cat. No. 02.10 |
| LDH-LL | Lactobacillus leichmannii | | | | Fluka Cat. No. 61306 |
| ADH-AF | Aspergillus flavus | P41747 | 1168346 | SEQ ID NO: 49 | SEQ ID NO: 50 |
| ADH-OO1 | Oenococcus oeni | ZP_00318704.1 | 48864831 | SEQ ID NO: 51 | SEQ ID NO: 52 |
| ADH-RU | Ralstonia eutropha | ZP_00202558.1 | 46131317 | SEQ ID NO: 53 | SEQ ID NO: 54 |

As noted above, polynucleotides encoding engineered ketoreductases described in the present disclosure may also be cloned into vector pCK110900 for expression in *E. coli* W3110.

Example 2: Production of Ketoreductase Powders—Shake Flask Procedure

A single microbial colony of *E. coli* containing a plasmid encoding a ketoreductase of interest is inoculated into 50 mL Luria Bertani broth containing 30 μg/ml chloramphenicol and 1% glucose. Cells are grown overnight (at least 16 hrs) in an incubator at 30° C. with shaking at 250 rpm. The culture is diluted into 250 ml Terrific Broth (12 g/L bacto-tryptone, 24 g/L yeast extract, 4 ml/L glycerol, 65 mM potassium phosphate, pH 7.0, 1 mM MgSO$_4$) containing 30 μg/ml chloramphenicol, in a 1 liter flask to an optical density at 600 nm (OD$_{600}$) of 0.2 and allowed to grow at 30° C. Expression of the ketoreductase gene is induced by addition of iso-propyl-β-D-thiogalactoside ("IPTG") to a final concentration of 1 mM when the OD$_{600}$ of the culture is 0.6 to 0.8 and incubation is then continued overnight (at least 16 hrs). Cells are harvested by centrifugation (5000 rpm, 15 min, 4° C.) and the supernatant discarded. The cell pellet is resuspended with an equal volume of cold (4° C.) 100 mM triethanolamine (chloride) buffer, pH 7.0 (including 2 mM MgSO$_4$ in the case of ADH-LK (SEQ ID NO: 4) and ADH-LB (SEQ ID NO: 2) and engineered ketoreductases derived therefrom), and harvested by centrifugation as above. The washed cells are resuspended in two volumes of the cold triethanolamine (chloride) buffer and passed through a French Press twice at 12,000 psi while maintained at 4° C. Cell debris is removed by centrifugation (9000 rpm, 45 min., 4° C.). The clear lysate supernatant is collected and stored at −20° C. Lyophilization of frozen clear lysate provides a dry powder of crude ketoreductase enzyme. Alternatively, the cell pellet (before or after washing) may be stored at 4° C. or −80° C.

Example 3: Production of Ketoreductases—Fermentation Procedure

Bench-scale fermentations are carried out at 30° C. in an aerated, agitated 15 L fermentor using 6.0 L of growth medium (0.88 g/L ammonium sulfate, 0.98 g/L of sodium citrate; 12.5 g/L of dipotassium hydrogen phosphate trihydrate, 6.25 g/L of potassium dihydrogen phosphate, 6.2 g/L of Tastone-154 yeast extract, 0.083 g/L ferric ammonium citrate, and 8.3 ml/L of a trace element solution containing 2 g/L of calcium chloride dihydrate, 2.2 g/L of zinc sulfate septahydrate, 0.5 g/L manganese sulfate monohydrate, 1 g/L cuprous sulfate heptahydrate, 0.1 g/L ammonium molybdate tetrahydrate and 0.02 g/L sodium tetraborate). The fermentor is inoculated with a late exponential culture of E. coli W3110 containing a plasmid encoding the ketoreductase gene of interest (grown in a shake flask as described in Example 2) to a starting $OD_{600}$ of 0.5 to 2.0. The fermentor is agitated at 500-1500 rpm and air is supplied to the fermentation vessel at 1.0-15.0 L/min to maintain a dissolved oxygen level of 30% saturation or greater. The pH of the culture is maintained at 7.0 by addition of 20% v/v ammonium hydroxide. Growth of the culture is maintained by addition of a feed solution containing 500 g/L cerelose, 12 g/L ammonium chloride and 10.4 g/L magnesium sulfate heptahydrate. After the culture reaches an OD600 of 50, expression of ketoreductase is induced by addition of isopropyl-β-D-thiogalactoside (IPTG) to a final concentration of 1 mM and fermentation continued for another 14 hours. The culture is then chilled to 4° C. and maintained at that temperature until harvested. Cells are collected by centrifugation at 5000 G for 40 minutes in a Sorval RC12BP centrifuge at 4° C. Harvested cells are used directly in the following downstream recovery process or they may be stored at 4° C. or frozen at −80° C. until such use.

The cell pellet is resuspended in 2 volumes of 100 mM triethanolamine (chloride) buffer, pH 6.8, at 4° C. to each volume of wet cell paste. The intracellular ketoreductase is released from the cells by passing the suspension through a homogenizer fitted with a two-stage homogenizing valve assembly using a pressure of 12000 psig. The cell homogenate is cooled to 4° C. immediately after disruption. A solution of 10% w/v polyethyleneimine, pH 7.2, is added to the lysate to a final concentration of 0.5% w/v and stirred for 30 minutes. The resulting suspension is clarified by centrifugation at 5000 G in a standard laboratory centrifuge for 30 minutes. The clear supernatant is decanted and concentrated ten fold using a cellulose ultrafiltration membrane with a molecular weight cut off of 30 kD. The final concentrate is dispensed into shallow containers, frozen at −20° C. and lyophilized to powder. The ketoreductase powder is stored at −80° C.

Example 4: Analytical Methods: Conversion of N-methyl-3-keto-3-(2-thienyl)-1-propanamine ("MMAK") to (S)—N-methyl-3-hydroxy-3-(2-thienyl)-1-propanamine ("(S)-MMAA")

Achiral HPLC method to determine conversion of N-methyl-3-keto-3-(2-thienyl)-1-propanamine ("MMAK") to (S)—N-methyl-3-hydroxy-3-(2-thienyl)-1-propanamine ("(S)-MMAA"): Reduction of MMAK (prepared as described WO2004020391) to (S)-MMAA was determined using an Agilent 1100 HPLC equipped with an Agilent Zorbax 5 μm SB-Aq column (15 cm length, 2.1 mm diameter), using 8:2 40 mM NH4Ac/MeCN as eluent at a flow 0.4 ml/min; and a column temperature 50° C. Retention times: MMAA: 1.9 min; MMAK: 2.5 min. The product was determined as the peak area at 235 nm and the substrate as the peak area at 290 nm.

Chiral HPLC method to determine stereopurity of MMAA: Stereomeric purity of MMAA was determined using an Agilent 1100 HPLC equipped with Shiseido CD-Ph reverse phase chiral column (25 cm length, 4.6 mm diameter) using 7:3 $NaClO_4$/MeCN as the eluent at a flow rate of 1 ml/min and at a temperature of 35° C.). Retention times: (R)-MMAA: 10.7 min; (S)-MMAA: 13.6 min; MMAK: 8.9 min.

Example 5: Prescreen for Ketoreductases Capable of Reducing Isopropanol in the Presence of $NADP^+$ Yielding NADPH and Acetone Recombinant E. coli colonies carrying a gene encoding ADH-LK or a variant thereof were picked using a Q-Bot® robotic colony picker (Genetix USA, Inc., Boston, MA) into 96-well shallow well microtiter plates containing 180 μL Terrific Broth (TB), 1% glucose and 30 μg/mL chloramphenicol (CAM). Cells were grown overnight at 30° C. with shaking at 200 rpm. A 10 μL aliquot of this culture was then transferred into 96-deep well plates containing 390 μL Terrific Broth (TB), 1 mM $MgSO_4$ and 30 μg/mL CAM. After incubation of the deep-well plates at 30° C. with shaking at 250 rpm for 2 to 3 hours, recombinant gene expression within the cultured cells was induced by addition of IPTG to a final concentration of 1 mM. The plates were then incubated at 30° C. with shaking at 250 rpm for 18 hrs.

Cells were pelleted by centrifugation (4000 RPM, 10 min., 4° C.), resuspended in 400 μL lysis buffer and lysed by shaking at room temperature for 2 hours. The lysis buffer contained 100 mM triethanolamine (chloride) buffer, pH 7, 1 mg/mL lysozyme, 500 μg/mL polymixin B sulfate ("PMBS") and 1 mM $MgSO_4$. After sealing the plates with aluminum/polypropylene laminate heat seal tape (Velocity 11 (Menlo Park, CA), Cat #06643-001), they were shaken vigorously for 2 hours at room temperature. Cell debris was collected by centrifugation (4000 RPM, 10 min., 4° C.) and the clear supernatant was assayed directly or stored at 4° C. until use.

In this assay, 20 μl of sample (diluted in 100 mM triethanolamine(chloride) buffer, at the same pH as the lysis buffer, and 1 mM $MgSO_4$) was added to 180 μl of an assay mixture in a well of 96-well black microtiter plates. Assay buffer consisted of 100 mM triethanolamine (chloride) buffer, pH 7, 50% isopropyl alcohol (IPA), 1 mM $MgSO_4$ and 222 μM $NADP^+$. The reaction was followed by measuring the reduction in fluorescence of $NADP^+$ as it was converted to NADPH using a Flexstation® instrument (Molecular Devices, Sunnyvale, CA). NADPH fluorescence was measured at 445 nm upon excitation at 330 nm. If desired, samples of lysates may be preincubated at 25-40° C. in the presence or absence of 50% IPA prior to addition to the assay mixture.

Example 6: High-Throughput Screening for Identification of Variants of the Lactobacillus kefir Ketoreductase (ADH-LK) Capable of Stereospecifically Converting N-methyl-3-keto-3-(2-thienyl)-1-propanamine ("MMAK") to (S)—N-methyl-3-hydroxy-3-(2-thienyl)-1-propanamine ("(S)-MMAA")

The gene encoding ADH-LK, constructed as described in Example 1, was mutagenized using methods described above and the population of altered DNA molecules was used to transform a suitable E. coli host strain. Antibiotic resistant transformants were selected and processed to identify those expressing an ADH-LK variant with an improved ability to reduce N-methyl-3-keto-3-(2-thienyl)-1-propanamine ("MMAK") ("the monomethyl substrate") stereospecifically to (S)—N-methyl-3-hydroxy-3-(2-thienyl)-1-propanamine ("(S)-MMAA") ("the monomethyl product"). Cell selection, growth, induction of ADH-LK variants and collection of cell pellets were as described in Example 5.

Example 7: Assay of ADH-LK Activity—Stereospecific Reduction of N-methyl-3-keto-3-(2-thienyl)-1-propanamine to (S)—N-methyl-3-hydroxy-3-(2-thienyl)-1-propanamine Cell lysis: Cell pellets were lysed by addition of 400 µL lysis buffer (1 mM MgSO$_4$, 0.5 mg/ml polymyxin B sulfate ("PMBS"), 1 mg/ml lysozyme, 100 mM triethanolamine (pH~6), and 1 mg/mL NADP$^+$) to each well. The plates were sealed, shaken vigorously for two hours at room temperature, and then centrifuged at 4000 rpm for 10 minutes at 4° C. The supernatants were recovered and stored at 4° C. until use.

Enzymatic reduction reaction: An aliquot (450 µL) of a mixture of isopropanol and solid substrate (N-methyl-3-keto-3-(2-thienyl)-1-propanamine) was added to each well of a Costar® deep well plate using a Multidrop instrument (MTX Lab Systems, Vienna VA), followed by robotic addition of 50 µL of the recovered lysate supernatant using a Multimek™ instrument (Multimek, Inc., Santa Clara CA), to provide a reaction comprising 10 mg/ml substrate N-methyl-3-keto-3-(2-thienyl)-1-propanamine, 0.1 mg/ml NADP$^+$, 10 mM triethanolamine pH~6, and 90% isopropanol (v/v). The plates were heat-sealed with aluminum/polypropylene laminate heat seal tape (Velocity 11 (Menlo Park, CA), Cat #06643-001) at 170° C. for 2.5 seconds and then shaken overnight (at least 16 hours) at ambient temperature. Reactions were quenched by the addition of 1 ml of 95% acetonitrile. Plates were resealed, shaken for 5 min, and then centrifuged at 4000 rpm for 10 min. A 250 µL aliquot of the cleared reaction mixture was transferred to a new shallow well polypropylene plate (Costar #3365), which was sealed, after which the extracts were subjected to HPLC analysis using methods described above (e.g., see Example 4).

For high throughput screening at pH~6 and 85% IPA (v/v), 50 µl of cell lysate containing 1 g/L NADP$^+$ was transferred to a deep well plate (Costar #3960) containing 450 µl of assay mix (per 100 ml: 5 ml 100 mM triethanolamine (chloride) (pH 7), 13.4 g MMAK, and 95 ml isopropyl alcohol). After sealing the plates, reactions were run for at least 16 hours at ambient temperature. Reactions were quenched by the addition of 1 ml of 95% acetonitrile, and the plates were sealed with aluminum/polypropylene laminate heat seal tape (Velocity 11 (Menlo Park, CA), Cat #06643-001), shaken for 5-10 min, and centrifuged at 4000 rpm for 10 minutes. 250 µL of the cleared reaction mixture was transferred to a new shallow well polypropylene plate (Costar #3365), which was then sealed. The extracts prepared in this manner were subjected to HPLC analysis as described above.

Variants of the *Lactobacillus kefir* ketoreductase (ADH-LK) capable of converting N-methyl-3-keto-3-(2-thienyl)-1-propanamine to (S)—N-methyl-3-hydroxy-3-(2-thienyl)-1-propanamine were identified using the approaches and procedures disclosed above. Multiple iterations of these processes, in which one or more improved isolates from one round were used as the starting material for subsequent rounds of mutagenesis and screening, were used to develop or "evolve" *Lactobacillus kefir* ketoreductase (ADH-LK) variants with an improved ability to reduce N-methyl-3-keto-3-(2-thienyl)-1-propanamine stereospecifically to (S)—N-methyl-3-hydroxy-3-(2-thienyl)-1-propanamine.

Example 8: Stereoselective Reduction of MMAK Using Isopropyl Alcohol for Co-Factor Regeneration by Engineered Ketoreductases Derived from ADH-LK Improved ketoreductases derived from ADH-LK variants were evaluated at preparative scale for the reduction of MMAK as follows. A 100 µL solution of the ADH-LK variant to be tested (10 mg/mL) and NADP-Na (1 mg/mL) in 100 mM triethanolamine(chloride) buffer pH 7 were combined in a 5 mL reaction vial equipped with a magnetic stir bar. Subsequently, 850 µL of isopropyl alcohol ("IPA") were added to the enzyme/NADP-Na solution, followed by 120 mg of MMAK hydrochloride. The reaction was stirred at ambient temperature and monitored by HPLC analysis of samples taken periodically from the reaction using analytical methods disclosed above (see Example 4). Table 2 provides the SEQ ID NO. corresponding to ketoreductase variants, the number of amino acid mutations from the wild-type ADH-LK, and MMAK-reducing activity of each, relative to that of the enzyme having the amino acid sequence of SEQ ID NO: 6.

This Example illustrates that engineered ketoreductases derived from the ketoreductase ADH-LK provide improved activities compared to the wild-type ketoreductase ADH-LK for the reduction of MMAK.

Example 9: Preparative Scale Production of MMAA

A solution of the ketoreductase of SEQ ID NO: 28 (400 mg), and NADP$^+$ (20 mg) in 10 ml 100 mM triethanolamine (chloride) (pH 8.5) was slowly added to rapidly-stirring IPA (90 mL) in a 3-neck 250 mL flask equipped with a distillation head, septum and thermoprobe, followed by addition of substrate MMAK (14.6 g). This mixture was vacuum distilled such that the temperature in the pot is maintained between 23.5 and 25° C. (~50 mmHg, the vacuum was adjusted to provide the desired reaction temperature). The rate of distillation was about 10 ml/hr. IPA (90% in water was added periodically to replace that which was distilled off. At 4 hours, the conversion is 73%. At this time distillation was stopped and an additional amount of the ketoreductase of SEQ ID NO: 28 (200 mg) and NADP$^+$ (10 mg) were added in 5 ml of triethanolamine buffer. Distillation was continued for a total of 9 hours (conversion: 97%). The reaction mixture was left stirring overnight at room temperature yielding a final conversion of 99%. Then 30 ml of 25% NaOH were added and, after stirring for 10 minutes, the lower layer was removed by pipette. The remaining IPA solution was filtered through a celite pad to remove denatured enzyme and then concentrated using a rotavap. Toluene (70 ml) was added and the mixture again concentrated. An additional portion of toluene (30 ml) was then added and the resulting solution was first warmed to redissolve product that precipitates at room temperature, and then filtered through celite. MTBE (40 ml) was added to the filtrate and the mixture (containing precipitated product) was stirred overnight. The slurry was cooled to approximately -10° C. with an ice/methanol bath (1 hr) and filtered (MTBE wash). The product was dried in vacuo to afford MMAA as white crystals in ~75% yield.

All patents, patent publications, journals, and other references cited in this disclosure were hereby incorporated-by-reference in their entirety.

What is claimed is:

1. A ketoreductase polypeptide capable of converting substrate N-methyl-3-keto-3-(2-thienyl)-1-propanamine to product (S)—N-methyl-3-hydroxy-3-(2-thienyl)-1-propanamine at a rate that is improved over a reference polypeptide having the amino acid sequence of SEQ ID NO:6, wherein the polypeptide has an amino acid sequence that is at least 90% identical to a reference sequence based on SEQ ID NO:2, comprising a residue substitution relative to SEQ ID NO: 2 at one or more positions selected from 40, 46, 60, 64, 108, 145, 152, 153, 157, 190, 196, 198, 199, 226, 245, and 249.

2. The ketoreductase polypeptide of claim 1, wherein the residue substitution at position 190 is cysteine, proline, or a constrained amino acid; the residue substitution at position 46 is arginine; the residue substitution at position 60 is isoleucine; the residue substitution at position 64 is valine; the residue substitution at position 108 is histidine; the residue substitution at position 152 is asparagine; the residue substitution at position 153 is valine; the residue substitution at position 157 is serine; the residue substitution at position 198 is asparagine; and/or the residue substitution at position 245 is isoleucine.

3. The ketoreductase polypeptide of claim 1, wherein the polypeptide is capable of converting the substrate to the product with a percent stereomeric excess of at least 95%.

4. The ketoreductase polypeptide of claim 1, wherein the polypeptide is capable of converting the substrate to the product with a percent stereomeric excess of at least 99%.

5. The ketoreductase polypeptide of claim 1, wherein the polypeptide is capable of converting the substrate to the product at a rate that is at least 10-15 times greater than the rate of conversion of the substrate to the product by the reference polypeptide of SEQ ID NO:6.

6. The ketoreductase polypeptide of claim 1, wherein the polypeptide is capable of converting the substrate to the product at a rate that is at least 15 times greater than the rate of conversion of the substrate to the product by the reference polypeptide of SEQ ID NO:6.

7. The ketoreductase polypeptide of claim 1, wherein the polypeptide is capable of converting at least 95% of the substrate to the product in less than about 24 hours when carried out with greater than 100 g/L of substrate and less than 5 g/L of the polypeptide.

* * * * *